United States Patent
Biradar et al.

(10) Patent No.: US 11,647,709 B1
(45) Date of Patent: May 16, 2023

(54) MAIZE PLANTS WITH IMPROVED DISEASE RESISTANCE

(71) Applicant: MONSANTO TECHNOLOGY LLC, St. Louis, MO (US)

(72) Inventors: Sunil Kumar Biradar, Bangalore (IN); Sonali Dilip Gandhi, Bergschenhoek (NL); Hemareddy Hirenallur Basappa, Bangalore (IN); Peter Vincent Maloney, Galena, MD (US); Yule Pan, Chesterfield, MO (US); Veeresh Gowda Rp, Bangalore (IN); Dharanendra Swamy, Bangalore (IN); Hao Zhou, Chesterfield, MO (US)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 0 days.

(21) Appl. No.: 16/548,613

(22) Filed: Aug. 22, 2019

Related U.S. Application Data

(60) Provisional application No. 62/726,705, filed on Sep. 4, 2018.

(51) Int. Cl.
*A01H 1/04* (2006.01)
*A01H 5/10* (2018.01)
*A01H 6/46* (2018.01)

(52) U.S. Cl.
CPC .......... *A01H 1/04* (2013.01); *A01H 5/10* (2013.01); *A01H 6/46* (2018.05)

(58) Field of Classification Search
None
See application file for complete search history.

(56) References Cited

U.S. PATENT DOCUMENTS

| | | | | |
|---|---|---|---|---|
| 9,167,781 B2 * | 10/2015 | Baltenberger | ........... | A01H 5/10 |
| 9,237,715 B2 * | 1/2016 | Potrzeba | ............... | A01H 1/02 |
| 10,477,800 B2 * | 11/2019 | Ochs | .................... | A01H 6/4684 |
| 10,779,498 B1 * | 9/2020 | Bhatnagar | ............ | A01H 6/4684 |
| 2015/0351340 A1 | 12/2015 | Bundock et al. | | |

OTHER PUBLICATIONS

Jines, M.P., Balint-Kurti, P., Robertson-Hoyt, L.A., Molnar, T., Holland, J.B., and Goodman, M. M. "Mapping resistance to Southern rust in a tropical by temperate maize recombinant inbred topcross population"; Theor Appl Genet (2007) 114: 659-667 (Year: 2007).*

Chavez-Medina, J.A., Leyva-Lopez, N. E., "Resistance to Puccinia polysora in Maize Accessions". 2007. Plant Dis. 91:1489-1495 (Year: 2007).*

Ming, R. "Restriction fragment length polymorphism analysis of host-plant resistance to four maize pathogens". University of Hawaii Dissertation. (Year: 1995).*

Puchta and Hohn. "From centiMorgans to base pairs: homologous recombination in plants". Trends in Plant Science. 1(10): 340-348. (Year: 1996).*

Chavez-Medina, J.A., Leyva-Lopez, N. E. "Resistance to Puccinia polysora in Maize Accessions" Plant Dis. 91:1489-1495 (Year: 2007).*

Wanlayaporn, et al. "QTL Mapping for Partial Resistance to Southern Corn Rust Using RILs of Tropical Sweet Corn". American Journal of Plant Sciences. 4: 878-889. (Year: 2013).*

Wijnker et al. "Managing meiotic recombination in plant breeding". Trends in Plant Science 13:12, p. 640-646 (Year: 2008).*

Wanlayaporn et al. "QTL mapping for partial resistance to southern corn rust using RILs of tropical sweet corn". American Journal of Plant Sciences. 4(4):878-889 (Year: 2013).*

Kianian et al. "High-resolution crossover mapping reveals similarities and differences of male and female recombination in maize". Nature Communications. 9(2370):1-10. (Year: 2018).*

Wisser et al. "The genetic architechture of disease resistance in maize: a synthesis of published studies". Phytopathology. 96: 120-129. (Year: 2005).*

Liu et al. "Genome-Wide High-Resolution Mapping by Recurrent Intermating Using *Arubidopsis thulium* as a Model" Genetics 142: 247-258. (Year: 1996).*

MazieGDB.org. https://www.maizegdb.org/bin_viewer?bin=6&sub=01 (Year: 2021).*

MazieGDB.org BLAST result SEQ ID No. 32 (Year: 2022).*

Heffner, et al., "Genomic Selection for Crop Improvement," Crop Science, 2009, 1-12, 49(1).

Nakaya, et al., "Will genomic selection be a practical method for plant breeding?" Annals of Botany, 2012, 1303-1316, 110.

* cited by examiner

*Primary Examiner* — Matthew R Keogh
*Assistant Examiner* — David R Byrnes
(74) *Attorney, Agent, or Firm* — Dentons US LLP; Matthew Madsen

(57) ABSTRACT

The present invention is in the field of plant breeding and disease resistance. More specifically, the invention includes a method for breeding corn plants containing one or more markers that are associated with resistance to fungi. The invention further includes germplasm and the use of germplasm containing at least one marker associated with resistance to southern rust (SR) infection for introgression into elite germplasm in a breeding program, thus producing novel SR resistant germplasm.

13 Claims, No Drawings
Specification includes a Sequence Listing.

SEQUENCE LISTING

```
<160> NUMBER OF SEQ ID NOS: 415

<210> SEQ ID NO 1
<211> LENGTH: 201
<212> TYPE: DNA
<213> ORGANISM: Zea mays
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (180)..(180)
```

<223> OTHER INFORMATION: n is a, c, g, or t

<400> SEQUENCE: 1

```
ggggtgccat ttttaatttg taaaccactt gaccggntat ggnctgaatt tcataaggac    60
caaagtagng gtaggatata ggttgtgaca gaccctggaa ntcaccgaag attgagcaca   120
aggttgcagt ttcaaccaaa ctctatctat cgtccactgc aaattggtgt tatgtacgan   180
aattttgtca gcataacttt c                                             201
```

<210> SEQ ID NO 2
<211> LENGTH: 667
<212> TYPE: DNA
<213> ORGANISM: Zea mays
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (626)..(628)
<223> OTHER INFORMATION: n is a, c, g, or t
<220> FEATURE:
<221> NAME/KEY: misc_feature
<222> LOCATION: (649)..(649)
<223> OTHER INFORMATION: n is a, c, g, or t
<220> FEATURE:
<221> NAME/KEY: misc_feature
<222> LOCATION: (659)..(661)
<223> OTHER INFORMATION: n is a, c, g, or t

<400> SEQUENCE: 2

```
nnnngcctca acgatggcgt gccgtctagc tgcccctgcc accgcagtgc cgncctcgtc     60
gtcttccggg cacttcttgc agatgcgcag caacgctgac acgacgagcg cngtggccgc    120
gtcggacacg cagaacattt tcttgaccag cacgggcatg ncgagtgcgt cngcacgagc    180
acgcgctctg ccgtcgcgag acgccagtgc tgcatcgagc gcggcgagag ccttctcggc    240
cgtgctcctg tcagcgtcca cgaggagctc gacgagcacg ntcacgatcc ccgccaccga    300
gaggcgcgtc gcggcgctct cgccgctgcg cgcgaggtgg tacgcggcga ccaggcacgc    360
cctngtggcc ggcgggcaga tggcgtctct gatcgtcttc accaacactc gggcganggc    420
ctcggtnttg gcgcacagac cgatcgtaca cgcggnacct ctgtaaactg anagcgagat    480
gatctctctg attaccacca cggcttgcag cctcctgtgc aggtcgccgt tcgcggcgac    540
ggcgaccagc cgcgctacgg acgcgctcga cgagcccacg accaggatgg cctcttcgtc    600
nattggcatc acgagcacca gcgctnnnag cacagcgtcg agcacatcna tggcgaccnn    660
ngcatct                                                              667
```

<210> SEQ ID NO 3
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 3

```
agcgacaggc ggtctgcgta caatcacgga cggtccaggc acatacccgg acaatccgcg     60
cataccaccg gacggtctgc atattcgacc ggacgttccg nggtagagtt ttttgaggaa    120
gattgctact tgaatcctca tccgccccag caacacctcc cctcacacta tactatgcat    180
cagcccatta atacggaatc t                                              201
```

<210> SEQ ID NO 4
<211> LENGTH: 1253
<212> TYPE: DNA
<213> ORGANISM: Zea mays
<220> FEATURE:
<221> NAME/KEY: misc_feature
<222> LOCATION: (1)..(29)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (1211)..(1217)
<223> OTHER INFORMATION: n is a, c, g, or t
<220> FEATURE:
<221> NAME/KEY: misc_feature
<222> LOCATION: (1220)..(1222)
<223> OTHER INFORMATION: n is a, c, g, or t
<220> FEATURE:
<221> NAME/KEY: misc_feature
<222> LOCATION: (1232)..(1238)
<223> OTHER INFORMATION: n is a, c, g, or t
<220> FEATURE:
<221> NAME/KEY: misc_feature
<222> LOCATION: (1252)..(1252)
<223> OTHER INFORMATION: n is a, c, g, or t

<400> SEQUENCE: 4

```
nnnnnnnnnn nnnnnnnnnn nnnnnnnnnc tgctgcagag cacttcattt tgcaacttga      60
aaaggttgag ataaacttct gtattgtgca aacaaattta taatgttgca atttagtgtg     120
tatatagata tgtttttatt gtaattttgc acttgtcgaa ttttatgtta tttgttcgac     180
tccaaattta tatatgaata gcctatctat caagagctta atgctctaat ttttctctcc     240
cacttaggca tttgagtccc ccaacactca tgctgagtgc ttcacatatc tgcggcaata     300
cgcggagaat tgttctgcga aggctgcttg tatggtggca cctaagagca tcatctccta     360
cccacaggtt tcaactcacc tactcctgct cttgttttgc tganctatac gtccacaatg     420
cgtcgctgct agcttcacac ttttttgttg cttttcatga caagttggtg ttgagcattg     480
tcagtattgg cacttcagag tttagattgg agaggaaggc taacacgttg tatcacgaac     540
acaggtctgg aaagggcaag ggtcgaggaa gtggaagctt gaccagagcg acgggttctt     600
cgtgcaattc gaggcaccgg cgctgaggaa gatatggttt gtgccaagca caaagagaa      660
gggacggaca ttgtgcaggt aaatctctct ctccctcccc cttttttttc ctacttgaca     720
gttctaaagt agtcggttca gaactagttt cagcttccaa aaccagtgtc ttctaaaatt     780
aaaatgctgt ccatgcgctg ccgtactgct caccttgttc agacgatcat gcttactaga     840
gtaggaccaa gaccaacaag tgaactgtgc ctgtaatcgc aaatggaaaa cagaaacggc     900
aaaccttgtc atccaccttc caccatgaaa agcctcacgt ccttccctct ttatggtagt     960
cacaagaggt aggacaacgt actgtactgt actgactgga gtacatcgcg ctcccctct    1020
ttattgcccg tgcacgcagg agccctgagg ccttggacat cggcatccat gaagtgctcc    1080
cccgtatatt caaggaggca gcttaagccc aataatggag gactgtccat ggattcctga    1140
tcctgcacag cgcttgctgg atgttctccc tgggacctgg gaggaggaaa gagctcgccc    1200
gacatacatt nnnnnnncan nnaatcggct annnnnnnag acgcagactc gna           1253
```

<210> SEQ ID NO 5
<211> LENGTH: 686
<212> TYPE: DNA
<213> ORGANISM: Zea mays
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:

```
<221> NAME/KEY: misc_feature
<222> LOCATION: (482)..(482)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (624)..(625)
<223> OTHER INFORMATION: n is a, c, g, or t
<220> FEATURE:
<221> NAME/KEY: misc_feature
<222> LOCATION: (639)..(647)
<223> OTHER INFORMATION: n is a, c, g, or t
<220> FEATURE:
<221> NAME/KEY: misc_feature
<222> LOCATION: (649)..(657)
<223> OTHER INFORMATION: n is a, c, g, or t
<220> FEATURE:
<221> NAME/KEY: misc_feature
<222> LOCATION: (676)..(684)
<223> OTHER INFORMATION: n is a, c, g, or t

<400> SEQUENCE: 5
gcagctgaaa aaattgacag agcatcatca tctgaggtca gcaaccctga tactagtaca      60
tcagaaacng gttctccatt ctatcagctt agaacagatg ctacnaaact tgttgcacaa     120
acatttcaaa gagggcgaag aaatctttgg cagctggcaa caagtcgctt atctgttnta     180
ttatctagtt cggctgtttg ttcaactagc acataccaat tnctgaagaa ttatgaagat     240
cttgccatnt tcattttggc tggcgaagca ttttgtggat ttgaagctag tgagttccgc     300
cagaagttga agactgtctg tttgaactac atggtgtcct ttcaccggca aaatgtatat     360
gtatgtcaat anctctgact cggttcttaa tgatnagtgc tcaaagttca aacatgtgaa     420
ttttgaactg ctatcatctt tttaactgct taaaatgtgt atgcagttca tgacgtgttt     480
gnagtcttta cgaacattct tcntatttct tttcttttct tcattggtag tgctggtttc     540
acagtagccc attttgtaa ctgattttga tataagctac cagtgctttt atgtttctac      600
aaaaggagtt tgcagctgat atgnncatta gtcagtgcnn nnnnnnnann nnnnnnngca     660
ttgatatgca ccatannnnn nnnngt                                          686

<210> SEQ ID NO 6
<211> LENGTH: 371
<212> TYPE: DNA
<213> ORGANISM: Zea mays
<220> FEATURE:
<221> NAME/KEY: misc_feature
<222> LOCATION: (81)..(81)
<223> OTHER INFORMATION: n is a, c, g, or t

<400> SEQUENCE: 6
acaaattcat ctttaaattg gccctacata tgatataact cacactgagt aactgttgat      60
atcatattct aaatgactaa nagatttcag ttattagcat attatgatat cacacacctt     120
tccaacaacc tcaaacgtcc attgtttcaa ccggaaggcc actgcgttta gatgattatt     180
tggcatggag gcccagtgtg tatcaccatt taaactctga aaaggttaga ctttccctga     240
tgaaaccttc taattaagtg ggtaagcaaa gcactattca gtaattgtat cacctcctgt     300
tctagcagga atctccaaaa tctcttcacc aggccaaact ccgtggggaa cgtgttactc     360
actttgtgct t                                                          371

<210> SEQ ID NO 7
<211> LENGTH: 945
```

```
<212> TYPE: DNA
<213> ORGANISM: Zea mays
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t

<400> SEQUENCE: 7
tttgtgcagt tggttgctga ggtactgaat tcagagtagc atgctgtgca gtataaacac    60
cctgatacaa gaaaaggtga gacaataata cggaacatac acatactagt tgagaccaaa   120
accaacatta tctgctcaga aaacaacaaa agaactaatg tctactagca aacaggaaac   180
atataatcaa taagactcgt tcctgttaat actaaagcag aaatactgac agtgagnaat   240
aaataatttc aaagatgaaa catcagatct atggccttgg ggttattcac ttactgacac   300
attaacagaa tcccttatgg gatttagaga ttctaaacgt ttcttcagct cctccaatct   360
tgcatattgg gaagcagcac tctcctggac ctagttaaac aaaagataaa agatcttaag   420
cacatatggt gaaatgatgg acatatattc ataaaaggaa aattagaagc atactagatg   480
gtttaggtca tcacataatt tctgcttagc atcctcttcg tctttaacaa cttgtgcagc   540
aacttcccaa gtctagaata ccagacacgt agtaaaaaat agcaganaac ataacttatt   600
gttagcgaca ctagaataaa agagaaacac aagtatttac aaagaaaaaa tagggaaaca   660
gtagaggtct gatcatctac acgagacatt actccctccg tctgaaataa gactatatac   720
ttctagcatt tgaaaattgt cctacaaaat aagtacactt ttagatcatg gaaaggcagc   780
ttcagtaagc tttactactc tctccatttc caaagtgtgc ctccccaaag agctcggtgg   840
tcttggaatt tgtgatctcc aaaaccttgg ctaggcgctt cagttgagat ggttgtgact   900
gaagaaaaca gatcctaatc aaacaaattt ttatgtgcca gtcca                   945

<210> SEQ ID NO 8
<211> LENGTH: 472
<212> TYPE: DNA
<213> ORGANISM: Zea mays
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (335)..(336)
<223> OTHER INFORMATION: n is a, c, g, or t
<220> FEATURE:
<221> NAME/KEY: misc_feature
<222> LOCATION: (457)..(471)
<223> OTHER INFORMATION: n is a, c, g, or t

<400> SEQUENCE: 8
tcgnnggctt gctgaggcaa ccctttttgtt tcggaaccga agactagcca gtcccctggc    60
ctgtaggaga aatcctaatt tcaaaacacg ggacaacatt aaccaagtga atgtgtacca   120
tttccgtaag aaaatcttcg naattgcaga ttagttcaga tatcccaca gcgacagttt   180
```

| | |
|---|---|
| tcattgtggc gacggcgagg atatactaca gtcctacttg aagaagcagc ggctacttac | 240 |
| tgaatggatg tgtgtgcctc ttttggtgaa cgccaacagc cttttatctc cttcctaatg | 300 |
| gggccaaaag aacgtgatga tgctgaaaag naatnngcag ttaaatatac gggagaataa | 360 |
| tggataatcc aacatcacct gtttcatgaa ataatcacag aagtggtccc aagagtcatg | 420 |
| aatcttgaca caacgtatc ttaaaggcag cgtttannnn nnnnnnnnnn ng | 472 |

```
<210> SEQ ID NO 9
<211> LENGTH: 628
<212> TYPE: DNA
<213> ORGANISM: Zea mays
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (216)..(218)
<223> OTHER INFORMATION: n is a, c, g, or t
<220> FEATURE:
<221> NAME/KEY: misc_feature
<222> LOCATION: (611)..(611)
<223> OTHER INFORMATION: n is a, c, g, or t

<400> SEQUENCE: 9
```

| | |
|---|---|
| tccacctcca cccgctcgat ccctgcatac gcatgcgtgc gtgcgcattg agccatccac | 60 |
| gccaggatca ggtgaaaaaa acaacaacaa caccaccgac aacaacaaag cccagccgc | 120 |
| ccaggctttg ggtaaagaag aaggagctag aattaaagga cgttnagaat ccagatccag | 180 |
| cagctctcta cacagggagg gacgatggca gcagcnnntg ctgctgctgc ataccgatcg | 240 |
| tactggaagt aatgatcgat ctgccggccg ggggggccct ggcagctggt tggccggccg | 300 |
| gccggaatgg acggcggcgg gatggggtgg gctttgttga agcctgaagg cgctcatcac | 360 |
| ggacgtaacg tacgtacctt tcactttgga caggcatctg cgtacccgct tctcatgcaa | 420 |
| cgccaccatc tccactttca gctccgtgct ctgcgaaacg ccaccagcga tcaggaaacg | 480 |
| cgcacaggat tgggttgttc gttgtcgcaa caatgctgcc tttcatgcat ctgcatgtgc | 540 |
| agtgcagtcc cagctagcta gtagcttgcg ttgcttgctt gctcgcgaga gctagttcat | 600 |
| catgcaaagg naaaaggcag cactgcag | 628 |

```
<210> SEQ ID NO 10
<211> LENGTH: 331
<212> TYPE: DNA
<213> ORGANISM: Zea mays
<220> FEATURE:
<221> NAME/KEY: misc_feature
<222> LOCATION: (237)..(237)
<223> OTHER INFORMATION: n is a, c, g, or t

<400> SEQUENCE: 10
```

| | |
|---|---|
| ctggacacag ctgcctccac atcatccttt gtcactgtaa cctcctcttg ttcatgcccc | 60 |
| cattgtgtca cccctttgac tccaacctcc accccagttt tcagcacgtc caccaccagc | 120 |
| ctctcgttca caaactgctc tgcaaagtgt ggccatgtga tcatgggcac gcctgcacag | 180 |
| actccctcta atgtcgagtt ccacccacag tgtgtcatga aacctccaac agatctntgc | 240 |
| cacaggatca taacctgcgg cgcccagccc cttatgatca agcctctgtc cttcacccgt | 300 |
| tcttcaaacc catccgcgag ccattcctca a | 331 |

```
<210> SEQ ID NO 11
<211> LENGTH: 203
```

```
<212> TYPE: DNA
<213> ORGANISM: Zea mays
<220> FEATURE:
<221> NAME/KEY: misc_feature
<222> LOCATION: (110)..(110)
<223> OTHER INFORMATION: n is a, c, g, or t

<400> SEQUENCE: 11
gtccctgttc ttacaaatca ccccttacca acagacgcgt ttgggtcaaa aacccaagta      60
caacactagt agtagcagta cattacatag caacagtatt cacatcaacn gagtgcagct     120
tgaggatcat aattctacgg ataaaaagaa cacttcgccg tcttcacagg cttggctgaa     180
ccgcacttga agcaccctgt aga                                             203

<210> SEQ ID NO 12
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t

<400> SEQUENCE: 12
ccttcgctaa gaaagcgcaa atgtattacc agaggcgtcc gatgctcgtc acccacgtcg      60
agaacttcta ccgtatgtat cgtgctctag ccgagcgcta ngacaatgta accggcgagc     120
tgcgcaagaa catccctaca aggctgcaga caaccggatn tttaaccagt tcagagtacg     180
gttctgagct gcagaggtcn c                                               201

<210> SEQ ID NO 13
<211> LENGTH: 201
<212> TYPE: DNA
<213> ORGANISM: Zea mays
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t

<400> SEQUENCE: 13
cgacgctgaa cttgtcngac aacaggctcg taggaagcat accngcgtcg cctcacttct      60
cgacgttctc cagctcgtcg ttccaaggaa acgacggcct ntgcgggcct ccgctgtcca     120
aggcgtgcaa cgacaacgta acgcaggnag acgcggtgcg ttccgagaag agatctgtgg    180
acttcgtgct gttcctcttt g                                               201

<210> SEQ ID NO 14
```

```
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 14
tggcttttcc tcttcgacta gtgaattggt ctgaccgact gagcgcgcga ccatgtgttc        60
ttgttggcac gcaaacaagt cgaggagctt tactttaccg ngctactgga aatcatggcg       120
tgggctaccc ctacgcatgc atttcgcggg agcatggtgt ggttggcctg atcctgcaat       180
ttctgcggga tgatgcaaga c                                                 201

<210> SEQ ID NO 15
<211> LENGTH: 621
<212> TYPE: DNA
<213> ORGANISM: Zea mays
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (413)..(416)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t

<400> SEQUENCE: 15
attgaggaat tttcagcaga tgacatttgt ctgggatctc attttactga aacaccttcg        60
aaatctgcag cacaaaatgg aaaactgcac cacaaatcta tggaggtgat cggtcttgtt       120
cgtgatagat aaggaacaac gaaacacctg tgaaattta tcagtttgtt cttatattac        180
tatgatggca cntctgcagg ttattccatt cggatttgtt tttgaagatg atactctcnt       240
tgaagcatct gacagctnag tagaacctca cttgcgacat ctgccatgta acagcgttct       300
tgatgttgac cggcttctta attcggtatc tacttatctc ctggttcttc tacattgttc       360
aaaatgctct ggaaaaanga gcatttttaa tagaagttaa taaattctaa gannnnttat       420
antttatgta taggttttgg aaacatctca gcatgttgga aggatgtcag tttcaacaga       480
ccaggatttg cctttcaagg aggtagccaa ccaatgtgaa gcacttctga ttgggaagca       540
gcaaaagcta tctntctgca tgagtgttcg tgaaaaaaag gttagagatc gtgagcagct       600
tgagctgtcc acacagggggg a                                                621

<210> SEQ ID NO 16
<211> LENGTH: 201
```

```
<212> TYPE: DNA
<213> ORGANISM: Zea mays
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t

<400> SEQUENCE: 16
gaacaccaaa cagtctatag actaccgata acatgaaaca ntttgcttca gctccagggc      60
accaacagga acaaatgacc taactcgact tgtcatgatt ntcgtacgcg cgacgaagcc     120
aagcgttcct tccttccttt gtctcaagag ttgcaaagac atccngatga tgtttgtcta     180
ttaataattg agttgcgaag a                                               201

<210> SEQ ID NO 17
<211> LENGTH: 484
<212> TYPE: DNA
<213> ORGANISM: Zea mays
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (382)..(389)
<223> OTHER INFORMATION: n is a, c, g, or t
<220> FEATURE:
<221> NAME/KEY: misc_feature
<222> LOCATION: (394)..(408)
<223> OTHER INFORMATION: n is a, c, g, or t
<220> FEATURE:
<221> NAME/KEY: misc_feature
<222> LOCATION: (414)..(420)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (448)..(458)
<223> OTHER INFORMATION: n is a, c, g, or t
<220> FEATURE:
<221> NAME/KEY: misc_feature
<222> LOCATION: (475)..(477)
<223> OTHER INFORMATION: n is a, c, g, or t

<400> SEQUENCE: 17
acatccctca cgaaacacct cctgtcaatc tgcacattct tctcggcaac acacaacgac      60
acngccccga ccacaacaca agtcacaaat acagctccac ccagaacgct gttcagccca     120
acatcaccag caccgctccc cataaacgcc gcaatgctag caaacacgtc aggggctcca     180
ttaccaaagg ggagcagcgt cacgccagcc aaggtcggcg ggagccgcaa cagtgccgac     240
atcttctcaa ggctgcagca gaagtagtcg gcagcagtat tgcccagcat atagaacagc     300
gcggccaggc ataccccgag caccgcgtag cccagcaccc tgaacctctc gcatctgcag     360
tagaagaagc ctaggtagtc gnnnnnnnna atcnnnnnnn nnnnnnnncc taannnnnnn     420
```

```
gcagagaaaa ttcttactnt ngaggagnnn nnnnnnnntt ctgcacctct gagcnnncgc    480
ttct                                                                484
```

<210> SEQ ID NO 18
<211> LENGTH: 356
<212> TYPE: DNA
<213> ORGANISM: Zea mays
<220> FEATURE:
<221> NAME/KEY: misc_feature
<222> LOCATION: (49)..(49)
<223> OTHER INFORMATION: n is a, c, g, or t

<400> SEQUENCE: 18

```
catatataat aactactgta ggcagcggca tctcctgctg ggacgaagnt tcaagaagct     60
agctaagaga aagggcata acgagataat aagcagcgcg cgaagatgca agactgggcg    120
ccggtgttcg tctcgctggt gctcttcatc ctgctgtcgc cgggcctgct gttccagatg    180
ccgggcaagt gccggatcat cgagttcggc aacttccaga ccagcgccat ctccatcctc    240
gtccacgcca tcctcttctt cgccctcgcc gccatcttcc tcgtcgccgt cggggtgcac    300
atgtacctcg gctcctaggc ggcggcgcgg ggcgccgtac cttctctccc tctcta        356
```

<210> SEQ ID NO 19
<211> LENGTH: 517
<212> TYPE: DNA
<213> ORGANISM: Zea mays
<220> FEATURE:
<221> NAME/KEY: misc_feature
<222> LOCATION: (214)..(214)
<223> OTHER INFORMATION: n is a, c, g, or t

<400> SEQUENCE: 19

```
tgcgagccac cgattttct tttcatgaaa ggaacaggtg tgttttcaga tgcaaacatg      60
gccgtgctcc cccatcagca aatgcatata atctgtagaa tgcaaatcag tctctattcc    120 tgtatttta tttagtgaca cggtcatgct taagtagact gtacaatttt tttttcact     180 tgcagcatgg tgtggtgctg gtgctgacca ttangagcct tgatcgcca ctgtcctcca    240 gcatgttact ccagacaagg cagctgtcat cctttgagaa tgactgcagt tttttctacc    300
tcccttagct tttagtcagc ggtggagttg agacaatttt gttattggag ctagagtgct    360
gaattgagga gcgacatcaa tatgcccaag agattagaga gacggccaac ctgagtatct    420
tgctctgttg cgggggttttg cctgcttatg aagctgtgta tggtgatttt gttgttgtat    480
gtttatgagt aggctctgac tagcgaggat attctga                              517
```

<210> SEQ ID NO 20
<211> LENGTH: 537
<212> TYPE: DNA
<213> ORGANISM: Zea mays
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (212)..(212)
<223> OTHER INFORMATION: n is a, c, g, or t
<220> FEATURE:
<221> NAME/KEY: misc_feature
<222> LOCATION: (269)..(270)
<223> OTHER INFORMATION: n is a, c, g, or t
<220> FEATURE:
<221> NAME/KEY: misc_feature
<222> LOCATION: (314)..(315)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t

<400> SEQUENCE: 20

```
cgggcagcag gaagcctggt gttgtggtct aggcatggcc aaacagcagt ttagaaggat      60
atggaagggt tggaatgggg aggaagagaa cacgagagaa gaatgttgct aacgtgtgtg     120
cccatgatgc agaatggatg acgtggatgc taacacggca aaactagtgc catgtaggat     180
anaaatcagc ttcaaatggg cttgggtgtg gntgacacag aggggggcgag gggtttgtgg     240
tcttacaagt tataagatgg gtgtgtgtnn tggggagggg ggataaattg gacttctctt     300
ataattttca tatnncaaat ttctatctaa tacttgcact ggtgggtact gcaggacntt     360
gaacgacaac acacctngac aaaatattat gcatgttaac ttttttattt catagttcga     420
tatttcaata atttgtgagg gtcaacattt ctgctatggc tgttggtttt ctgtgtacat     480
ttgcccatca atatttgctg ctgttacttg ttttcatttt taaaccagaa catcatc       537
```

<210> SEQ ID NO 21
<211> LENGTH: 201
<212> TYPE: DNA
<213> ORGANISM: Zea mays
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t

<400> SEQUENCE: 21

```
atgagcaagt ggacaagtac taagatatac nntancannt taacactcac ttgagccact      60
atccatcgta gcttttgtag cagcaaccca atcatcaacg ntagctttcc agtccctgca     120
gcacanaacg aagagatcga taagttcatc anatggtaca agatagnaca tgcaatatta     180
aggtctatat attaaaggag c                                                201
```

<210> SEQ ID NO 22
<211> LENGTH: 779
<212> TYPE: DNA
<213> ORGANISM: Zea mays
<220> FEATURE:

```
<221> NAME/KEY: misc_feature
<222> LOCATION: (288)..(288)
<223> OTHER INFORMATION: n is a, c, g, or t

<400> SEQUENCE: 22
atagcatgag agtaagtaaa tgaacagttt gactgatgta gaaggtgcgg ttttcatgta      60
aaatggtacc aggatctgtc tcgaatatag ctaccggaac agcacgctcg ctcactggag     120
tgccctaaat attttaagaa aatcaagtta accatactaa agacaaatac aaataattca     180
acttgcccaa tattacaatt tacatgggca aactaatgcc acaaatatt tgccaacaag      240
aagaaagaac taattccacc aaaatgaatc aagggatgtt catgtagntc cttgatagga     300
tcacattagg gatgccaaaa taggacaggg gaaagaccac ggaaacataa cattgacaac     360
tatcctgatt tgaagttatg taagctgaat gattttaatc actgaaccac ttcaaagctt     420
acttgtggct cccgagcaac aatatattgg caatgtagtc ctttgtcttt aaccatcgaa     480
tctccaagaa attcggcaag tcttttttgct gtagttacag cacaagactt ctgctctccg    540
tagtcaacta aagatttact cattgtgctc gactccgata tgaaatcaag caattcactg    600
tcagcaatat caattccttg attctgtaac agaaaaatat ttttatatgt attgatcaat     660
aacataagtt ggttggcttg ttgaggattt agagaataag aatataagaa tatagttcat     720
tatacagatc gcttacatcc agtaggtcca accaccggtt agcaacagag gcaacagca     779

<210> SEQ ID NO 23
<211> LENGTH: 730
<212> TYPE: DNA
<213> ORGANISM: Zea mays
<220> FEATURE:
<221> NAME/KEY: misc_feature
<222> LOCATION: (244)..(244)
<223> OTHER INFORMATION: n is a, c, g, or t

<400> SEQUENCE: 23
acggcgcccc cgtcgtcttc ctcaagcaca acgtccgtac acactcacag gctattgctg      60
tgtgcagcat ataatcggga tgcagcgcaa cacgcgtggt tgatttgggg gtaatgccgc     120
gccgcggatg gtgcaggtga tcgacgagta cgacgagcag tcggaggtgg cggaccggct     180
gcgcatcaag atcgtgccgc tcttccattt ctacgtggac ggggtgctgg tggagtcgtt     240
cccnacgagg gacaaggaga ggatcatcgc cgtcatccgg aagtacacct cggtcgagcc     300
agagccagaa ccagaacctg agtgagtcac cactctctga tctgctttga tttgacaaag    360
ataccatcag aattcagaac cagatcttct agtgaaccaa cgatctcaac gactaagatg     420
tgaagatttt tttttccccg aatatgtagc tgagtgtgga taagtaagtg tcgatcaacg    480
atcaacgatc gaagggacgc attttctctc tctctgaaca tgaacacatc gctacgcttt    540
tgcagctgtt gtaagaattc gagtcgagct gacatttcca tttccctcgc agggaagaag    600
agcagcagca gcagcaggag gaggagtgat tccatttcca ctccagtggt ggacatcagt    660
ttcctcgagg gtgcagatag cctgctgaat cagagatatc atgcacaaca gcaccacagg    720
attgtttgga                                                            730

<210> SEQ ID NO 24
<211> LENGTH: 583
<212> TYPE: DNA
<213> ORGANISM: Zea mays
<220> FEATURE:
<221> NAME/KEY: misc_feature
<222> LOCATION: (22)..(24)
<223> OTHER INFORMATION: n is a, c, g, or t
```

```
<220> FEATURE:
<221> NAME/KEY: misc_feature
<222> LOCATION: (27)..(37)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (43)..(46)
<223> OTHER INFORMATION: n is a, c, g, or t
<220> FEATURE:
<221> NAME/KEY: misc_feature
<222> LOCATION: (48)..(51)
<223> OTHER INFORMATION: n is a, c, g, or t
<220> FEATURE:
<221> NAME/KEY: misc_feature
<222> LOCATION: (53)..(55)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (492)..(494)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (530)..(535)
<223> OTHER INFORMATION: n is a, c, g, or t
<220> FEATURE:
<221> NAME/KEY: misc_feature
<222> LOCATION: (539)..(548)
<223> OTHER INFORMATION: n is a, c, g, or t
<220> FEATURE:
<221> NAME/KEY: misc_feature
<222> LOCATION: (568)..(580)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t

<400> SEQUENCE: 24
ttttcttgta ctggatgaag tnnnccnnnn nnnnnnntnt aannnncnnn nannnatgca    60
tagaattttg gagcatgttg gaaggagacc tggaggcaca tctagggata ttcttggccc   120
acttgcgaga cgatctgagc gtcagactat cctggtttct gcaacaatac cattttcagt   180
tatacgagca gcaaggagtt ggggtcatga tccagttctc attagagcta aaagtgtagt   240
tccacttgat tcaatcactg tgccaagacc tgcgttatcn caaagtgacg ctaaccccag   300
ttcgtcatcg cagtcagtga accaagctgc tgttggcagc ttgccgccat ctttggaaca   360
ctactattgt acggccaagg cgcagcacaa ggttgacaca ttacggaggt gcatccatgc   420
tctggaagca cagacagtga ttgcatttat gaacaacacc aagccactga aggatgttgt   480
gtttaagttg gnnncccntg gtatcaaagc cactgagcta catggagacn nnnnnaagnn   540 nnnnnnncg acagttttga aaagttnnn nnnnnnnnn tnc                       583

<210> SEQ ID NO 25
<211> LENGTH: 427
<212> TYPE: DNA
<213> ORGANISM: Zea mays
<220> FEATURE:
<221> NAME/KEY: misc_feature
<222> LOCATION: (150)..(150)
```

<223> OTHER INFORMATION: n is a, c, g, or t

<400> SEQUENCE: 25

```
gaattcaacg tggtgtttcc cgagcctggt gcgctctccc ctgcccagtg ccgatcgttg    60
gagaagatcc ttccgccgaa accagggagc caactgtcgg acatggagct ggaccagtgc   120
gaggagacca cccttcacga tgtcaacatn gaagaggaga tgaggcgcag gcagcagcag   180
aagaagcagg aagcctacga tgaagacgag gaggaggatg ctcaaccaag ggtgcaatgt   240
gcccagcagt aaaatccgtg ttcgttggaa ctgttctcca aaagtttcag caggattttt   300
tatccatctg atcatctcga ttcttttggg caaaaatata atcgttttat aaactttaaa   360
ctgttagttc catcctagtg tcagggaaaa aatgagagcc cggaatggca tgttccttgt   420
ttgaact                                                              427
```

<210> SEQ ID NO 26
<211> LENGTH: 399
<212> TYPE: DNA
<213> ORGANISM: Zea mays
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (392)..(395)
<223> OTHER INFORMATION: n is a, c, g, or t

<400> SEQUENCE: 26

```
tagcagcctc tactgcctcc acctctttaa tccttgtacc ttcacagtga acattgacga    60
cgagattcct gagggtggag aggtggctga tgccgaaatc aggagnacca aatctgcgtg   120
cagtatgcat ctcgtgcgct atgatttgaa actcaagagt ttcaagcgct ggaacagctc   180
cttctttgaa catcatgttt acccagccaa cgaaactgaa cttcttcaga catcggaatc   240
catcgttgct gacgacaagg cacattgggc acattgcctc agatcctgct gcatttgagg   300
acaccttcag gaattgtaag gcagggaaat ctccgaggat ctggagagtt tcttgtctaa   360
ctttaacctc aacgtccagg taggttaggt tnnnnagcg                          399
```

<210> SEQ ID NO 27
<211> LENGTH: 535
<212> TYPE: DNA
<213> ORGANISM: Zea mays
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t

```
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t

<400> SEQUENCE: 27
gctcgcaccg tctttgatag gtaaactgtg caanggaagc tgccagttat gncgagagaa      60
gaccgggctn acgtagcagt agacttggtc gttcagtggg tcatagtacg gnttcggatc     120
ttccaacggn gcagagaagg tgcagaggga actngcatac ttcaaaagcc accctggctt     180
tacgntcgtt acnccntgca tgtatagcct ctttgtacta agtagctccg agtaaactac     240
aagctctggg gcaacttggg cgacagatga tgatnggtgc agatatattg tatcatcaag     300
tgcacaagac tgntaacgaa cggctcgaac ctttcgatcg tcttctgatg ntttcnaata     360
ggtgtgaatc ctccttgcaa ctctatcagc ccatccagcg caaattcctt gcccaagaag     420
ttcctcttca ttcaactgca atatactggg ctcgttcctc caggcccgtt caacctcagc     480
agantcaccc gaattccaag caaactnctc gcaccatttg ctatggcgaa atatt         535

<210> SEQ ID NO 28
<211> LENGTH: 842
<212> TYPE: DNA
<213> ORGANISM: Zea mays
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
```

```
<221> NAME/KEY: misc_feature
<222> LOCATION: (478)..(478)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t

<400> SEQUENCE: 28
tgttgccgag acantggtct tgattggaac acctagtttg ctgcacaaat atattacatt      60
acanaatgag gcaaatatat attacattac ataacaaggc aaataatatc gagtaaagca     120
gaatagcaga tatatcatct ttaagctacc taaacagagc agcaaacact gtatttacag     180
tattgagact tgataggtcc agctccagtt cctgactatc tgcttcaatg gcctggacag     240
taacaaaaac attagtcaca cgaaaaaaaa cagtcagctc aaatgctcaa ccatgccncc     300
aatcacctca aaccctgatg cntcatactg gcgcctcttg tctggatctg acaggatatt     360
ataggagaat gtggcctctt gaaacttctc tgaggcaaca gggtcgtctg aattcttatc     420
tggatggtac ctgcatgaca aattttacta gatatataaa tactcagaca gctgcatngt     480
caccatcaat ttatcagtaa acaagatagc taaacagtct aaactaccaa taacntacac     540
ataaggcagg acagagcttc ttttttttct ttgcaagaca gagccttgct tgttgttccn     600
atttataatg cacgattcag aagctanata atactggtct ttacgtggtt ccaaaaggag     660 aggaattttat tcaagataat aaaacaatat acagctacgc atactcggaa caaaataagc     720
acaaaatgcg aactaatcta caaaaggaat ttgaacacag ncattccctc tgaggaaaat     780
aagagcacgc gaagtgccca aatccaagac cattgcagac aatacttact tgagtgccat     840
gc                                                                   842

<210> SEQ ID NO 29
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t

<400> SEQUENCE: 29
tggtagccat gcttggcttc atggtgcaag catccgtaac tcatgccggc cccatcgaca      60
atctcttgac acacctttcg gacccgttca acaaaaatat nattcacaca ttctcctctt     120
cctaagtact cgtcccaatg cccggatgcn atggcacaaa aaggtcacaa ngttttgaa      180 cacaacagaa caacatgatt a                                               201
```

<210> SEQ ID NO 30
<211> LENGTH: 520
<212> TYPE: DNA
<213> ORGANISM: Zea mays
<220> FEATURE:
<221> NAME/KEY: misc_feature
<222> LOCATION: (378)..(378)
<223> OTHER INFORMATION: n is a, c, g, or t

<400> SEQUENCE: 30

```
catcttgtgg ctttaattct tagatatttt accacgaacc atggaaacaa gttcaagtgt    60
gcctacctga cggttgctct tgtttagaa atctgaaatg ctatggcaga ataaacctg     120
aggcaggact acatatgcct acataaccaa tttaattagt ataataaata agcagtttac   180
actagactct tgagggacgt ttatgcttat gtgaggcttg cttcctgtag ataccgtgat   240
ccgaagacag ggctgcctta tgcaactatg gaagcattta aaataatccg ggagaggtac   300
attttgtttg ttctcataga ttcctacttt gctctgacag ctaagtcgta aaccacttgc   360
ctgcaatgtt tcttaagnaa aatactgctt tctatctgga tgcgcaatca aaacttgcta   420
acatctcttc aactgatcca tgcattcagt ttcctgaaag aggaggctga tagaaagcgt   480
ccgaacatgt cgaatatggg agagcttttc gaatcaataa                        520
```

<210> SEQ ID NO 31
<211> LENGTH: 502
<212> TYPE: DNA
<213> ORGANISM: Zea mays
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (395)..(396)
<223> OTHER INFORMATION: n is a, c, g, or t

<400> SEQUENCE: 31

```
aatcactctc ctcctccccg tcagcgtcag cgtcagcgtc agcgtcacgc tctgacgacg    60
acggcttntt tcttgcatgg tcatcgatga gcgtatcgag cagttcgtcc cacatcttgt   120
tcacccttcg tgccctcgca cacaccatcc tcttgaccat gtccagcttc accagcaccg   180
ggaagtagtc ctctaggttg aaaccccta tgagcgacga gttggcctcc accagctccc    240
ggaagagctt gttccgccct tcctccctga agaacttgcc ggacacagcg tggcaaacga   300
tgtcgttggc gaaggagttg agctgctcgc tcaggtcgaa ggcggcgcct gcggtggccg   360
cctcgcggat cttagacatc accagcctca cctannatat catttgtggg tgcttgtttt   420
cccaattgtt tgggtcacct tacataaaga ggaacaagtt gccctagcta agccaataat   480
cgcgcttcta tcgaaagatt ac                                           502
```

<210> SEQ ID NO 32
<211> LENGTH: 217
<212> TYPE: DNA
<213> ORGANISM: Zea mays
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:

```
<221> NAME/KEY: misc_feature
<222> LOCATION: (180)..(181)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t

<400> SEQUENCE: 32
atcttcttct gataaacttt catcactact aggtcatctg gataactctt catgtgttga      60
tagtagggaa ggacagaaaa aagntatggc ggccccagtc gatggtgaca ccgaagncgc     120
aagagcacca ccatcttctg ataaaacttc atcactagat aatctggata atccttcatn    180
ngttggnaag gaagaacagg aagaagntgt ggctcca                              217

<210> SEQ ID NO 33
<211> LENGTH: 699
<212> TYPE: DNA
<213> ORGANISM: Zea mays
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (576)..(579)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (591)..(592)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t
<220> FEATURE:
<221> NAME/KEY: misc_feature
<222> LOCATION: (628)..(631)
<223> OTHER INFORMATION: n is a, c, g, or t
<220> FEATURE:
<221> NAME/KEY: misc_feature
<222> LOCATION: (659)..(664)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (678)..(686)
<223> OTHER INFORMATION: n is a, c, g, or t
<220> FEATURE:
<221> NAME/KEY: misc_feature
<222> LOCATION: (688)..(693)
<223> OTHER INFORMATION: n is a, c, g, or t

<400> SEQUENCE: 33
caacaggagg gaactggacg caaggactgg acctaaagtc actaaacaac tgtacagaaa      60
gtccctttcg ggaggggtga ctttcatata tatataacca agatataact tggcgtacaa    120
gtaagatacn aacatatcta tagactatac atatctctag tagtgtcttg ttcaccatat    180
tataaagtta tgtaacactg atatatatct gaatgtgtta gtgaagacaa aagtctagca    240
cttaccaagc aggtgatctg caagtgagcc aagtgccatg tactcataaa ccagaagcct    300
```

-continued

```
ttgatctcca tctgcacaat agcccaccaa attgactagg tttggatggt gcaataggct    360
gagcatcagg acctcaacta ggaactctct gttgccttga tacccattca ggtctagttg    420
cttgacagca acaagctgtt cacgcaaacc ggaaacaagt cagccactaa tgactgtaga    480
tgaattagca agcttgtgta tacgtagaac gtttgaatgt ttttttctgt gtggtgtgta    540
cctgtccgtt ttcaagcctg cccttgtata ccctgnnnna tcccoctnct nngagaaggc    600 agtcagagcg gaagttttc gnggccgnnn ntagctcacg gaacgtgaat gcttttgcnn    660
nnnnggcaac agnacaannn nnnnnngnnn nnncgatgc    699
```

```
<210> SEQ ID NO 34
<211> LENGTH: 706
<212> TYPE: DNA
<213> ORGANISM: Zea mays
<220> FEATURE:
<221> NAME/KEY: misc_feature
<222> LOCATION: (19)..(130)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (536)..(540)
<223> OTHER INFORMATION: n is a, c, g, or t
<220> FEATURE:
<221> NAME/KEY: misc_feature
<222> LOCATION: (585)..(587)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (607)..(607)
<223> OTHER INFORMATION: n is a, c, g, or t
<220> FEATURE:
<221> NAME/KEY: misc_feature
<222> LOCATION: (621)..(622)
<223> OTHER INFORMATION: n is a, c, g, or t
<220> FEATURE:
<221> NAME/KEY: misc_feature
<222> LOCATION: (652)..(653)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (658)..(661)
<223> OTHER INFORMATION: n is a, c, g, or t
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (685)..(691)
```

<223> OTHER INFORMATION: n is a, c, g, or t
<220> FEATURE:
<221> NAME/KEY: misc_feature
<222> LOCATION: (695)..(699)
<223> OTHER INFORMATION: n is a, c, g, or t

<400> SEQUENCE: 34

| | | | | | |
|---|---|---|---|---|---|
| catcaggatt | ctccaatann | nnnnnnnnnn | nnnnnnnnnn | nnnnnnnnnn | 60 |
| nnnnnnnnnn | nnnnnnnnnn | nnnnnnnnnn | nnnnnnnnnn | nnnnnnnnnn | 120 |
| nnnnnnnnnn | agaatcgaag | aagccacact | gtaaatctgc | cgggaagcgg ctggtggcat | 180 |
| ccggcccgct | cctccctccg | ggcgccgcaa | cttttttcga | tcggttttgc gccgcccggg | 240 |
| acgggttgta | gttgatcgat | tggattcttc | ataactgtat | ttgcgtactg cttacactac | 300 |
| ccaagtgaaa | tcgaaaatgg | cgccttctct | cgttgaataa | attgcacgta cgctactcga | 360 |
| tccgctgcgg | ctcttgctgg | agtggccgcc | gccgctatag | atagaaggat caagccaagg | 420 |
| aatctgtcat | gcatggncat | gtgaaggagg | agcctcctgc | aatgtttagt cttttttgnt | 480 |
| cgacgcccac | cagagatata | cgcactagan | tttcatatag | ctgagctaga tcgatnnnnn | 540 |
| ccgttgcatg | catgctccat | gccgtcgaga | ttcgagctag | caccnnntnt tcatcatcga | 600 |
| ccgatcnatt | ctgatcgatt | nncctctcga | gctttcacga | actgaaccta cnnantgnnn | 660 |
| ntgacgcntn | acgcctagtg | cgcgnnnnnn | nggtnnnnna | tgtcag | 706 |

<210> SEQ ID NO 35
<211> LENGTH: 363
<212> TYPE: DNA
<213> ORGANISM: Zea mays
<220> FEATURE:
<221> NAME/KEY: misc_feature
<222> LOCATION: (235)..(235)
<223> OTHER INFORMATION: n is a, c, g, or t

<400> SEQUENCE: 35

| | | | | | |
|---|---|---|---|---|---|
| ctcgcctctc | gcccaccatg | gtgctcgtca | tgtcgctctg | cttcatcggc ttcgtcaccg | 60 |
| ccctccacat | cttcggcaag | ctctaccgct | cccgcacggc | cgcggcctcc gcgtgatccg | 120 |
| atccggtccg | gtcccaccgc | tcttgtggat | ccacacaacg | gatcagacta ccagatcaga | 180 |
| cggtgacttt | tttttttgggt | gatgaattat | gtatggggag | aagcccagct tgttntgttg | 240 |
| cctagctttt | gcttgatcct | tactttctca | acttagatct | cagctagatc tgcagatgga | 300 |
| aaccgtacat | gtcatcttaa | tgggggcccct | ttctgttatt | ttcttctctt cccttaccct | 360 |
| aaa | | | | | 363 |

<210> SEQ ID NO 36
<211> LENGTH: 1069
<212> TYPE: DNA
<213> ORGANISM: Zea mays
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (487)..(487)
<223> OTHER INFORMATION: n is a, c, g, or t

<400> SEQUENCE: 36

| | | | | | |
|---|---|---|---|---|---|
| aaatcccctc | taatcttcct | cactccacct | tacctgaaac | tcatgcttgg ccagcttggg | 60 |
| aagacgctct | catgtctgag | gtgctagttt | gctacagtga | cacaactatg gcttcaagca | 120 |
| catacatacc | atacaatact | ggggtcatga | tgaaatgtgg | ttgtttctat ctctgaaaca | 180 |

```
accttgaaat gaaagttgtt cctgctcttt gttatatgtg gtgctgtctt tgtatactga    240
aacttgggtc aaccataatg tagttcatgt tctaataccc aagaggccaa gatgctacna    300 cccttttgg gctccatttc atactgtaat tagttcaaga tacaagtcaa aggaagtaaa     360
ctgtaatccc tgatccctt gcttgttggt attaatatac attaaacttg tgataacaag    420
gaaagaatgg tgatacattt aggccagcac ttaattcttg ctgccctgct ggactgtacg    480
tatttgnatc aaggaccatt tcaagcctaa ctctattagt acacaaaaat aagttaccca    540
aaaaaaaagg agattgggtg ctcaagtgtt ggggtcggag acaattctct cgatctcttc    600
cagcaaccgc tccttctctt cggccaagtc ctcgttcttc tgttgaagct cctcgatctg    660
cttggtctgc tctgaatctt tcctgcaacc aaccgtgtgt ataaacattt taacaaacag    720
gtttacaaag ggaggtttgt gatcgctcca caaggatttt ccttagaaac tcgtgtcctt    780
gcttgcagca gtgtacccac ctgttcatga aggacagatt aagctttagc gaccgaacct    840
ccttctctag ggtttcgcag cgcttaagaa cggcctgcat gtcggacggt attactggtg    900
tagagcttct ttccttcgct tctgccattc tgaaccataa gaacgtaatg gaacatcaca    960
tactgtatgg taattatcaa ttaatgtgga ccattttttt aagaagggg gagcatcaca   1020 tacttgcggg agcgctcaac cctgcgcttt ttcataggat ctccattat              1069

<210> SEQ ID NO 37
<211> LENGTH: 654
<212> TYPE: DNA
<213> ORGANISM: Zea mays
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (537)..(538)
<223> OTHER INFORMATION: n is a, c, g, or t
<220> FEATURE:
<221> NAME/KEY: misc_feature
<222> LOCATION: (542)..(545)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (572)..(576)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (592)..(597)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (607)..(611)
<223> OTHER INFORMATION: n is a, c, g, or t
<220> FEATURE:
<221> NAME/KEY: misc_feature
<222> LOCATION: (613)..(613)
```

```
<223> OTHER INFORMATION: n is a, c, g, or t
<220> FEATURE:
<221> NAME/KEY: misc_feature
<222> LOCATION: (616)..(627)
<223> OTHER INFORMATION: n is a, c, g, or t
<220> FEATURE:
<221> NAME/KEY: misc_feature
<222> LOCATION: (631)..(633)
<223> OTHER INFORMATION: n is a, c, g, or t
<220> FEATURE:
<221> NAME/KEY: misc_feature
<222> LOCATION: (636)..(637)
<223> OTHER INFORMATION: n is a, c, g, or t
<220> FEATURE:
<221> NAME/KEY: misc_feature
<222> LOCATION: (641)..(653)
<223> OTHER INFORMATION: n is a, c, g, or t

<400> SEQUENCE: 37
gtgctcaaca tttggtgctt gggacctgaa caccatgtca ccgtgtttcc acagttccca      60
cacagttccc agcaaaagag tggtggagag ggtttccatg ggtactccta gcggagctgt     120
ggaggtccac agttcttgca ccgcggcgat catgtttggg ttcactccga ttctcatcca     180
gaaggctcga gcgaatggac acataaagat aatgttgttt gtgtcctcac cggcgagccc     240
acaaatgnca caagtgttca tgtcaaggac attcttcttt ctcaggttta tattgcagtg     300
actgtgattc taaatcagaa gccaagtaaa gaattttttca ctccggacag aggccttgta    360
gatgagatag ttggctagtc gcatcgtctt catcttcaaa gaagcatgag ggcacgtctg     420
ggttgtcact ctggttcaca cctaacagca tggactccag ttcgattgtc acctgcnggc     480
tcaagtgtgg tttcaattgt gttgcaagtc tggaagacat aacttcaatt gaaactnntc     540
tnnnnangtg gctgtgtagg gatggcagtt gnnnnnacaa cagcncgtca cnnnnnnact    600
gatcntnnnn nantgnnnnn nnnnnnncat nnacnnctg nnnnnnnnnn nnnt            654

<210> SEQ ID NO 38
<211> LENGTH: 589
<212> TYPE: DNA
<213> ORGANISM: Zea mays
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (559)..(561)
<223> OTHER INFORMATION: n is a, c, g, or t
<220> FEATURE:
<221> NAME/KEY: misc_feature
<222> LOCATION: (563)..(566)
<223> OTHER INFORMATION: n is a, c, g, or t

<400> SEQUENCE: 38
gcaactgaac tgggaaagaa ggccagggag ttaaaaaaag ctgctgaagc cctacaccaa      60
gaagaaagaa gtgggaacaa gggccggaaa tggcgcaaaa atgtgaaggc tttagaaaag     120
gtacatattg tattgaaatt gctctttcca cacattggta atgtttgtat gttacttta      180 caaaatgac aactatattt atccttttac atgtggtgtc ataaaataat cccaagagat     240
tagttaatgt catttgtcct ttacagttgt aggcatgcta cttcaaatac gtaaaagtta    300
tgtacctatt tgtttggtgc aatggtaaca acntgggtcc ctgagggtgt cactactggg   360
gaatgctgcg ctttgcaata ctttagtcat gtctgtcgat gatcagaata aagaagttat    420
cacttccaaa actttggctt aaagaaaact tggaagtatt tttaacatgt atttatagaa     480
```
gtcattgcat tttggagttt tagtggttaa caagttctct agttgagtta gtgtgaatgt    540
gcatgccata ttatgcttnn ntnnnnttca tatggaatca tggtcctta              589

<210> SEQ ID NO 39
<211> LENGTH: 1266
<212> TYPE: DNA
<213> ORGANISM: Zea mays
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (19)..(24)
<223> OTHER INFORMATION: n is a, c, g, or t
<220> FEATURE:
<221> NAME/KEY: misc_feature
<222> LOCATION: (120)..(122)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (447)..(455)
<223> OTHER INFORMATION: n is a, c, g, or t
<220> FEATURE:
<221> NAME/KEY: misc_feature
<222> LOCATION: (519)..(521)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:

```
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (751)..(752)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (965)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (971)..(974)
<223> OTHER INFORMATION: n is a, c, g, or t
<220> FEATURE:
<221> NAME/KEY: misc_feature
<222> LOCATION: (976)..(977)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1146)..(1152)
<223> OTHER INFORMATION: n is a, c, g, or t
<220> FEATURE:
<221> NAME/KEY: misc_feature
<222> LOCATION: (1172)..(1172)
<223> OTHER INFORMATION: n is a, c, g, or t
<220> FEATURE:
<221> NAME/KEY: misc_feature
<222> LOCATION: (1174)..(1174)
<223> OTHER INFORMATION: n is a, c, g, or t
<220> FEATURE:
<221> NAME/KEY: misc_feature
<222> LOCATION: (1179)..(1179)
<223> OTHER INFORMATION: n is a, c, g, or t
<220> FEATURE:
<221> NAME/KEY: misc_feature
<222> LOCATION: (1195)..(1197)
<223> OTHER INFORMATION: n is a, c, g, or t
<220> FEATURE:
<221> NAME/KEY: misc_feature
<222> LOCATION: (1214)..(1215)
<223> OTHER INFORMATION: n is a, c, g, or t
<220> FEATURE:
<221> NAME/KEY: misc_feature
<222> LOCATION: (1225)..(1231)
<223> OTHER INFORMATION: n is a, c, g, or t
<220> FEATURE:
<221> NAME/KEY: misc_feature
<222> LOCATION: (1244)..(1244)
<223> OTHER INFORMATION: n is a, c, g, or t
<220> FEATURE:
<221> NAME/KEY: misc_feature
<222> LOCATION: (1246)..(1246)
<223> OTHER INFORMATION: n is a, c, g, or t
<220> FEATURE:
<221> NAME/KEY: misc_feature
<222> LOCATION: (1254)..(1256)
<223> OTHER INFORMATION: n is a, c, g, or t
```

```
<220> FEATURE:
<221> NAME/KEY: misc_feature
<222> LOCATION: (1260)..(1263)
<223> OTHER INFORMATION: n is a, c, g, or t

<400> SEQUENCE: 39
nnnnnnnnng agggctctnn nnnngtaaga gccccccga gctgtgcccg aattatgatg      60
gacttgcaca gttgcactag cttgcgttgc ttgaacttgg acatctaatc gattttaatn    120
nnattgcttc agaaaaccag ctgctnctgc tgctgcaaat gctaaagatc aagctggctt    180
tgttggacac cgtccagtca ccaggtttgc aagctataac anctcacttc tgctacttta    240
ncancttgga tcgaattgcc atatatgtat caggttaatg nagtaatatg tcttgctatt    300 tttncccccag gaaattcgct gcaacattgg caanccaacc tacagttgcc cttctggtaa   360
tggtcgttaa agatactcaa attgttgcta gttcgatagt gcctgctctg ctgtttgctt    420
ctgtaaacct ccccattatg gcattannnn nnnnngaact gctgccacct agatagtttc    480
tgcttcttcg aatggtaaat acggcaattc aaacactcnn ncatncagtg gtgtgaaagn    540
gaattcagat ttttatttgc ncgcatagca tatcaatgct tgatatattt gaatgtgatg    600
cactatgntt ttgctgttag tttgttcatt cctgagtggg tggtaaatgt agccattcaa    660
atatgtggcc ggtgaagtgt gaaagggcac caacccatgg acttngnact tgtatatttg    720
aagtccttta tatatagnca ttcaaataaa nncagcttct gcatatagta tataaagctt    780
tgatcttcta acttgtgctg actgcccttg tatgttgtgt acatttgaat atgcatatat    840
agaatttgaa tattctacga ttttcctct tattctaggc cttgctgttc acatagccgg     900
ccaaatttct ttcngttcac atctccacat tactacacta acatccgacc ttgtttcaac    960
aagtnntant nnnnanncaa cagctcgat atttaattgt tgtgcaggac ccaattggaa    1020
gtgaaagact gaaaagaaac gctgatacgg catttcacac acctgcagat atggaangca   1080
caaaaatgac agatgacagt cccttgccta tgntgtcgga gatggatgaa atggtaagtt   1140
gacatnnnnn ncccttgat aaccagaaca tntntagtnt atttggtaat tgtcnnngat    1200
acaagtattt tcanntgagt cctgnnnnnn nagagatcga gatngnagat attnnngagn   1260 nnncac                                                              1266

<210> SEQ ID NO 40
<211> LENGTH: 324
<212> TYPE: DNA
<213> ORGANISM: Zea mays
<220> FEATURE:
<221> NAME/KEY: misc_feature
<222> LOCATION: (233)..(233)
<223> OTHER INFORMATION: n is a, c, g, or t

<400> SEQUENCE: 40
acagatgaac cgtgtgctat aattgtgagc agtaacattt ctacttgctc aaattagtca     60
gtacatgcgt atcaactact atacatcgat gtggttccta caagctgggc tctccattgc   120
tttgtgattg ctcgctctga cacaaaacac cgaaaagcat acgcaccgca agccttgtga   180
catctcaagc gacaaacagc tcggcctggc cgtcaatgaa caagctcatg aantcctccc   240
cgtccacggt ctccttctcg atcaggagct gggcgagctt gtggaggatg tcgatgtgcg   300
tggtgattat ctgcctgctt ctag                                          324

<210> SEQ ID NO 41
<211> LENGTH: 201
<212> TYPE: DNA
```

```
<213> ORGANISM: Zea mays
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 41
ttcctctcat gantcttcag ctctcgggac gagtacgcca ctactctccc ttcttgcatt       60
agcacacatc ctagaccagt gtacgaagca tcacaataca ntgagaatgg cttatgaaca      120
tgtggcacca gtatcaaatg gtacttttgc tggatgggat tngantggaa acatacctac     180
tgccacatct ngtncatcct n                                                201

<210> SEQ ID NO 42
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t

<400> SEQUENCE: 42
attccaatcc taagagcacg atttcagatt ttggaaatca cttttattct ctagcttcat       60
cataccaagg ttagcaactg ctgcttgtat tgcttgcaga ngtgacatcg cctcaatctc      120
cagtgcaact tcaacagcan ccatttggtc tntaacagca aaacccaaat caacgtctcc     180
gcntgcntgc atgcatgcgg g                                                201

<210> SEQ ID NO 43
<211> LENGTH: 507
```

<212> TYPE: DNA
<213> ORGANISM: Zea mays
<220> FEATURE:
<221> NAME/KEY: misc_feature
<222> LOCATION: (133)..(133)
<223> OTHER INFORMATION: n is a, c, g, or t

<400> SEQUENCE: 43

```
gtcatgtaag ggcagacagg atgaaattaa tcatgcataa gacatatgca ttgcaccgtc      60
agttatcatc aacatgatct gtatatatat accccgtgt gcacgcaggt acggttcatt     120
tgaagatggt gangcaaagc tagacgagat ggaaatggcg gatggtttcg agatagctat    180
caagaaactg acggaatggc ttgcagagaa cattgacaag aacaagacta ggatattttt    240
cgcaggatca tcaccaacac attcctggta atatatataa gatcgagatg tggtgttgtt    300
gttgttgttg ctgcttaatt aattaattaa tttcagggct agcaactggg gcggacaaga    360
caagaacaag tgcctgaacg aaacggagcc gatcagctac agacccggcg gcgggtacaa    420
ggctgcaacc acggactaca gcctgatggc catggccagg tcctacttcc ggcggacgct    480
ggagccgaga ggcatacgcg tccagat                                        507
```

<210> SEQ ID NO 44
<211> LENGTH: 518
<212> TYPE: DNA
<213> ORGANISM: Zea mays
<220> FEATURE:
<221> NAME/KEY: misc_feature
<222> LOCATION: (199)..(199)
<223> OTHER INFORMATION: n is a, c, g, or t

<400> SEQUENCE: 44

```
atctacctgc agagcattag agtgattgac tcaccaccat ataatatatt aaactaaatg      60
aactctagga aggaagcgca aagagctgtg aacagccaaa gaaaactaaa tccttaccct    120
ttctagctgc agcttgttag gatgttccgg aaatttttt gacatcgtga tgcaaatttt    180
ggggaaattt ggaaagacnc cagctttcca aaatgcatcc gagaatgtgt gcgtgtttgg    240
atctggatag tccaggatgc tgttcagccg gtacattttg gccagcaagc cttccgcaac    300
cttggacagc tgaaccaccg gctccatctg aagatgtttg tggctaccag cagaagagcc    360
ttgcggcgca tcagcgctca tgttcctcca ggttgccatt gcggaaggaa ttggctcttc    420
aacacttagg tattcagacc accgggacat gccgctgtcc atctttgc ttttgaacga     480
aacatgggcc atctcttcct tgagtagaga acagctgc                            518
```

<210> SEQ ID NO 45
<211> LENGTH: 402
<212> TYPE: DNA
<213> ORGANISM: Zea mays
<220> FEATURE:
<221> NAME/KEY: misc_feature
<222> LOCATION: (110)..(110)
<223> OTHER INFORMATION: n is a, c, g, or t

<400> SEQUENCE: 45

```
agaaaagaag caagaagtag aagagaaggg gacgacgagt aactaacctg ccgctgctgc      60
agtgctgcct gcgtgcctgc cggtggaact gacgaactct actctagacn gaccgaggaa    120
gatgagacca gagtggcaga tacgccttcg cccttgcctg gcctgaactc gaaacgttcc    180
ggtctcgttc cgtcggcggc ggcgtcaagt cgatgcaagc agaagcagga gcaggactac    240
gggaggtgaa acaggaaagc agggccgcag gggacagtgg ccagtggtgg tgctgtgaag    300
```

```
actgaagaca aggcgacatg gcattgggaa ccacgaaagc aaaagcttgg gtttctccct    360
ctgtcaagtt tatgtatatg tatgtaaagg aggaacgaag gt                       402
```

<210> SEQ ID NO 46
<211> LENGTH: 122
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 46

```
ggagtagtag gctagtagct agctagctag ctggtgcgtg tcgttcgtgg atggagaaat    60
ntaagagaga gagggagaga atggcggtcg ttgttcggtg gaaagtggaa tgtgtgaggg    120
ag                                                                   122
```

<210> SEQ ID NO 47
<211> LENGTH: 533
<212> TYPE: DNA
<213> ORGANISM: Zea mays
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t

<400> SEQUENCE: 47

```
ggtgcatggg gtacgcggcg ttcggcgaca aggcgccgga caacctgctg acggggttcg    60
gcttcttcga gccattctgg ctgatcgacg tggccaacgt ggccatcgtg gtgcacctgg    120
tgggcgcgta ccaggtgttc tgccagccca tcttcgcctt cgtggagcgc cgcgccgccg    180
cggcctggcc cgacagcgcc ttcgtctcgc gggagctccg cgtgggnccc ntcgccctca    240
gcgtgttccg cctcacgtgg cggtcggcgt tcgtgtgcgt caccaccgtn gtggccatgc    300 tgctccccttc ttcggcaac gtggtggggt tcctcggcgc cgtctccttc tggcccctca    360
ccgtctactt ccccgtcgag atgtacatca agcagcgccg cgtgccccgc ggcagcacca    420
agtgggtctg cctccagacg ctcagcgtcg cgtgcctggt cgtctccatc gccgccgccg    480
ccggctccat cgccgacgtc atcgaggcgc tcaaggttta ccacccgttc agc           533
```

<210> SEQ ID NO 48
<211> LENGTH: 122
<212> TYPE: DNA
<213> ORGANISM: Zea mays
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 48
acgttagttg ctgattttag gatntgtgca catcgcaagc aagggaatat ttggtgagct    60
nctatcgctc aatgaattta gatctagaat ttatcttagg acagtttgaa tacgttcatt   120
tt                                                                 122

<210> SEQ ID NO 49
<211> LENGTH: 701
<212> TYPE: DNA
<213> ORGANISM: Zea mays
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (662)..(664)
<223> OTHER INFORMATION: n is a, c, g, or t

<400> SEQUENCE: 49
gctgacactt aaaaaaagag taagatggaa aggaaatgta tcaattgaga gcagattgta    60
ttttattaag tatattatgt cactataacc tatttcaact tgttgagagc ctagcagcaa   120
ttcttgtggt cggtttatat ttttgccaca ctactaggct tcctgattag tccccccttc   180
aaccaatata tgtcactgga tgtagttaag caaaatgtca cgcagagcat ctattatctg   240
aatggcataa gtcagctgct gaaatgtatt gtagcattga antcaattgt gtgatcctac   300
gtgtgtagag tgtagactgc tttcaaaaca caacccttgg tcgaacaagt ataactgccc   360
cttcaacatt ttgggtcaac tgcagtgctg atctgtttat cctgcaggtc attcctttgc   420
ggaggatcaa ctgggttttt cgtgtacggc tactgcctgt actactacta tgcgcgatcc   480
gacatgtctg gcttcatgca gacatctttc ttctttggct acatggcctg catctgctat   540
gcattcttct tgatgctcgg gatggtgggc ttccgcgccg ccctgttctt tgtccgccac   600
atatacaaat caatcaagtg tgaatgagct gttgctgggg agacgaagag cagcagagtt   660
gnnnccgttt ttggtgcccc accgagaggt cccagatata g                      701

<210> SEQ ID NO 50
<211> LENGTH: 122
<212> TYPE: DNA
<213> ORGANISM: Zea mays
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 50
tccgaatctt acatttcgcg gatttcctcg ccctccagac tcctagtgaa aaccganngt    60
nttttctcct cgcgaatcag acgcgcttcc atctctaccg cgcaaggttt tgccaaaaaa   120
at                                                                 122

<210> SEQ ID NO 51
<211> LENGTH: 201
<212> TYPE: DNA
<213> ORGANISM: Zea mays
<220> FEATURE:
<221> NAME/KEY: misc_feature
<222> LOCATION: (15)..(15)

```
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (148)..(149)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t

<400> SEQUENCE: 51
ctaaagtaca acatnatttg aactaatgtg gtttagatag gaacaacaga gctcccatct      60
ttcctgacaa ctactgaata tgctattctt ggactttact nctccttccg atccaaatta    120
canantaccc caactttctt agagaatnna aaaaaaatct caagtttaan caaaagtana    180
nagagaattg canatattta t                                              201

<210> SEQ ID NO 52
<211> LENGTH: 201
<212> TYPE: DNA
<213> ORGANISM: Zea mays
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 52
aatggttgag ccattaaagc tcaaatgata aaagccacaa gcagnagaat caacagattt      60
ccagctgctc tttcaaaaat cgtagcacct cttcaaaggc ncgtgtcttg aaaattgatg    120
gacacgtcag aatctcgaaa tgacgagaaa aactgaaact ttgttcttgt gagagaaaaa    180
acaacccgca aattcctcag a                                              201

<210> SEQ ID NO 53
<211> LENGTH: 201
<212> TYPE: DNA
<213> ORGANISM: Zea mays
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
```

```
<222> LOCATION: (43)..(43)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t

<400> SEQUENCE: 53
taaaaaaaaa aacaaacttt ggaatgncca ttggctacat ggncagnccc ctagagaaat      60
ggcaccaatt tgtttcaaat tggctgatgc aagaatctca nagtggcgca ggcggttcaa     120
gacaacaggt ggatgaaagg gttgcatagg ntgtctactg gtcatggttt gatgcagttc     180
ttgattctat ggcgngcaat c                                               201

<210> SEQ ID NO 54
<211> LENGTH: 201
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 54
tttnatggat cctgtgttcn agngagtntg gagtggtttt gactagatgn anatntgcta      60
ggacctttaa aagtcatctc taccgaatag tttaggcaca nttctcgcaa gcatatatta    120
tattttaggg ttagtttgga aacttaaacc cccttcggga ttaccggaga ttagggggg     180 tttaagtttc taaactagac c                                               201

<210> SEQ ID NO 55
```

```
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t

<400> SEQUENCE: 55
ccagagcctt agtatgagta ggattaatac catatgatac cctcactaag aaggttctca      60
ncttcaatag taagctagtg agtgcttcta gagacaaatt gagaggaaga tctagnggac     120
t                                                                    121

<210> SEQ ID NO 56
<211> LENGTH: 121
<212> TYPE: DNA
<213> ORGANISM: Zea mays
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 56
gtgcgccatc acacagtgat gccatgctgg cgtagcctgg cgatggcagt acgnatgccg      60
nccgttgtgc ccgatgatgg aggagaaacc cgagaccacc ggttggctgt gttgtgctaa     120
t                                                                    121

<210> SEQ ID NO 57
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 57
tgacggtccg gggctaaaag cgttgcgtgc tgcctagctg tgtttgtggc attggactag      60
ntgatcatgc tgtttatcat gttnagaaaa gaatctgttg acgccnttttt cgaggcgcca    120 a                                                                    121

<210> SEQ ID NO 58
<211> LENGTH: 121
<212> TYPE: DNA
<213> ORGANISM: Zea mays
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
```

<222> LOCATION: (61)..(61)
<223> OTHER INFORMATION: n is a, c, g, or t

<400> SEQUENCE: 58
cgccgcggcg aggcgaaagc cacggggcg ctcgagacac canccgatct ggagcaggca 60
ncacggcgcc atccctggag aacagtggtg actgcgactg cgagtgcgaa cagatttcgc 120
a 121

<210> SEQ ID NO 59
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 59
catctagtta atgtagtacc aaaacatgaa tcgtatccaa actttgtcaa atatccatta 60
nactagaacc ggtgactcaa cagttcaaca ccccacacat attgaaagtc gcctagaatg 120
g 121

<210> SEQ ID NO 60
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t

<400> SEQUENCE: 60
gcgctgtagc agctaagctt tgccataacg gtcacgtgcg atgttcctca tcatgagcca 60
naaagtcgcg accaaacctg aaacgatccg caaggacggg aganaaaaaa antgtgcaag 120
t 121

<210> SEQ ID NO 61
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 61
cgacagagca gtagaggagc acctcctgca gccgcagcct agccaaacaa acagttggtt 60
ccatccaaac aaacagttgg ctccatccaa ttcgcaaatc nagagaggca gcaactacct 120
cgacagagct ttggactgca cacgtgagtt tcccaagacg caaaaggtga atataatgct 180
gacatatata gcttcgtcac a 201

<210> SEQ ID NO 62
<211> LENGTH: 201
<212> TYPE: DNA

```
<213> ORGANISM: Zea mays
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t

<400> SEQUENCE: 62
cctaacggat cagcactagg atcaggtaac tcagcagata tatatctatc aacgtcagca      60
acggaagcct cacnntctat atcacactgc caaaccagaa ngtgtgaatg aggtagccca     120
cgtttctgga actcatttgt ataggcaact gcatatgtga angttggccc tcgatctccc     180
tgcacaggtg atcaatcagc t                                               201

<210> SEQ ID NO 63
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 63
aacaccaaag cagtgacgca cggcaacaga ttctaataat attgttaacg atgcttggtc      60
ngtggagaaa ttggtttacg gctgatctga caatgacacg atgcagtggt gcaagttgag     120
g                                                                     121

<210> SEQ ID NO 64
<211> LENGTH: 904
<212> TYPE: DNA
<213> ORGANISM: Zea mays
<220> FEATURE:
<221> NAME/KEY: misc_feature
<222> LOCATION: (354)..(354)
<223> OTHER INFORMATION: n is a, c, g, or t

<400> SEQUENCE: 64
ctggtctgga tagcagattt tggacaaact tgtcacttct tcatttcaaa atacaatcag      60
acaaaaaaac gaaagcgtac atactggaac tcaccagctc aggggccaac ttttccggag     120
taatctttgc agctgaaaga agtacaccac gagcatcaga tcacagaaac acaaaaagtt     180
gtatttgcat gccaatggtt tcggtagtga atgaaagcgt acgtgactgt gattggaagc     240
tcttgttgta actcccggtc tccttgaaca gctgctcgaa atgggtcttg cagtacggca     300
ctccttcgaa cgaggaatag ttgctcagct gtcaaaggcg aaaaggatga aganggagat     360
tgtcagacct cgcacagctg cttatctttg cctagacatc gacaggtcgt cctaagtaga     420
agatcagata agagtgtcca tttgcatgga ttccctgccc aatcctcttt caccaagtta     480
gcgaatggga aacggacaaa gtcatgacct ctcctgggcg tagaattttt cctggtacta     540
ggaaactcgc accagatctg ttcgctgcgg caattcgcag atctactacc cgatgctaca     600
ttgcatcacc ctacagatcc atccacctac ccattagaag agagaagagc atgggcaagg     660
caaagggaac gtactgagag ggtagacttg cagtgctggc acttgaagca ggagcggtgg     720
aagacgacgc cgtcggtgga gagctggtcc atcgggtaca ccgtcttggt gcacaccttg     780
```

```
cacttctgct gcgtcccgct aaacatcttc ctcccgagca ccggtcaacc cccccttcg    840 gtctctgtct cacggcggcc ggcgagatct gagaggccgc cgatccggcc ttggcctgcg    900
cgcg                                                                  904
```

```
<210> SEQ ID NO 65
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t

<400> SEQUENCE: 65
atattagaag ttattgatga ccatttgtcc aacaccagta aaaatgttgc tagagatttc    60
nagncgtaag tgaattaggt ctttcaaagt accttaacta taagtacttt atagccanga   120
g                                                                    121
```

```
<210> SEQ ID NO 66
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 66
agccgtcaca atataaatct tttgagcgag gcgcatccaa taattcttca catatccaag    60
nggtagaaat gaggcaaacc ttttcaccaa acgagctagg ttatgcaaca ccccacacac   120
c                                                                    121
```

```
<210> SEQ ID NO 67
<211> LENGTH: 201
<212> TYPE: DNA
<213> ORGANISM: Zea mays
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 67
acctatagag gtcttatttg gatttgtcca agtcatctca attggtgttg acaagnttt     60 tcttcaattg gtgctatccg tagcctatca catatatcat ngttttgaac tcgaactctt   120
cttctatggc cacaaattca atgcaacaca catattttcg caatacttat aattgaacat   180
ggtgtctttt tgtaggccaa c                                              201
```

```
<210> SEQ ID NO 68
<211> LENGTH: 201
<212> TYPE: DNA
```

<213> ORGANISM: Zea mays
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t

<400> SEQUENCE: 68
aaaatataaa gatatgatat gtttaaaccg caattgcaaa ggtantaact acaataccag    60
ccaaaatcat taccttcacc aacttggatt tgattatctc ntgaaaatca tgagttgcgg   120
agatgagaac ctcttctcgc tccctccccc tgtcgcccat gcattttcta agacagttcc   180
atcacaactt ttttntctgt a                                             201

<210> SEQ ID NO 69
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t

<400> SEQUENCE: 69
catgcagagc tcgagggcag tctagcctag gaggcgttga agtctcaagg cctaaagcag    60
gaggtcgact agatctggga gtccatggcg aaggagtgca ncgagcatga gcttcttcgc   120
gttgctacac gattggtgng caccttggtg gcgccccaag cgaaggaatg agttcgattg   180
ttgcccagtt tgccgagctt g                                             201

<210> SEQ ID NO 70
<211> LENGTH: 456
<212> TYPE: DNA
<213> ORGANISM: Zea mays
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t

<400> SEQUENCE: 70
taagctgtac atggacagcc tcaaggagcc cggcgactcg gggaagccct actccgcgcg    60
gtacatnggc agcctcgtcg gcgacttcca ccgcactctn ctctacggag ggatctacgg   120
gtaccccagg gacaagaaga gcaagaacgg caagctgcgg cttctctacg agtgcgcccc   180
catgagcttc atcgtcgagc aggccggtgg caagggctct gacggccacc agagaattct   240
tgacatcaca cctacagagg tatcaaacta cttgatcttg antgtagaac tgtgtccagc   300
tgatagatta accagtttgc gtcgtgcaga tccaccaaag agtgcctctg tacattggga   360

```
gcgtggagga agtggacaag gtggagaaat tcctggcttg aatgccagag cctctctcat    420
cagatggact cccgaagaca tcaagtttag ggagga                              456
```

<210> SEQ ID NO 71
<211> LENGTH: 533
<212> TYPE: DNA
<213> ORGANISM: Zea mays
<220> FEATURE:
<221> NAME/KEY: misc_feature
<222> LOCATION: (323)..(323)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t

<400> SEQUENCE: 71

```
ctcaggatgt tccaaggtct gtgatttgta atgttcatgg agttaacccc aaatttattg     60
agattggcaa attgaaacat cagcagctat gccaaagaga gcaagcattc ttcaagggtg    120
catattatat cggaaagatg gtatggagta aaggttacac agagcttctt cagcttcttc    180
ataagcacca aatggaattg tctggcctta aaatggagtt gtatggcagt ggggaagatg    240
ctgatgaagt aaaggcatca gctgagcgac tgagcttaga tattagagtc tatccaggcc    300
gtgatcatgg agattcaata ttncacgagt gagtatttaa tagatgaaca ataacttttt    360
atacattctt actagctgct agattgtttt atgttcaggt ataatttatg ataagttctt    420
tgtaccatca ctttataatc tttgagtctc gactgaactg tgttattgat tccattgtnt    480
gtcccagcta caaggtcttc ataaacccaa gtacaactga tgtggtatgc aca           533
```

<210> SEQ ID NO 72
<211> LENGTH: 201
<212> TYPE: DNA
<213> ORGANISM: Zea mays
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t

<400> SEQUENCE: 72

```
aaatataatt gcattatata ttaaattaat agtatttaaa tatgaaatan agatcattgt     60
tccatactat gagcaatttt ataacacccc gtccactcct ngaccggcga tacttactcc    120
tgtcagctct ctangaccat atatcatccc cacaggccaa cacgagtctt ttgtgcgcac    180
tttgtcctca ctcatgcnca c                                              201
```

<210> SEQ ID NO 73
<211> LENGTH: 201
<212> TYPE: DNA
<213> ORGANISM: Zea mays
<220> FEATURE:
<221> NAME/KEY: misc_feature
<222> LOCATION: (101)..(101)

<223> OTHER INFORMATION: n is a, c, g, or t

<400> SEQUENCE: 73

```
actccaccta attccatatc ataatagtag tctggtcgag ttataataga ttttcgctgc      60
tctgcctagt tccaaatttc tgacatctta catgtcctat nttgggccaa caaatatatt     120
tacaaatgaa aaatattgc acaagtctac cgtccctcaa cctgaacaag atttgaggac      180
acatggcagc agtcaatgcc t                                                201
```

<210> SEQ ID NO 74
<211> LENGTH: 201
<212> TYPE: DNA
<213> ORGANISM: Zea mays
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 74

```
caggcctact gtgggcctgt cttttgccga acaaatcttt aaaaagcttt actggtataa      60
aaantataat aaaccatggg tccgacgctg acaacatcca ntttattact caatttatgt     120
tcctcatgga cgctgacaaa tacctttcag aacctgtcaa tgtctggctg tttgtgatgt     180
ccngcaaaga acagttctga n                                                201
```

<210> SEQ ID NO 75
<211> LENGTH: 121
<212> TYPE: DNA
<213> ORGANISM: Zea mays
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t

<400> SEQUENCE: 75

```
aactgaatgg atgatcttga gatctagaca acatgcaac catttaatag aataaaataa       60
nnacncgctg acatgcattt ggnctgcagc tattggacat aagaatanga aacaaataaa     120
a                                                                      121
```

<210> SEQ ID NO 76
<211> LENGTH: 121
<212> TYPE: DNA
<213> ORGANISM: Zea mays

```
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t

<400> SEQUENCE: 76
ccggcgcggc cccgccgagc tgctgccgcc gcacaggcag gcccgtggcg acgaggcccg      60
nctccatgtt gcccggggtc ggcggtgcgc ttgggtacat ggtcgggtac tgntgctggt     120
c                                                                    121

<210> SEQ ID NO 77
<211> LENGTH: 121
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 77
ngagngagga attgagattg tttgtgtcgc cttagcaatg cganaaaaat aatcttgatt      60
ngctctaaag gaacgacgcg tagccaacgt agtcatggag tgtttggtgt gatggaccaa    120
a                                                                    121

<210> SEQ ID NO 78
<211> LENGTH: 201
<212> TYPE: DNA
<213> ORGANISM: Zea mays
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t

<400> SEQUENCE: 78
tttataaggc ttggcctnaa tagagtgagc ctcctagttt tcaatgtgtt tctcctanaa      60
ttttatcttt caacgcaagt acatcttcct aagaagtttt ntcactacac atccaaacca    120
catcaacatt gataagtttg aattaccatt tattttgcga acaaatgatt tngaatttca    180
agatgaacaa ttactaagcc a                                              201
```

```
<210> SEQ ID NO 79
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t

<400> SEQUENCE: 79
tccaacaaat ctgcaataga cctagaacgg agttgctcaa cttgtagtat acgaagagaa      60
nttgttattt ccactcatct gatagacgac ngatacctat ctacaagcac ggagcgaaac     120
t                                                                    121

<210> SEQ ID NO 80
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 80
ttagtgagcc acgtgactaa ataaagaaca aagctttata acggcagggc attttaaggc      60
nagtcgagat ttatcagctg gtgacggttc ttcatctgtc ggtgggagct gtcggctgat     120
g                                                                    121

<210> SEQ ID NO 81
<211> LENGTH: 201
<212> TYPE: DNA
<213> ORGANISM: Zea mays
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 81
tccacgaacg ttgattcccg gtaactgaac gggtggncat ttccgtcac gaaaaagcaa       60 gagcaacttt cggatcgttc cgattctctt gcagccaagg nacagggggc gtccggcgac    120
acgcactgcc caaatggcca tcacgtcaac catgcgttcg ttccactact tgcagccttc    180
caccacgatc gcctgcacgg c                                              201

<210> SEQ ID NO 82
<211> LENGTH: 201
<212> TYPE: DNA
<213> ORGANISM: Zea mays
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
```

```
<222> LOCATION: (101)..(101)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t

<400> SEQUENCE: 82
ttgaaaacag tttcggaccn ttttngtcct tgttgatttc aaaagtgtat tctcatcaag      60
aataattatc gccattgtag tccaagagat ccacacacca nacatgctaa gaagtagggc     120
ctctcaactc tcaagtctat ttcngaaaag tattggccac aacaaaaana ncaatagctg     180
attaccaccg aacatgacac c                                               201

<210> SEQ ID NO 83
<211> LENGTH: 201
<212> TYPE: DNA
<213> ORGANISM: Zea mays
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t

<400> SEQUENCE: 83
tatagctgca tgctgcacaa attgcaatgt tnnataggat gctgttattt cttatgtgtg      60
gggcttcttt cttgtcatct gaattatgac ctttctacta nttcagtaca attaactctg     120
atatctatct ttncttgaag agcgctgtca tgctntccat tgaccaccat ggttttgatg     180
tcctcgccaa agtgcctcaa g                                               201

<210> SEQ ID NO 84
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 84
acgcgtacgt ggaggaaatg aggaattaag gaagaacgag gaatgggtgg acgaggagga      60
aggagacgat gtgggactgg atttaaaggt ttgtgtggcc nggaggggtt ctagaatgtt     120
ccggcacgtc acggccgtcg acacgggcac gtcgtgggga acttggatcc attcgtgagg     180
gtggggattc tagagtgtac a                                               201

<210> SEQ ID NO 85
```

```
<211> LENGTH: 201
<212> TYPE: DNA
<213> ORGANISM: Zea mays
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (168)..(169)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 85
ataacaaatt ttattagcag gtgaagtcta ctcaaatant ggcgtgtggg ctcaaactat      60
tcanaagnct aatgaccttt atcttggtag caccggtaca ngatttgaat gtacattcat     120
ggacgaaatc gttgtctcat ctccttccag canctngtag tgacgccnna tgccagctga     180
accttcttgt tggaatnacc a                                               201

<210> SEQ ID NO 86
<211> LENGTH: 714
<212> TYPE: DNA
<213> ORGANISM: Zea mays
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
```

```
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (605)..(607)
<223> OTHER INFORMATION: n is a, c, g, or t
<220> FEATURE:
<221> NAME/KEY: misc_feature
<222> LOCATION: (611)..(614)
<223> OTHER INFORMATION: n is a, c, g, or t
<220> FEATURE:
<221> NAME/KEY: misc_feature
<222> LOCATION: (651)..(660)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (670)..(671)
<223> OTHER INFORMATION: n is a, c, g, or t
<220> FEATURE:
<221> NAME/KEY: misc_feature
<222> LOCATION: (675)..(680)
<223> OTHER INFORMATION: n is a, c, g, or t
<220> FEATURE:
<221> NAME/KEY: misc_feature
<222> LOCATION: (684)..(686)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t
<220> FEATURE:
<221> NAME/KEY: misc_feature
<222> LOCATION: (691)..(695)
<223> OTHER INFORMATION: n is a, c, g, or t
<220> FEATURE:
<221> NAME/KEY: misc_feature
<222> LOCATION: (697)..(705)
<223> OTHER INFORMATION: n is a, c, g, or t
<220> FEATURE:
<221> NAME/KEY: misc_feature
<222> LOCATION: (707)..(710)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t

<400> SEQUENCE: 86
tacnncactt acgatgtngt tntccaggat tcattgtgtt cattgctgtt gtttgggtca      60
tacaagaatt tacatctttc catnttctga aatatgtgat cttattcata ggtgagacag     120
aagatgtcgt acaatcatgt tctctttatt ttaatttctg gaatgcaaat tgtatgcttg     180
aaatttaatc tttatgttta tttatgtgca acaggtgtga tgaacagctt attttcagtt     240
tacggtaaag aaacaaaaaa aanctttttcc ttnttattcc atgntagaat aatccatgtg     300
ttactctcaa tgaaatattn tcaaattata tagatattta tgatgacttg atatcccgaa     360
gagttaacac aagtgatgct gaaaagtttg ctgaaatctg cccttgcccc tgcaatggtt     420
ttgcatgggg tgttatatgg tctgctccaa gtttcgatag ttatattttt ctgtatacct     480
```

```
tgatgntgtg ttaagatnttt cctgatgtaa cgacaccaat gctaacgttt tctgttctttt    540 gtttcagggg attcatctcg tttatctttc tctgcgcttc aatataccttt ggactggtca     600 tattnnnttg nnnngattcc tatgttttca tatcactgca ttttattct nnnnnnnnnn       660 acatgntagn ncacnnnnnn actnnnanac nnnnnannnn nnnnnannnn cnac            714
```

```
<210> SEQ ID NO 87
<211> LENGTH: 121
<212> TYPE: DNA
<213> ORGANISM: Zea mays
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 87
ctacataatt cagctaataa catgtttant gtaagcagct ttctctgtca aaactcaaaa      60
ngtcttgtac tcagtcgggt gattctatgc gaaatatttt cctcatacca gggagcgcca     120
t                                                                    121
```

```
<210> SEQ ID NO 88
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 88 gcttttgag acacctctac ccaattacac atacactttg ttgattaata ttgatgatta       60
ntgatcnatg atgatgcgtg ttaatttgat tagagaataa cccggatctt tcaaggaat      120 t                                                                    121
```

```
<210> SEQ ID NO 89
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t

<400> SEQUENCE: 89
ctcagcaagt tgaagctctc gttttgtacc ttctcgatct taaacgcact cgaaagataa      60
ntttacccag cggcagcgga gaacagggnc gtggcggtga ttggcccatc caccagcact    120
a                                                                    121
```

```
<210> SEQ ID NO 90
<211> LENGTH: 682
<212> TYPE: DNA
<213> ORGANISM: Zea mays
```

```
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (559)..(561)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (591)..(593)
<223> OTHER INFORMATION: n is a, c, g, or t
<220> FEATURE:
<221> NAME/KEY: misc_feature
<222> LOCATION: (596)..(599)
<223> OTHER INFORMATION: n is a, c, g, or t
<220> FEATURE:
<221> NAME/KEY: misc_feature
<222> LOCATION: (601)..(601)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (660)..(661)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (669)..(670)
<223> OTHER INFORMATION: n is a, c, g, or t
<220> FEATURE:
<221> NAME/KEY: misc_feature
<222> LOCATION: (679)..(680)
<223> OTHER INFORMATION: n is a, c, g, or t

<400> SEQUENCE: 90
caaagcgaca agcccctgtc ttgagatgaa anggacaatg ggccttatcc taaagaaata      60
aaagaaacag aaaaaggtaa aatgtnaagt agagaacaag ttgtatttta tttctgttgt     120
aacagaataa atatataggg catttctgtc ctaatagata gagaacaatg gagcatgcct     180
gttctgttcc aaaattcgga gtctcttgag caactttgtc aagtacttct tgagcagaca     240
aagaaggttc tctcctatga gcagccaaag caacagactg tggtgggagc ggatttgatg     300
taggtctatc ttcctacaag acatttagag taacctttat cggcagtatg ttcaaaaaaa     360
ttgccccaca agcagccata aggaatagaa ccaacagaaa tttataacaa atagaatgtg     420
acctcctgaa tttgcagctt ttccttggac cctttggta  ctttaacctt tttcttcttc     480
acaatgatct catttccttt ccatataatt tctgctggnc catcttcaac atattcccat     540
tcactatctt cttctgacnn ntttccttgg ncatctttag gctgcaagag nnnagnnnna     600
nttgtaacca gatcactatt ttagnatgtt tctacaactt attttgaaa  acatgaactn     660 ntnaatttnn agtgatggnn ta                                              682
```

-continued

```
<210> SEQ ID NO 91
<211> LENGTH: 1131
<212> TYPE: DNA
<213> ORGANISM: Zea mays
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t

<400> SEQUENCE: 91
tcttttcttc gtttgattat tagtcgncac cagcnctggn nagacgctga accacgacag      60
cgccccaggg ttcgtcctcc cgctggaata gtaagtgacc ggagaaaagc agcacaagag     120
agatgtggta nctatgcgtc ttctaccaca ggctcctgga ctaccggcga ccggaggtgg     180
agtccctcgc cgagctcttt gccggcccag gcgcccgtga atccgtcgag tggcgcatgc     240
cggagaacca ccacgtagac tccccttcc acctcgttcg cctccctgga gacgagcgcc      300
tcgccgctca ggtcgccaac cgcagcttgt tggtgaaggg ggtctacgag ctctggggct     360
atggcactac ctacgaggag ctggagaagt cggtcaggga gtaccccgac gagaggaagc     420
ttccgttcct ggtcccggaa agcagcttca agatcgttat cgacagcttc ggcaaggtga     480
tcagctccca agagcagaac gagatcatac agagcctcac ttacatacca ttcaagggac     540
gtgttaattt gaagaagcct gatcacagat tctttgtcat ggagaccgat gactatgggt     600
cgaacaatgg tctcccaccg gttgtcaaga ggtcgatatt ctttggccgg gaggttggag     660
cagctgatag gcatctcctg ccaacatacc agctcaagag taggaagtac attggcccca     720
ctgcaatgga tgctgaaatg gctttcctca tggccaatca gggtctggcc tcgcctggga     780
agcttgtcta tgaccctttt gttgggaccg ggagcatttt ggttcagct gcacattttg      840 gagctatgac gatgggtgca gatatcgata taagggttgt acgggatggt cgtggccccg     900
attgcaacgt ttggagcaac tttgagcagt ataagttacc agagcctttg tgtttgctaa     960
gggcagacaa caatctccca ccctggcgtc ctggattgaa ggagatgttc gatgcaataa    1020
tttgtgaccc accatatgga gtccgggccg gtggccggaa gtctggtggc cggaagctca    1080
taaaaggcgt caaaggcccct tacacagtgc ctgatgagaa acgggacaat c            1131

<210> SEQ ID NO 92
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
```

<400> SEQUENCE: 92
gtagccaagg aaaacttggg gtaagagtta tcttgagcag tagattaaaa aaattcaaat      60
ngttccaagt agtcagttat ttatactcat gtcttcttat naaggcttac aagcttaaag     120
t                                                                    121

<210> SEQ ID NO 93
<211> LENGTH: 201
<212> TYPE: DNA
<213> ORGANISM: Zea mays
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 93
acgtgtgcgt cganaactcg aggggcctgt ggatattgct nctttacaaa aactttttt       60 tttattctgn gttcgaaggg agaaaaagga cctccatgtg nctggatttc tttacaggaa     120
ctcaggaagc agatacgccc tttttttgcac aatggaattt ggcagacctg ttgacattga   180
agcattcaag natggcttna c                                              201

<210> SEQ ID NO 94
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t

<400> SEQUENCE: 94
cttgataggc acaaacctcc aggccaacat ctaaggggc caatctggag gtaaaaaaat       60
taaatatagg tcaagcaagt ggaaagaaaa aatatacaaa nagcaattaa ccaaaactcc    120

```
aaaaccatca cctgcccatg gtgttaaccc tcctatccta ccccnccnga nagaggncac    180
tctaccacct ttccttcttc c                                             201
```

<210> SEQ ID NO 95
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t

<400> SEQUENCE: 95

```
tgcgcagccg gtccgccacc tccgactgct cgtcgtactc gtcgatcacc tgcaccatcc    60
gcggcgcggc attaccccca aatcaaccac gcgtgttgcg ntgcatcccg attatatgct    120
gcacacagca atagcctgtg agtgtgtacg gacgttgtgc ttgaggaana cgacgggngc    180
gccgtcgtcg ccggancccct t                                            201
```

<210> SEQ ID NO 96
<211> LENGTH: 201
<212> TYPE: DNA
<213> ORGANISM: Zea mays
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 96

```
aaggagcaaa gagttgccat gagaatgggg aagagacgtg catcaggaga aancaatctt    60
actcctcttt gcttgcatcg aaccgatgat cagaggatag ntgataaatt gaaccttcag    120
cttgtagtac acaacgggaa tcaccaactg atgcaacagt gatgaccaat ccatctatta    180
tgacaaatgt cacagttgtc c                                             201
```

<210> SEQ ID NO 97
<211> LENGTH: 121
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:

```
<221> NAME/KEY: misc_feature
<222> LOCATION: (84)..(84)
<223> OTHER INFORMATION: n is a, c, g, or t

<400> SEQUENCE: 97 nttttttct aataaaaaca gaaggtacat aaataagttg gataatttct ggagtgatct      60
ntgcaancaa gtaatggtga ttanaatatg tacctttact tcctctagtt tcggtttgtt    120
t                                                                    121

<210> SEQ ID NO 98
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 98
cgccgtcacg gccgtcacat gggtacgcgt acgtcgttgc ttgcaagcgg gttttttttc    60
tagtttgact ccatctgacc tatgtgggtc tctctggacg ncggatatga tgtgcatatg    120
cagctctcgt ggttcccctt cttccagtac aacaccgact ggatgggccg ggagatcttc    180
cacggcgagc cgcagggcnc g                                              201

<210> SEQ ID NO 99
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t

<400> SEQUENCE: 99
atggtctaac tagtctaaat acttcacgaa ggaccttcac taatcaccat atgtatcacc    60
nagcttaata caantggaga gcattataat agagcacaaa cttttttttta gtatgtttct   120 c                                                                    121

<210> SEQ ID NO 100
<211> LENGTH: 201
<212> TYPE: DNA
<213> ORGANISM: Zea mays
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 100
aagataaaga acgttaaatt ctgtcgaagt aaatccgtgc agtttatgga actgctcgcc    60
tctactacga tttatttccn tctttattt cctagcttta nggtcttaat taccaagatt    120
```

```
tatcttcaag ggataagatg agaaagttat taatcaccaa gagatccgtt ttcacacgtc      180
cggccagtca tcttcttcct c                                                201

<210> SEQ ID NO 101
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 101
tctctctctc tgagtatgtc aaaaaatggt acttcccaaa atatatctac aagctaatta      60
aagagtaaac tatagaacat tgtgttattt ctcgaattca ntgataaagt tcaggtccaa     120
tggtcttatc ccatgcatcc atttctaatt tatcatttgg agttgaggtt gaccaaatca     180
catcccatta tattctccta g                                                201

<210> SEQ ID NO 102
<211> LENGTH: 712
<212> TYPE: DNA
<213> ORGANISM: Zea mays
<220> FEATURE:
<221> NAME/KEY: misc_feature
<222> LOCATION: (265)..(289)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (541)..(606)
<223> OTHER INFORMATION: n is a, c, g, or t

<400> SEQUENCE: 102
ggccgggtga ggaatgcact tggtagatac tacctgaata acttcgttga tgggactaag      60
gcgaggtcat atggcctctt ccaaggacat tacatgacat ctgttagtag agatatggca     120
gtgccaagca aagcaggact tctgcagagt tatgcgtcct tccgccttgc ttttgcattg     180
gttatgggag ctctaatgtt catgttgatg tcactgagac aggcccggaa tgatgttcgt     240
catttgttgc tgtcacttat gtggnnnnnn nnnnnnnnnn nnnnnnnnna ttttgttaga     300
gccaatggtc gcacgttcac taaccaacct aggtttcaca agtcacgcca ttgatggttg     360
caagatgacc aatttgctcg tcaagcggcc tcatagatta tcatcatcca tcaaacttgt     420
tgacacagat tggttnacat gaagtgttgc gttttttgg cacggtattt accctttgt       480 aataaggttt cttccatttt gtaacaagtt tttgtttcct cgtcgcctac ttttgcttca     540
nnnnnnnnnn nnnnnnnnnn nnnnnnnnnn nnnnnnnnn nnnnnnnnn nnnnnnnnn        600 nnnnncaca tattattgta ttatgatttg ttcatgctac aaacgaagtg aatacgcctt     660
ttgtgatttg ttcatttgta ataaaaagtt tgaatactcc ttttgtgcac tc             712

<210> SEQ ID NO 103
<211> LENGTH: 121
<212> TYPE: DNA
<213> ORGANISM: Zea mays
<220> FEATURE:
<221> NAME/KEY: misc_feature
<222> LOCATION: (15)..(15)
<223> OTHER INFORMATION: n is a, c, g, or t
<220> FEATURE:
```

```
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 103
ttagggattt tcctntaaat aantnttaaa caagtagtaa actatttctt gtaggtaatg    60
nttttattcg aacaataaat aaatatacaa agtggatacg gatttcgtca tccatgatat   120
a                                                                  121

<210> SEQ ID NO 104
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t

<400> SEQUENCE: 104 ttgttttttca agaacacgtt tgagtgtctt agtttttttt tttacaaaaa aattgacttc    60
tttcggttac ctggcaaatt accatcacga tggcaccgat ngcgaacgtc acctcccggc   120
cgaactgttt cnctgagant gcagatccaa gaactccgca ggaggtcacc agaaccagca   180
gaacgttgcc gatcaccgct g                                            201

<210> SEQ ID NO 105
<211> LENGTH: 372
<212> TYPE: DNA
<213> ORGANISM: Zea mays
<220> FEATURE:
<221> NAME/KEY: misc_feature
<222> LOCATION: (321)..(321)
<223> OTHER INFORMATION: n is a, c, g, or t

<400> SEQUENCE: 105
caaggaggag tacgacgctg aggtggagga cgacgatgca gacaacgtcg aggagtctga    60
cggcgacgac ttcgaccagg agaccggttg acccaggtgg ctcccccgtg cttcgtcggc   120
gtccttgagc gtcgtcatcc ccgctgtcca gtctgtattt cgcaatccct gagttgttcc   180
ttctatctag atacgctgtt accctattct gctgctgtct gttctcagga tctgagcatg   240
tccttgtcgt gtggaccttg tgtatgaaac aggtacatga ttaatcggtc caatttaaat   300
gctatattag tttcctctat ntgtgccaga tactgctact tcttaccatt tgttgtttg   360 tgtcatgacc ag                                                     372

<210> SEQ ID NO 106
<211> LENGTH: 387
<212> TYPE: DNA
<213> ORGANISM: Zea mays
```

```
<220> FEATURE:
<221> NAME/KEY: misc_feature
<222> LOCATION: (160)..(160)
<223> OTHER INFORMATION: n is a, c, g, or t

<400> SEQUENCE: 106
ggccctatgc tccaagaaat gcaaccgcgt tgatctcctc cgcagaacgt ttctgtagcc      60
aagggtagct ctgcaaacgc gtccgcttgg gttttctgcg tcgtaggctc gtagccctaa    120
tcatgctgtc cgctgtgcaa gtgtacatgt atgttcgcan ctgggtcttc tcggctgcgg   180
acaggcggtg cgtagtagat tggctttgtt gtaggcttaa cgccattttt gtgtgtgtgg    240
ctgtgtgcac atggcaaaaa caaacaaaca aaaatgttta tgcaccggag cagattctat    300
ttctactcca ctctcgtaaa atagttgact ttataggatt caaattttgt tctaaattaa    360
tggttattct cacctctcaa tgcaaaa                                        387

<210> SEQ ID NO 107
<211> LENGTH: 201
<212> TYPE: DNA
<213> ORGANISM: Zea mays
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 107
tgttnttnca atgcttgata aancattcat tttagtttgt agcncnngaa acttangtct      60
atgtttatgg gcagaanctg gtgatgcaaa atgtggatca ngctgcagga gatttcattg    120
accttttgca agggctgctg aagtatgatc catcaagccg tttaacagca cgagaggccc    180
tgaggcatcc cttcttnacc c                                              201

<210> SEQ ID NO 108
<211> LENGTH: 201
<212> TYPE: DNA
<213> ORGANISM: Zea mays
<220> FEATURE:
```

```
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t

<400> SEQUENCE: 108
ccgaaacaag aaatgtagat gaaagctctc ttgtgggttt tagtgttttg gataacaaca    60
catttaaatg nctnacatgg tgttaagtgt tgagcagata ngtagtgcaa agcttgtaaa   120
gctcaacata agagaagaaa aaggatggat attgattaag tgaaaatcaa tgaacatgac   180
ttaggtacaa ctgattgaan t                                             201

<210> SEQ ID NO 109
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t

<400> SEQUENCE: 109
tgccgcggct ccgtcgactt aacctgtctt acaatgagac actgaacgac aaggtgatcg    60
gcgccatgct ttcatcctgc cggaatctca tcgacatcag nctcaggggg tgccggggcc   120
tgacgggagg ctcgctnctc tcgctgctta ggcactgtgg gcagtcactg gagatccttg   180
acatctcccg ctgtccgggc a                                             201

<210> SEQ ID NO 110
<211> LENGTH: 121
<212> TYPE: DNA
<213> ORGANISM: Zea mays
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 110
gcctgccttt gccgtgcctt gtggacctcg tcgtctcgtg ctgcgtgncg cagctgtcag    60
ntgtgcgagt ggaaaaaaaa tcctctctgg aacgaccacc ggcagcaagt gagtcttaat   120
t                                                                   121

<210> SEQ ID NO 111
<211> LENGTH: 121
<212> TYPE: DNA
<213> ORGANISM: Zea mays
<220> FEATURE:
<221> NAME/KEY: misc_feature
```

<222> LOCATION: (7)..(7)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t

<400> SEQUENCE: 111
taaagtntat atatagtcaa gctcaaacaa tagagcgaac aaggaagacc agaagatagg    60
ncacctgagt agatgtggga gatnagaana ccaatatcct tcccaatatc aaacatgnaa   120
c                                                                  121

<210> SEQ ID NO 112
<211> LENGTH: 121
<212> TYPE: DNA
<213> ORGANISM: Zea mays
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 112
gtgtaatata cactaatttc actttcaatc ccttnaatac acntcaacct acttcaatnt    60
ntctttaccc aaacaaagcc ttaaggtgat gtttagtttt tagtgactaa tttttaattt   120
c                                                                  121

<210> SEQ ID NO 113
<211> LENGTH: 121
<212> TYPE: DNA
<213> ORGANISM: Zea mays
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:

```
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 113
ccggccttgg cgtcgaagat gctcgacctn gntgagtnga nacagccnag tgacaaaatg      60
natcagaata tgtccaaaca aattccacaa acgacacaat cagaactcaa acataagcgt     120
g                                                                    121

<210> SEQ ID NO 114
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t

<400> SEQUENCE: 114
gtacgcgggg cacaacgtgg tgctggagat ccaggccacc atcccgtcca cgccggagag      60
nccgtccaag aagcccatgt ggaagggcgc cntcgtcgcc tacgccatcg tcgccgcgtg     120
c                                                                    121

<210> SEQ ID NO 115
<211> LENGTH: 121
<212> TYPE: DNA
<213> ORGANISM: Zea mays
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 115
ccttcagcag aatgcacacn tgtgtcttct tnacatggcc aactctctct ctctctctct      60
ntgttccatt ccatgctgtt ttccagatct gcatcgtcct aggtgttctg ctgatggtac     120
t                                                                    121

<210> SEQ ID NO 116
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 116
catgttcagg ttaatttctc caagtcaact atggttgcgg aggatcgttg tcttcttatg      60
atataattat ttagctattt tgtacaacac tcttattata nagtaaagat gcgacattcc     120
```
tttcggtatc atgagtcatc gatcatatgt gtgagacttg atcctatcac acatttgatt    180
cgcgcccggg tttacccttta a                                              201

<210> SEQ ID NO 117
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 117
tgttatttgt acagctgaag tctaacttta ttgcataaca tgttctaact ttagagggtg    60
caactaggac aacagctgct cctgcaccga aggtctccca ntatccgaca caaaataccg    120
tccaagcttt agcatctttt gtcacttctt caccctaagc ccctagcgtc caatcagcaa    180
tgaagtctgc taacgcctga g                                               201

<210> SEQ ID NO 118
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 118
gcaacaggac gatgccggtg tggctggact gggccatcag ggacaaccag acccagacgt    60
gcgaggaggc caagaagggg caggggcaca actatgcctg ngtcagctcc aacagtgact    120
gttacaactc taccaatgga cctggctacg tctgcaactg tagcatgggc tacgatggca    180
atccatatgt taccaatgga t                                              201

<210> SEQ ID NO 119
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 119
gcgacctcag ctacatggac ccggagtacc ttcggtctgg catactgacc aacaagagtg    60
atgtgtacag ctttggagtt gtgctcctgg agctcatcac naggaagaag gcctccgctt    120
ctgacaacaa tggcctgctc aagaacttcc ttgacgctta caccaaggac aacaggttgg    180
tcactgagct ggttgatgcg g                                              201

<210> SEQ ID NO 120
<211> LENGTH: 201
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:

```
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t

<400> SEQUENCE: 120
ataggagggc acactcatcg acccnttag caaggagagg aatatctttt ctcaacaacg    60
ctccatcacg tggggtatcc cacagacttc agcattagtc ntctccaaag ctgcgctagc   120
cntgcccaaa tcnctnagaa ggctatccgc catctgccnc ggaggggtcg ncnaggtgga   180
tggctgggac atggggccat g                                            201

<210> SEQ ID NO 121
<211> LENGTH: 201
<212> TYPE: DNA
<213> ORGANISM: Zea mays
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t

<400> SEQUENCE: 121
caaacgagtc gatncgagcc gagctgacca tgaaccgagc gagacaacga actacgaaca    60
ttttgtccag ccctacccct agttcgtacc cgtggaacgt ngagagagcc tcaaaacttt   120
gcntctttaa gactttagat gtacgatttg aagtgtttgg atattttat aactacttt    180 ttcttcttct atttatgtgt t                                            201

<210> SEQ ID NO 122
<211> LENGTH: 121
<212> TYPE: DNA
<213> ORGANISM: Zea mays
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
```

<220> FEATURE:
<221> NAME/KEY: misc_feature
<222> LOCATION: (61)..(61)
<223> OTHER INFORMATION: n is a, c, g, or t

<400> SEQUENCE: 122
ttttagagtt ttcanattca gtttgaattt ntantttttt atgactttgt caaattagat        60
ncatcaatac aaaattacca gcatagtgga catttgttgt gtttgtttaa ttgttaattg       120
c                                                                      121

<210> SEQ ID NO 123
<211> LENGTH: 201
<212> TYPE: DNA
<213> ORGANISM: Zea mays
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 123
gagaagaaga agaagaagaa gangaattca gaagctagat atatatgaag gagtacacga        60
tcgaaggagg tagctagcta gtagggaggc tggagcgcac nttgtgaatc ccgagttgat       120
cgagcccaac ctggcgggca cgtactacgt acgcttacat tagctgctac tagctaagac       180
gacagtttgg tagctaggca g                                                 201

<210> SEQ ID NO 124
<211> LENGTH: 689
<212> TYPE: DNA
<213> ORGANISM: Zea mays
<220> FEATURE:
<221> NAME/KEY: misc_feature
<222> LOCATION: (393)..(393)
<223> OTHER INFORMATION: n is a, c, g, or t

<400> SEQUENCE: 124
tgcttgctac cacgcctcct catctgctgc caccggcgtc tctccttccc agctggggcc        60
ctgagctgag agcagagcag ggagcgaaac tttgcgctga gattgagctg ctcctctact       120
tactactact agaaggcggc ggcgtcggcg tcggcgtcgg caatgggtc ggagacgttc        180 gtggagatcc tgctggccat cctgctgccg ccggtcggcg tcttcctccg ctacggcatc       240
ggggtaatta acactcagct tagcatctga ttaattgatg catcgtcgtt ctcatcagat       300
gtgtgtaagt aaagtaactg cttgctcgcg atctactgtg tgcctgccct gcaggttgag       360
ttctggatct gcctgctgct caccatcctg ggntacatcc cgggcatcat ctacgccgtc       420
tacgtcctcg tcgcgtgaca gcacaacatg gtgtggtagg tatgacgacg atggtgaccg       480
tccgcccgcc cgccgggagc tggaatatat gagacccaga cccagtgctt ctgatccatc       540
cattccatgc atgcagtgat gcaggcatac gtacgtttag cccatgctgt atgtttgtgt       600
cttgctttag ttagctttag ctagctgctt gcagcttagc ttctctcagc tcgtctaccg       660
atccgttttg ctgtgcccat ggacatgga                                         689

<210> SEQ ID NO 125
<211> LENGTH: 121
<212> TYPE: DNA
<213> ORGANISM: Zea mays
<220> FEATURE:

```
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 125
cataatagaa ataagcagtc cacatgcaca aaccacacan cctacatgaa ctttatcact      60
naacaactta agaaacgaag acgtatatgg tggattgctt ttaagtaaaa ccgttgcaac     120
t                                                                    121

<210> SEQ ID NO 126
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t

<400> SEQUENCE: 126
agagacagag aggggggggg ggggggggct cggggagct aaccttggtt ttgaagtctg       60
catgacgaga ttcctcaccg aatccttctg cagtcaccaa nctgctggtt caaacggaaa    120
agnagtgata agtgagtaca aaatcgcaca gaagctttct tctttctttc atgtgcaagc    180
aaaagcatgg ctagtnactg t                                              201

<210> SEQ ID NO 127
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 127
aggatcgatg gcaagagaga gagagacagc gcgctatatg gctactcgct acttttgcag     60
gagcatgacg tcgtcgtcgt tgcctcttgg ctcttgctac naccatgcat gctagagtct    120
gcatgcgcag cagccagtgc tgctgttgct gtacatggat cgtattcccg agacccagag    180
acagacgtct agaaagaaaa c                                              201

<210> SEQ ID NO 128
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 128
tccattgtta ggagtgtcaa cttttgagtt ttgcaacgtt cgcttgtaga cctatgtggg     60
gttggtgctt catcaacaga ttgtacaaca tcttgtacaa nttcagtggt gtttcagaag    120
```

```
gcttttttat tcacaacta ctaattgtag tggattaatc tatagatcta tgagaaaaat    180
aaatgtctat ttagtttagt a                                            201
```

<210> SEQ ID NO 129
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t

<400> SEQUENCE: 129

```
ccaatctagt caaattgatc gatttatgtt gtacacatct cgaatggatc tcttgattcg    60
atatatttaa aatcaaattg gagcaccata tgtcaaataa ngagtaaagt acacaaacgg   120
tccacgaact tagcacgcta tgtctgttac ccccgaacta agaaaatcng acaaatgggt   180
cctcagactt tctcagccta t                                            201
```

<210> SEQ ID NO 130
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t

<400> SEQUENCE: 130

```
ccaatatcat acgtctatct gacatatgca tgtgtccatt gccattcttc atgtttgttg    60 acctttagg tgtgggacca aagccttcag cggaacccat ntctatacag cggtacaaag   120
tttcgggtat gtattttag ctctaccttg gtatgctcgt tttttctgc tccgttgata    180 cttgaagtcn tgaagatgct a                                            201
```

<210> SEQ ID NO 131
<211> LENGTH: 201
<212> TYPE: DNA
<213> ORGANISM: Zea mays
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 131

```
agtttagcac tacaaccaca aatatttcag tttaggacta caaccacaaa tagaatccta    60
agagttattt tttttnttcc ttggggtcag tttcttttga nctgtcttct tggttggcgt   120
tgttatcttg gttggagttg aagtaggcat agtggtctga gaagaattgc tttctaacag   180
agcagcaagt cgcctgcaca a                                            201
```

<210> SEQ ID NO 132

-continued

```
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 132
ggaagcttct tgcatgttaa gtgatttggt gcatgcttta tagaaagaca atctctctgt      60
atatgtatct gttctactgc attcaccagc aggtagtaga ntgtaaatac tgacaacaat     120
caagaatttc agtatggagg aaatgccttg cactacaaag atgactcaga tcatgatctt    180
gagtactgtg tctcacttca t                                                201

<210> SEQ ID NO 133
<211> LENGTH: 201
<212> TYPE: DNA
<213> ORGANISM: Zea mays
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 133
acaaactcac acagaagtag agagaggatt acgacggcat caatcaatac atggcaggtc      60
gttntngcat ctccattagt tcctataaaa tgctccctaa nctcagatta tacgatgaac    120
aaaaaataac tctagccttc aacggttcct aattcttagg ttgttaaata ttttaaatc    180 atgctaactc agtttttata g                                                201

<210> SEQ ID NO 134
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 134
agcgacgccg ccgacgccga cgccatcgac gacgcgtcct cagatgtatg ctttgtgacc      60
nctgncaaat gtgggacctg atgcatcatc gnccattttg ngctcacttg actgttcact    120
c                                                                      121

<210> SEQ ID NO 135
<211> LENGTH: 201
```

```
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t

<400> SEQUENCE: 135
ntgttttaat acgtatgcan cttacccttt ctctgtggga tttacattac gtactattcc      60
aggttgcaac agctagtcag ttctttatat cctacaccat ncgaacattt ggggctctca    120
catttgctac cataatgaca actagacagg tggatatggg catcctcagt gtgatanttc    180
tcgcatacat aatattcaac c                                              201

<210> SEQ ID NO 136
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t

<400> SEQUENCE: 136
ggtcgagggt ggtgttccaa aatcccaagg accatatatg ctatgcccca gcggcctagc     60
ttaataccaa cttaacaaaa cctaacacca gcccaatatc nacccactat agcaatgaaa   120
ccgtatactt ctgctctaga cncacatagg agccatagag ctcacgaggc agaagcacca   180
ccgnccaacc aaggacccttt g                                             201

<210> SEQ ID NO 137
<211> LENGTH: 121
<212> TYPE: DNA
<213> ORGANISM: Zea mays
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
```

<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 137
cnctatagat gtgccacgtc tttcgaagtt tcattagctt cccgcgatgt ttgcgcacga      60
ntgcatgcat gggacncntc ttcngatatc accttgactc ggcgcnttgc cgctttagtc     120
g                                                                    121

<210> SEQ ID NO 138
<211> LENGTH: 201
<212> TYPE: DNA
<213> ORGANISM: Zea mays
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (157)..(158)
<223> OTHER INFORMATION: n is a, c, g, or t

<400> SEQUENCE: 138
tgcagcagga tacttgtgct ggctgcttgc ttggcagggc agcngcatca ctgtcccggc      60
cgttgtctgt cctggcttgg caatgaagca gcagagcaca naaagtcaga aagtggcatc     120
cccatggaat ttacctgccg tctttcagtg aagtttnncg tctccttccg actgcttgtc     180
tgcgagctgg atttgcagct g                                              201

<210> SEQ ID NO 139
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t

<400> SEQUENCE: 139
aaagcatatt catttggtgc tggtagatct ggtagcatag catacctcca tctccatatc      60
aactggtgca aactttccca tggaagatta cttttagcag ntcctaacca tagtccatta    120
ttcctgacag taaccatgca ccaggatata ctagaacaga gctttagcat tgggtttatg    180
gaatgatgca tcngaacaaa c                                              201

<210> SEQ ID NO 140
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature

```
<222> LOCATION: (172)..(172)
<223> OTHER INFORMATION: n is a, c, g, or t

<400> SEQUENCE: 140
cgggcctatt tagtttgtag ctaactgtac cacatctgtt tggttttcta cctaaggtgc      60
cacagattgt ctaagcttag tcgctcgaat tgaagagatt ntctaagctt agtcgctcga     120
attgaagaac taagcttaga cagaaaagtt aggcacgttg tggtgcctta gncaccaaac    180
aaacaaacct tagacagaaa a                                               201

<210> SEQ ID NO 141
<211> LENGTH: 201
<212> TYPE: DNA
<213> ORGANISM: Zea mays
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t

<400> SEQUENCE: 141
cgacgcgctc atcatcctca ccagcgcggt cccgaagatg taggtttgat cctaccngag      60
ggtgccctga tttaattttg aagaagggag ttatcttgag naggtggctg aaattctttg     120
atatattgct tacattgcag tagctgtgtc agttcctgat tttatttgga gttaattntc    180
tgtttcaact ttcaaggtgg a                                               201

<210> SEQ ID NO 142
<211> LENGTH: 201
<212> TYPE: DNA
<213> ORGANISM: Zea mays
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t

<400> SEQUENCE: 142
ggaacaggaa gatatacgat cgagtcaatc aataataaat aaaaagctga agntttcaat      60
tcgtcgttca anctgcgcag ctagtatata ctagcagcag ncgatgagta tatagtatca     120
gtgtgacgtt ggatcaggat agcaagcaag ccctaggtag agantattct cttcttttga    180
gctatattag tcctgtcgca g                                               201

<210> SEQ ID NO 143
<211> LENGTH: 201
<212> TYPE: DNA
<213> ORGANISM: Zea mays
<220> FEATURE:
```

```
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 143
ccctgtcacc cacgtcagca cccacaaaat ttaatgantt ttccattttc gaatatttta      60
atggccatca tgtaaantct atctacgacg tagtcttcct ngtacgaagt ccgatacaat     120
cggttgttcc ctctaaattc atctgaactc aaacaactct atatatttta tatatcctca     180
tattagtttt atatgtttag a                                               201

<210> SEQ ID NO 144
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 144
tgttgtctgg tcactggcgc ttaagaaaga gactgggatt tcttgttgtg ctgattatga      60
gcttttcttg ttgatgcaat taagaaaatt atttagtgct nctcttggac tttgcttctt     120
gtcatctttc tctctgaaca tgtttctgta tggatgggtt acatttcttg tggatcttct     180
tggatttctg atttattaaa a                                               201

<210> SEQ ID NO 145
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t

<400> SEQUENCE: 145
ctagttagtc cacgtggttt gtgttggatg tcaaccacca aaatcgatta tagaaaatga      60
ttaagtccat ttcccttca gctacatagg tgacagtgag ngctgtgtga agcgtgaccc     120
atcggggcan cggtccactt cggcacccct caaaaggcac gtntgtcatt gtaattagtg     180
ggtgaaccgt aggtgtgcgt a                                               201

<210> SEQ ID NO 146
<211> LENGTH: 201
<212> TYPE: DNA
<213> ORGANISM: Zea mays
<220> FEATURE:
<221> NAME/KEY: misc_feature
<222> LOCATION: (19)..(19)
<223> OTHER INFORMATION: n is a, c, g, or t
```

<220> FEATURE:
<221> NAME/KEY: misc_feature
<222> LOCATION: (101)..(101)
<223> OTHER INFORMATION: n is a, c, g, or t

<400> SEQUENCE: 146
gagagagaga gagagagana gagatgagca ggggagggcc agggaagaag aggagagggt    60
cgtcgtgggt tagtagggct cccttggcct tcgagaaagc naaggcaaag caaagcaacc   120
cccaaaggca agcagcgcaa agcagagaga atctgattcc ctccgagctg agtaacatgc   180
gcgtaccaag atcgatcaaa g                                             201

<210> SEQ ID NO 147
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 147
ccatataatc tttgaacttt tccttgtata aactcaatac accatcgaaa tgataaagag    60
nccatttgca tgagaattca gaagtcaata aatacatata tattggtgtt tgtaatttat   120
a                                                                    121

<210> SEQ ID NO 148
<211> LENGTH: 1170
<212> TYPE: DNA
<213> ORGANISM: Zea mays
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (210)..(212)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:

```
<221> NAME/KEY: misc_feature
<222> LOCATION: (1165)..(1169)
<223> OTHER INFORMATION: n is a, c, g, or t

<400> SEQUENCE: 148
ttgcacaaga tatctcgagc tagattacac aaactttaaa ctnctcctat cttattagaa      60
accaaacttt tcttttttat anactactcg tatataaaag tagagtgcag gtcatcagtt     120
tggagacgca gagctgcant atggccagct tctccttgaa accacagcac aatggcagca     180
gcagcangat ctaccatact atctgtagtn nnactgcctc cgaatggagg tcgctcctgc     240
ggtccngaag cagtgtttca tggagctgga agaagcacac aaggttgcga ttgcgatgct     300
gtcagggttc cnanggggt gatgacagcc gtctgagcca aaacaccggc attttccacc      360
catcgatatg gggggatttc ttccttggtt gctctagcag ccctgaagaa gctgctgctt     420
cgtcccaaca aaaggttcat ttcatctatc tctctattct atatatggac ngatcgacca     480
cttatttcct gtcgtcccac tatattaggc ttggatggaa cgatgcgatg aactgaagga     540
agaagtgggt cgtctgatgg tagtagaagc aaactcacca ttgcatgaga ggctgcattt     600
catagacgcg ctggagagcc tgtgcttgga ccacctgctg aaagaagaga tcggtgctgc     660
nctgacgcag atcgagaccg ccggtgtcag tgacgactgc gacattggga cggtctctct     720
ctggttttac ttgctccgga aacaccgccg cagggcgtcg ccaggtaaat aatctcagcc     780
aaaaaaacac gcacttgagg ttcgtgaggt tcaaattaaa gacgccattg ctgcatgcat     840
gcatgcagat gtgttcgtga ggttcagaga cgcggaggga ggtttccagg cgaacgatcc     900
tggggaccta ctgaggctct acaacgctgc gcatttcagg acccatgggg agacaatact     960
cgatgaagcc atcgcgttcg cgagaagccg tctggagatg atgctgccct acgtgaaagg    1020
gccattgttg gcgcatgaag tcagatcctc gctggagatc ccgctgccta gaagggtcag    1080
gatctacgag tcaaagtatt acatccatgc gtatgagaca agtggaacgc tgcatgagaa    1140
ggtactgcaa cttgccaagc tgaannnnna                                     1170

<210> SEQ ID NO 149
<211> LENGTH: 201
<212> TYPE: DNA
<213> ORGANISM: Zea mays
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 149
gtaatttgta gaatggcatt cctttctcnc ctagtcttga tatgaatctg ctcagcgctg      60
ccatgcacct agtgagcctt tgcactttt tctgtgaccg nggcgtttcc attttcatga     120
tgacctcaat cttctctgga tttgcttcta ttccccgatg gctgacaatg aactcgagta     180
actttccggc tagtactccg a                                              201

<210> SEQ ID NO 150
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
```

<400> SEQUENCE: 150

```
atggtaacgg ttattggagc agtccttggc tttttcattg ggatttcatt cccttcggtc      60
agcataacaa aggtattaat gatagtaacc tccacgtaac ngcaataacc caactaattg     120
agcagttact tatgtctgtt tcgaatacgc cagcttcact ttccagatag ctttatttcg     180
tacattgaag acaaagacgc t                                               201
```

<210> SEQ ID NO 151
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 151

```
agggcgccat gggaaggggt acgttgattg cctgaaaact tgacgtagag cgctcttgtt      60
ttgactttg aggaaggatg gtgcttatgt ttctgagcag nttgtcatct tgttgtccat     120
gggagcttat ggcatcttgt taatctgtgg tttaggtgag ggcgcggtgc aggaaggaat     180
ggggcatgtt ccagaccagg a                                               201
```

<210> SEQ ID NO 152
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 152

```
agctgctgca tgggcattgc ttggaagcaa agccaaggcg cgcacctgcg caaaagggga      60
atgatgccaa ggcttgaagc tttggtctgc ttgcttctga ntctgagact tggattccaa    120
gcatgcatgc ccagcatgcc actctctccg ctccacctga aaggaccatg cttggcaggc    180
tttgctacat ggagtaaaac a                                              201
```

<210> SEQ ID NO 153
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t

<400> SEQUENCE: 153

```
gccgttggat tcgggacgg acgggcccga tctgcccggg ggctttgggt cctctagggt      60
tttgttttgt tgttctcacg gcacagccat cgctgttcca nagggatagt ttgagagatg    120
gcaaagctat ttcttgctct tgtttataaa cggtagcagt atactgcagg atagtgctcc    180
tngtgctacg gtgactgaat t                                              201
```

<210> SEQ ID NO 154
<211> LENGTH: 201
<212> TYPE: DNA

```
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 154
gctccgcaac catttagtc tgcagatcca aatcaacaac ttctatagcc tgcacatata        60
tcatcaatat tgtcagaaac aacatgttgc ttgatacaat nttccagcca attatgtaaa      120
ttctagagat gcaagtgtat acttctcata taccaattgt acaagcacat acaaaatgta      180
tacaattcag ccttccaaca a                                                201

<210> SEQ ID NO 155
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 155
agggcacgga gggattcaac gacaaacata ataatcgctt ctattatttt cgtagcggca        60
agtaggccaa tcatcaaccg aggtcagctg agtcggagga ngaagtggcc ctcggggagt      120
tccatgatcc gtcccaattc ccaactctct tgctctcacc atgtcgattc agaacgggag      180
ggaaaaaaac caaacaaaaa a                                                201

<210> SEQ ID NO 156
<211> LENGTH: 201
<212> TYPE: DNA
<213> ORGANISM: Zea mays
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
```

<400> SEQUENCE: 156

```
tgcaggcccn accctntagg cccgtgggcc tggcnntgnc gtgccgggca taggcccagg      60
tcntgccncg ctgggcgacc catttgctta tctatagagt ntagaatcgt gtgacctaat     120
tccatgcaat acacaagagt gatgttctat attagggggag agagctttca gttttactcc    180
aanacaagaa aattgggtnt t                                               201
```

<210> SEQ ID NO 157
<211> LENGTH: 201
<212> TYPE: DNA
<213> ORGANISM: Zea mays
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 157

```
gatatatcga tatcagcnat ttcaccaagc tattatatat tcatcacatg gggaaaaaag      60
caatttgcag ttttaattat gcagagtaga ctgctgctgc ntatccttag tcaagttgag     120
tcggctgttg agctgttata cctttcaagc acaatggcta tggggagcaa cagcgcagtg    180
gcggccgcct ggcggtagaa g                                               201
```

<210> SEQ ID NO 158
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 158

```
ttgagtagga ttacgaaaaa caagggatct taaaataact ttgaccattt catggtcatc      60
ccatttggtg ctcccgaggt tgcgcacttg gttcaccatt ntctttagtc gtttgtacat    120
tatttgcggc tcttctcctt tgttgaggtc gaatcgatcg agctcaccct cgattgtttc    180
ccacttggtg atcttggtca c                                               201
```

<210> SEQ ID NO 159
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 159

```
tgcagacggg cacgagatct gcgaaagagg tcaacatgct accggaagac tcggcgcgat      60
cgtagcaagt agtgggatag acacgcatga atgctttgat ntgtactagg tcatctcctc    120
gatcgactat ataaggttga ggaggtaccc ctacaaatag gttagatccc gctagatcac    180
tagggcacct tcatctccta c                                               201
```

<210> SEQ ID NO 160
<211> LENGTH: 121
<212> TYPE: DNA

<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t

<400> SEQUENCE: 160
ggaggctccg gttgtccgga tgtcgaagaa tcacgacagc ggcgaattcc gatctgcgca      60
nggaagaggt tgagcgtgga ccnggcagaa gagttgagga aaggggaaac catcncgggt     120
t                                                                    121

<210> SEQ ID NO 161
<211> LENGTH: 201
<212> TYPE: DNA
<213> ORGANISM: Zea mays
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 161
tncctcntta ttttagttgc actaattaca ggataatgct aagtgagtat tttggtcgtc      60
ttataaatta tttaatatgt tttgaatact tttagttctt naaaccaaaa aacgtagaga     120
ctaaacttta gtccttagac gaccaaacaa cccctaaatg tcataagcag gacaagtttc     180
attattaatt tgttgtttta t                                               201

<210> SEQ ID NO 162
<211> LENGTH: 201
<212> TYPE: DNA
<213> ORGANISM: Zea mays
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (193)..(194)
<223> OTHER INFORMATION: n is a, c, g, or t

<400> SEQUENCE: 162
aacgaagacn gtggctcagg agagaaatcc tagggttaat aagtggttgt ttgctgaaca    60
ccctaaaaga acaaaaaacg cgagattgta tgtaatccag natgagtcaa gttggctaga   120
gggtnngagg ctaaacattc tgctcgagac atccagggtt cgatccctga tccacngtag   180
gatttttttt acnncggaca g                                            201

<210> SEQ ID NO 163
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 163
gctaaactta tcttcaatca cgagtcatga tcaacttatt taaagtttaa aggcccataa    60
cagttattgc ataccaat ttagttctga ccgattctta ngacctatta ttttacatat    120
cagtgccagt ttgtcgaacc gccgccgcct gggttgcttg acggtgcacc aattttgttt   180
atatagaaga gcaaaaggct c                                            201

<210> SEQ ID NO 164
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 164
tgggacagag gctaaatttt agcggggtgt aaccaaacac ccctaagta cagttaagta     60 ggcaagcagc ctggcgaagg agactcacac gaggtgggct natgccgcaa cagctaagtc   120
ccaacctacg ccattaacgt cctctatata agcaagcagc gaacctctgc aaacatggtc   180
atcagcgaag cacaaagcgc a                                            201

<210> SEQ ID NO 165
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t

<400> SEQUENCE: 165
tacatagaat cccttacccc cttccatctc gtacgagaat cgagtagctc caccctggcc    60
gtgtattgta tgtatgcaag gcgacgggcc gtcgcgtact nactcgttcc atcggtacag   120
gtcacaggta catgcatgcc acatttgcca tacgaacaag tcgaaggcga aacggtcgtc   180
gactagcggg ccacntcatt c                                            201

<210> SEQ ID NO 166
<211> LENGTH: 353
<212> TYPE: DNA

```
<213> ORGANISM: Zea mays
<220> FEATURE:
<221> NAME/KEY: misc_feature
<222> LOCATION: (196)..(196)
<223> OTHER INFORMATION: n is a, c, g, or t

<400> SEQUENCE: 166
attggatgtt tttcagacac agttcagagt gcttgggact cagttttgaa tgagacgtgc    60
cctttcaaac catctatctg aaattaaaga agacaactca aaggctagtt ggatggagcg   120
ataaacaagt gggacatata aggtctcagt tggcattggc taaagaaatc cttcacaggc   180
tggagattga gggggntgga agaaccttat caccggctca aatctagttg aagaacaagg   240
taaaaaagca ttcattacca ttatcttcct tgaaatgaac catggcccgg ttgagaattg   300
agatcaagaa tctcatggct caaggagggg ggtgcaaatt caaagctctt cca          353

<210> SEQ ID NO 167
<211> LENGTH: 201
<212> TYPE: DNA
<213> ORGANISM: Zea mays
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 167
atggcgcaca tgccttgact cngtgatatt tttaaaaaat aataaatcaa atttgtgcat    60
ttttatagaa cagaagttat tctatctaat aaaaaaatca ntcaagttga tcaaaaatta   120
catagctttt gtgtctccta ggtacgtaga ccagacaaat attgtcaaac atagtagttt   180
aataggagca tggatgacgc t                                              201

<210> SEQ ID NO 168
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t

<400> SEQUENCE: 168
ccatcagaaa cacaacaggt gtgagccaca caaaggaaca gtcgaacaga gtacagacag    60
atgaatggga atggctagtc caagtatgca accccatcac nacctcgggt gtgtgtgttc   120
ctagttccta actacaaaca aacccgcttc tgactaacta atgtttcatc aaccaacgtt   180
tcatggactc agcttgacaa c                                              201

<210> SEQ ID NO 169
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
```

<400> SEQUENCE: 169
cgtggcggct ggagcaaaga ggccagctgc acgtagcatt tatcgatcag tatattgtgt    60
ngtggcacgt cacaaagtga gagacactaa tatatataca cacatcatga catacccgtc    120
c    121

<210> SEQ ID NO 170
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 170
gtttacagat tccgttccgt tttgcaaatc cagggctaac atctacgtta caaatcagta    60
ngccaaagta aagtgaaaaa gaaaaggttt tagctgtact agtcagttct cagttaactg    120
t    121

<210> SEQ ID NO 171
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 171
agcacatgaa acgattcgag gagatatgat gtgtggaatc gtggaaagca aagcgaaggg    60
naaaaaggtg cggtgactaa aagaaagtcc cagcgcatgg aaagcaagat cctggagcag    120
a    121

<210> SEQ ID NO 172
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 172
tggaactgtc caaagattgt tcgcatggta tattgttctt gatccgtagt aaactcggtc    60
ntagtccgcg gaggaaatat acatatagac ttttccccc ggatacctct tctcacgagt    120
t    121

<210> SEQ ID NO 173
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 173
gtcgtacaac gtcaacgcga ccgtcgatct caaaagctac ctgccggagc gcgtcgcggt    60
nggcttctcc gccgcgactg gaaaaggcgg cgagcagcac caggtgctgt cgtggtcatt   120
c                                                                   121

<210> SEQ ID NO 174
<211> LENGTH: 121
<212> TYPE: DNA
<213> ORGANISM: Zea mays
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 174
agcttccaat ctccnaaagc tccgcgctag gtcgctggcc caaaaagcat aggttaggtg    60
nggttctggt catgtatcta ttattctatc cagtgagcgt ggcacatctt aagatgtgct   120
c                                                                   121

<210> SEQ ID NO 175
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 175
gatctcggga cggaaagaca tacctgaagc aaccttggcg gggcggcgct agggttcgcc    60
naggcccggg gacggagtca agtggagtgg agctggagat gacgccgtcg gttaatggac   120
a                                                                   121

<210> SEQ ID NO 176
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 176
acaggagctt gcaccaaaat cccatacacg ttggcgtcga gaattgggtt cacaccatac    60
ntatctccat ccaggatgat cacttcalltt aagcatntag agttcaaata caaagataat   120
a                                                                   121

<210> SEQ ID NO 177
<211> LENGTH: 121
<212> TYPE: DNA
<213> ORGANISM: Zea mays
<220> FEATURE:
<221> NAME/KEY: misc_feature
<222> LOCATION: (61)..(61)

<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (118)..(119)
<223> OTHER INFORMATION: n is a, c, g, or t

<400> SEQUENCE: 177
tggtagctct tgcatggaat gtgattctgt ccttcaaagc ccacaaggag atcgtagcga    60
nanaggtgat gcggtgccaa cgaactgctt gggtctcagt ctcttnggtt agtacgtnna   120
a                                                                  121

<210> SEQ ID NO 178
<211> LENGTH: 121
<212> TYPE: DNA
<213> ORGANISM: Zea mays
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t

<400> SEQUENCE: 178
ggtgtgngta ataataccag aatatcccgg attcgtaacc taatggcgtt cgttgacagg    60
ntagncaggc gtttctcgag caggacaatg agttggctga aatgaggcag agactgcaag   120
a                                                                  121

<210> SEQ ID NO 179
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 179
gttgccgcca cgagggaggc gccattgctg ctgaagttga cgagtatagc gtagcagatg    60
nacgggttct cggcctgaag aagatacgtt atatgtacta gtggagcttt ggcttacgct   120
g                                                                  121

<210> SEQ ID NO 180
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t

```
<400> SEQUENCE: 180
ctcggaccca tggaacaggt ccttgatgtg agacctgatg tctctcttca tcttcgagat    60 ngcccttttgc tgngacaacc ggaacatgta cgcccggctc cctttggacc tgtggtggtg   120
c                                                                    121

<210> SEQ ID NO 181
<211> LENGTH: 121
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 181
cacncctgtc ttcgtattgg aatcctctat cttgtattta tccttgtttt caatgatgcc    60
ntcaagcctc atgttgatgg ctctgatttt tctggagagg ccgcgtctca tccgtatttg   120
a                                                                    121

<210> SEQ ID NO 182
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 182
cactgtgatc aagctgacgt tgaggttacc tgcatgcgcc tgatgatcct ttcgccgctg    60
nggacgacgt cgcggaagcc gccggcggtg gagcagcagc accaggacca ggcgacgggg   120
a                                                                    121

<210> SEQ ID NO 183
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t

<400> SEQUENCE: 183
aagtcagaag ggggaacgaa tagtaccaga agacgattcc gtgaataaca gctaatcggc    60
ngcggcgaga tgaaccaccg ngtacagaaa caacacccgc cagtaaggta agagggaagg   120
a                                                                    121

<210> SEQ ID NO 184
<211> LENGTH: 121
<212> TYPE: DNA
<213> ORGANISM: Zea mays
<220> FEATURE:
<221> NAME/KEY: misc_feature
<222> LOCATION: (61)..(61)
```

<223> OTHER INFORMATION: n is a, c, g, or t

<400> SEQUENCE: 184
agctcatcat gcagtacccc atatacctgt cgttgtagct caggcatcgc tggtactcgc    60
nacccacacc catggctgcg ttaacagcgg tacggcaaga ctgacagcag ctgcttgcgt   120
g                                                                  121

<210> SEQ ID NO 185
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t

<400> SEQUENCE: 185
cagtgatgat taatttacca gcagcgctga cctgtgagca tagatgttgt agtcttttcc    60
nttgagatac tccctcgtaa cgtagcggtc gtcggcgtcc ggcgcttnag gagccttggc   120
g                                                                  121

<210> SEQ ID NO 186
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 186
cctgcacgcc ggggtacgac gaggaccacc acgccagttg cagggacagc aggagcactg    60
ntgctgccac aggccgngct gccattgcta cgtacgnacg ctagccgcct tgtctgcgta   120
g                                                                  121

<210> SEQ ID NO 187
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t

<400> SEQUENCE: 187
tctcaaacag gccctaattc tatttcgcta taaataattg ttttcctatg cgaatccaaa    60
cgggaggtta ctttggtaga ctaatttttg tagctgatgt nataaaaagt tgttaataaa   120
tgacacgagg atagagaccg ttgttattag tcctgtccag tcccaaaagt acgaaatcca    180
natatatacg ttagtaaaga c                                              201

<210> SEQ ID NO 188
<211> LENGTH: 121
<212> TYPE: DNA
<213> ORGANISM: Zea mays
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 188
ggcatgtgcn tgaagacatt tgaattcatg aaccagatct cganaatgta gatttccaag    60
naaaaatggg caaagcgcct ctaatcgctc tccccccaca ataggcttgc catttgttgc    120
c                                                                    121

<210> SEQ ID NO 189
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t

<400> SEQUENCE: 189
gttgagatac ttttgcccgt aacatctcgt attccgtctg tgcatgactg gagtgttgat    60
nggntaattg cntatgtcaa gtcgttgnca acagatgagg tactggctaa acctaaattg    120
t                                                                    121

<210> SEQ ID NO 190
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

```
<400> SEQUENCE: 190
gggatgaatg cactttcagc cgcctccatg ccagcaaagc acattgtctc ctcagcactt    60
ncgcctcagt agaccgtcac gacaatgcta tggcnaagtc gttcataatc gcactcgaag   120
g                                                                  121

<210> SEQ ID NO 191
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t

<400> SEQUENCE: 191
ggtcttccaa aacaaagagt tatgtctagt ctaggagcaa agagtccaaa aaggacccaa    60
ncaagggcgc tnccattgac nctaatcacg ctagtatgct gctactacca agtgtcgatc   120
t                                                                  121

<210> SEQ ID NO 192
<211> LENGTH: 29
<212> TYPE: DNA
<213> ORGANISM: Zea mays

<400> SEQUENCE: 192
ggtgccattt ttaatttgta aaccacttg                                     29

<210> SEQ ID NO 193
<211> LENGTH: 20
<212> TYPE: DNA
<213> ORGANISM: Zea mays

<400> SEQUENCE: 193
cgcacagacc gatcgtacac                                               20

<210> SEQ ID NO 194
<211> LENGTH: 20
<212> TYPE: DNA
<213> ORGANISM: Zea mays

<400> SEQUENCE: 194
cggacggtct gcatattcga                                               20

<210> SEQ ID NO 195
<211> LENGTH: 25
<212> TYPE: DNA
<213> ORGANISM: Zea mays

<400> SEQUENCE: 195
caactcacct actcctgctc ttgtt                                         25

<210> SEQ ID NO 196
<211> LENGTH: 27
<212> TYPE: DNA
```

<213> ORGANISM: Zea mays

<400> SEQUENCE: 196
gtcagcaacc ctgatactag tacatca                                         27

<210> SEQ ID NO 197
<211> LENGTH: 28
<212> TYPE: DNA
<213> ORGANISM: Zea mays

<400> SEQUENCE: 197
tggccctaca tatgatataa ctcacact                                        28

<210> SEQ ID NO 198
<211> LENGTH: 29
<212> TYPE: DNA
<213> ORGANISM: Zea mays

<400> SEQUENCE: 198
ctcgttcctg ttaatactaa agcagaaat                                       29

<210> SEQ ID NO 199
<211> LENGTH: 25
<212> TYPE: DNA
<213> ORGANISM: Zea mays

<400> SEQUENCE: 199
aaccaagtga atgtgtacca tttcc                                           25

<210> SEQ ID NO 200
<211> LENGTH: 26
<212> TYPE: DNA
<213> ORGANISM: Zea mays

<400> SEQUENCE: 200
tttgggtaaa gaagaaggag ctagaa                                          26

<210> SEQ ID NO 201
<211> LENGTH: 21
<212> TYPE: DNA
<213> ORGANISM: Zea mays

<400> SEQUENCE: 201
gcaaagtgtg gccatgtgat c                                               21

<210> SEQ ID NO 202
<211> LENGTH: 29
<212> TYPE: DNA
<213> ORGANISM: Zea mays

<400> SEQUENCE: 202
gtagtagcag tacattacat agcaacagt                                       29

<210> SEQ ID NO 203
<211> LENGTH: 20
<212> TYPE: DNA
<213> ORGANISM: Zea mays

<400> SEQUENCE: 203
gctcgtcgtt ccaaggaaac                                                 20

<210> SEQ ID NO 204
<211> LENGTH: 21

```
<212> TYPE: DNA
<213> ORGANISM: Zea mays

<400> SEQUENCE: 204
gcaaacaagt cgaggagctt t                                    21

<210> SEQ ID NO 205
<211> LENGTH: 23
<212> TYPE: DNA
<213> ORGANISM: Zea mays

<400> SEQUENCE: 205
ccattcggat ttgtttttga aga                                  23

<210> SEQ ID NO 206
<211> LENGTH: 25
<212> TYPE: DNA
<213> ORGANISM: Zea mays

<400> SEQUENCE: 206
accaacagga acaaatgacc taact                                25

<210> SEQ ID NO 207
<211> LENGTH: 21
<212> TYPE: DNA
<213> ORGANISM: Zea mays

<400> SEQUENCE: 207
gcacattctt ctcggcaaca c                                    21

<210> SEQ ID NO 208
<211> LENGTH: 18
<212> TYPE: DNA
<213> ORGANISM: Zea mays

<400> SEQUENCE: 208
tgtaggcagc ggcatctc                                        18

<210> SEQ ID NO 209
<211> LENGTH: 24
<212> TYPE: DNA
<213> ORGANISM: Zea mays

<400> SEQUENCE: 209
gacacggtca tgcttaagta gact                                 24

<210> SEQ ID NO 210
<211> LENGTH: 20
<212> TYPE: DNA
<213> ORGANISM: Zea mays

<400> SEQUENCE: 210
tggatgctaa cacggcaaaa                                      20

<210> SEQ ID NO 211
<211> LENGTH: 28
<212> TYPE: DNA
<213> ORGANISM: Zea mays

<400> SEQUENCE: 211
tgccaacaag aagaaagaac taattcca                             28

<210> SEQ ID NO 212
```

```
<211> LENGTH: 21
<212> TYPE: DNA
<213> ORGANISM: Zea mays

<400> SEQUENCE: 212
gccgctcttc catttctacg t                                              21

<210> SEQ ID NO 213
<211> LENGTH: 23
<212> TYPE: DNA
<213> ORGANISM: Zea mays

<400> SEQUENCE: 213
tgattcaatc actgtgccaa gac                                            23

<210> SEQ ID NO 214
<211> LENGTH: 20
<212> TYPE: DNA
<213> ORGANISM: Zea mays

<400> SEQUENCE: 214
gagaccaccc ttcacgatgt                                                20

<210> SEQ ID NO 215
<211> LENGTH: 19
<212> TYPE: DNA
<213> ORGANISM: Zea mays

<400> SEQUENCE: 215
ggtggagagg tggctgatg                                                 19

<210> SEQ ID NO 216
<211> LENGTH: 23
<212> TYPE: DNA
<213> ORGANISM: Zea mays

<400> SEQUENCE: 216
cgcaccgtct ttgataggta aac                                            23

<210> SEQ ID NO 217
<211> LENGTH: 23
<212> TYPE: DNA
<213> ORGANISM: Zea mays

<400> SEQUENCE: 217
agtcagctca aatgctcaac cat                                            23

<210> SEQ ID NO 218
<211> LENGTH: 20
<212> TYPE: DNA
<213> ORGANISM: Zea mays

<400> SEQUENCE: 218
cctttcggac ccgttcaaca                                                20

<210> SEQ ID NO 219
<211> LENGTH: 21
<212> TYPE: DNA
<213> ORGANISM: Zea mays

<400> SEQUENCE: 219
tcgtaaacca cttgcctgca a                                              21
```

```
<210> SEQ ID NO 220
<211> LENGTH: 17
<212> TYPE: DNA
<213> ORGANISM: Zea mays

<400> SEQUENCE: 220
cgtcagcgtc agcgtca                                                  17

<210> SEQ ID NO 221
<211> LENGTH: 26
<212> TYPE: DNA
<213> ORGANISM: Zea mays

<400> SEQUENCE: 221
atgtgttgat agtagggaag gacaga                                        26

<210> SEQ ID NO 222
<211> LENGTH: 31
<212> TYPE: DNA
<213> ORGANISM: Zea mays

<400> SEQUENCE: 222
aggggtgact ttcatatata tataaccaag a                                  31

<210> SEQ ID NO 223
<211> LENGTH: 23
<212> TYPE: DNA
<213> ORGANISM: Zea mays

<400> SEQUENCE: 223
atcaagccaa ggaatctgtc atg                                           23

<210> SEQ ID NO 224
<211> LENGTH: 23
<212> TYPE: DNA
<213> ORGANISM: Zea mays

<400> SEQUENCE: 224
actaccagat cagacggtga ctt                                           23

<210> SEQ ID NO 225
<211> LENGTH: 24
<212> TYPE: DNA
<213> ORGANISM: Zea mays

<400> SEQUENCE: 225
gttctaatac ccaagaggcc aaga                                          24

<210> SEQ ID NO 226
<211> LENGTH: 26
<212> TYPE: DNA
<213> ORGANISM: Zea mays

<400> SEQUENCE: 226
aagataatgt tgtttgtgtc ctcacc                                        26

<210> SEQ ID NO 227
<211> LENGTH: 24
<212> TYPE: DNA
<213> ORGANISM: Zea mays

<400> SEQUENCE: 227
cctatttgtt tggtgcaatg gtaa                                          24
```

```
<210> SEQ ID NO 228
<211> LENGTH: 23
<212> TYPE: DNA
<213> ORGANISM: Zea mays

<400> SEQUENCE: 228
ctaggccttg ctgttcacat agc                                    23

<210> SEQ ID NO 229
<211> LENGTH: 19
<212> TYPE: DNA
<213> ORGANISM: Zea mays

<400> SEQUENCE: 229
cctggccgtc aatgaacaa                                         19

<210> SEQ ID NO 230
<211> LENGTH: 23
<212> TYPE: DNA
<213> ORGANISM: Zea mays

<400> SEQUENCE: 230
cgcaggtacg gttcatttga aga                                    23

<210> SEQ ID NO 231
<211> LENGTH: 24
<212> TYPE: DNA
<213> ORGANISM: Zea mays

<400> SEQUENCE: 231
tgacatcgtg atgcaaattt tggg                                   24

<210> SEQ ID NO 232
<211> LENGTH: 18
<212> TYPE: DNA
<213> ORGANISM: Zea mays

<400> SEQUENCE: 232
gccggtggaa ctgacgaa                                          18

<210> SEQ ID NO 233
<211> LENGTH: 18
<212> TYPE: DNA
<213> ORGANISM: Zea mays

<400> SEQUENCE: 233
tgcgtgtcgt tcgtggat                                          18

<210> SEQ ID NO 234
<211> LENGTH: 15
<212> TYPE: DNA
<213> ORGANISM: Zea mays

<400> SEQUENCE: 234
gcggtcggcg ttcgt                                             15

<210> SEQ ID NO 235
<211> LENGTH: 22
<212> TYPE: DNA
<213> ORGANISM: Zea mays

<400> SEQUENCE: 235
ctcagctgtc aaaggcgaaa ag                                     22
```

<210> SEQ ID NO 236
<211> LENGTH: 27
<212> TYPE: DNA
<213> ORGANISM: Zea mays

<400> SEQUENCE: 236
tcttgacatc acacctacag aggtatc 27

<210> SEQ ID NO 237
<211> LENGTH: 20
<212> TYPE: DNA
<213> ORGANISM: Zea mays

<400> SEQUENCE: 237
aggccgtgat catggagatt 20

<210> SEQ ID NO 238
<211> LENGTH: 25
<212> TYPE: DNA
<213> ORGANISM: Zea mays

<400> SEQUENCE: 238
tgtgggactg gatttaaagg tttgt 25

<210> SEQ ID NO 239
<211> LENGTH: 27
<212> TYPE: DNA
<213> ORGANISM: Zea mays

<400> SEQUENCE: 239
ggtctgctcc aagtttcgat agttata 27

<210> SEQ ID NO 240
<211> LENGTH: 27
<212> TYPE: DNA
<213> ORGANISM: Zea mays

<400> SEQUENCE: 240
tgggccttat cctaaagaaa taaaaga 27

<210> SEQ ID NO 241
<211> LENGTH: 25
<212> TYPE: DNA
<213> ORGANISM: Zea mays

<400> SEQUENCE: 241
gagaaaagca gcacaagaga gatgt 25

<210> SEQ ID NO 242
<211> LENGTH: 24
<212> TYPE: DNA
<213> ORGANISM: Zea mays

<400> SEQUENCE: 242
gcggcctcat agattatcat catc 24

<210> SEQ ID NO 243
<211> LENGTH: 24
<212> TYPE: DNA
<213> ORGANISM: Zea mays

```
<400> SEQUENCE: 243
tcgtgtggac cttgtgtatg aaac                                              24

<210> SEQ ID NO 244
<211> LENGTH: 20
<212> TYPE: DNA
<213> ORGANISM: Zea mays

<400> SEQUENCE: 244
ccgctgtgca agtgtacatg                                                   20

<210> SEQ ID NO 245
<211> LENGTH: 22
<212> TYPE: DNA
<213> ORGANISM: Zea mays

<400> SEQUENCE: 245
ctttcatcct gccggaatct ca                                                22

<210> SEQ ID NO 246
<211> LENGTH: 20
<212> TYPE: DNA
<213> ORGANISM: Zea mays

<400> SEQUENCE: 246
tgtgggacca aagccttcag                                                   20

<210> SEQ ID NO 247
<211> LENGTH: 22
<212> TYPE: DNA
<213> ORGANISM: Zea mays

<400> SEQUENCE: 247
gagtgcaggt catcagtttg ga                                                22

<210> SEQ ID NO 248
<211> LENGTH: 23
<212> TYPE: DNA
<213> ORGANISM: Zea mays

<400> SEQUENCE: 248
actgcaacct tgtgctcaat ctt                                               23

<210> SEQ ID NO 249
<211> LENGTH: 22
<212> TYPE: DNA
<213> ORGANISM: Zea mays

<400> SEQUENCE: 249
aagccgtggt ggtaatcaga ga                                                22

<210> SEQ ID NO 250
<211> LENGTH: 24
<212> TYPE: DNA
<213> ORGANISM: Zea mays

<400> SEQUENCE: 250
gcggatgagg attcaagtag caat                                              24

<210> SEQ ID NO 251
<211> LENGTH: 19
<212> TYPE: DNA
```

```
<213> ORGANISM: Zea mays

<400> SEQUENCE: 251
gctagcagcg acgcattgt                                              19

<210> SEQ ID NO 252
<211> LENGTH: 23
<212> TYPE: DNA
<213> ORGANISM: Zea mays

<400> SEQUENCE: 252
ccctctttga aatgtttgtg caa                                         23

<210> SEQ ID NO 253
<211> LENGTH: 27
<212> TYPE: DNA
<213> ORGANISM: Zea mays

<400> SEQUENCE: 253
tgttggaaag gtgtgtgata tcataat                                     27

<210> SEQ ID NO 254
<211> LENGTH: 25
<212> TYPE: DNA
<213> ORGANISM: Zea mays

<400> SEQUENCE: 254
aaggccatag atctgatgtt tcatc                                       25

<210> SEQ ID NO 255
<211> LENGTH: 25
<212> TYPE: DNA
<213> ORGANISM: Zea mays

<400> SEQUENCE: 255
tgtcgctgtg ggtatatctg aacta                                       25

<210> SEQ ID NO 256
<211> LENGTH: 24
<212> TYPE: DNA
<213> ORGANISM: Zea mays

<400> SEQUENCE: 256
cctgtgtaga gagctgctgg atct                                        24

<210> SEQ ID NO 257
<211> LENGTH: 19
<212> TYPE: DNA
<213> ORGANISM: Zea mays

<400> SEQUENCE: 257
cgccgcaggt tatgatcct                                              19

<210> SEQ ID NO 258
<211> LENGTH: 20
<212> TYPE: DNA
<213> ORGANISM: Zea mays

<400> SEQUENCE: 258
gtgaagacgg cgaagtgttc                                             20

<210> SEQ ID NO 259
<211> LENGTH: 19
```

```
<212> TYPE: DNA
<213> ORGANISM: Zea mays

<400> SEQUENCE: 259
gcgttacgtt gtcgttgca                                        19

<210> SEQ ID NO 260
<211> LENGTH: 20
<212> TYPE: DNA
<213> ORGANISM: Zea mays

<400> SEQUENCE: 260
gtagcccacg ccatgatttc                                       20

<210> SEQ ID NO 261
<211> LENGTH: 20
<212> TYPE: DNA
<213> ORGANISM: Zea mays

<400> SEQUENCE: 261
atggcagatg tcgcaagtga                                       20

<210> SEQ ID NO 262
<211> LENGTH: 18
<212> TYPE: DNA
<213> ORGANISM: Zea mays

<400> SEQUENCE: 262
aggaacgctt ggcttcgt                                         18

<210> SEQ ID NO 263
<211> LENGTH: 24
<212> TYPE: DNA
<213> ORGANISM: Zea mays

<400> SEQUENCE: 263
tggagctgta tttgtgactt gtgt                                  24

<210> SEQ ID NO 264
<211> LENGTH: 24
<212> TYPE: DNA
<213> ORGANISM: Zea mays

<400> SEQUENCE: 264
tcgttatgcc cttctctctt agct                                  24

<210> SEQ ID NO 265
<211> LENGTH: 22
<212> TYPE: DNA
<213> ORGANISM: Zea mays

<400> SEQUENCE: 265
gagtaacatg ctggaggaca gt                                    22

<210> SEQ ID NO 266
<211> LENGTH: 19
<212> TYPE: DNA
<213> ORGANISM: Zea mays

<400> SEQUENCE: 266
cccaagccca tttgaagct                                        19

<210> SEQ ID NO 267
```

-continued

```
<211> LENGTH: 25
<212> TYPE: DNA
<213> ORGANISM: Zea mays

<400> SEQUENCE: 267
cctgtcctat tttggcatcc ctaat                                          25

<210> SEQ ID NO 268
<211> LENGTH: 19
<212> TYPE: DNA
<213> ORGANISM: Zea mays

<400> SEQUENCE: 268
gctcgaccga ggtgtactt                                                 19

<210> SEQ ID NO 269
<211> LENGTH: 21
<212> TYPE: DNA
<213> ORGANISM: Zea mays

<400> SEQUENCE: 269
ttcactgact gcgatgacga a                                              21

<210> SEQ ID NO 270
<211> LENGTH: 22
<212> TYPE: DNA
<213> ORGANISM: Zea mays

<400> SEQUENCE: 270
cgtaggcttc ctgcttcttc tg                                             22

<210> SEQ ID NO 271
<211> LENGTH: 19
<212> TYPE: DNA
<213> ORGANISM: Zea mays

<400> SEQUENCE: 271
gcgcacgaga tgcatactg                                                 19

<210> SEQ ID NO 272
<211> LENGTH: 23
<212> TYPE: DNA
<213> ORGANISM: Zea mays

<400> SEQUENCE: 272
acccactgaa cgaccaagtc tac                                            23

<210> SEQ ID NO 273
<211> LENGTH: 27
<212> TYPE: DNA
<213> ORGANISM: Zea mays

<400> SEQUENCE: 273
gccacattct cctataatat cctgtca                                        27

<210> SEQ ID NO 274
<211> LENGTH: 25
<212> TYPE: DNA
<213> ORGANISM: Zea mays

<400> SEQUENCE: 274
cattgggacg agtacttagg aagag                                          25
```

```
<210> SEQ ID NO 275
<211> LENGTH: 21
<212> TYPE: DNA
<213> ORGANISM: Zea mays

<400> SEQUENCE: 275
tgcgcatcca gatagaaagc a                                            21

<210> SEQ ID NO 276
<211> LENGTH: 21
<212> TYPE: DNA
<213> ORGANISM: Zea mays

<400> SEQUENCE: 276
cgaactgctc gatacgctca t                                            21

<210> SEQ ID NO 277
<211> LENGTH: 22
<212> TYPE: DNA
<213> ORGANISM: Zea mays

<400> SEQUENCE: 277
tcagaagatg gtggtgctct tg                                           22

<210> SEQ ID NO 278
<211> LENGTH: 34
<212> TYPE: DNA
<213> ORGANISM: Zea mays

<400> SEQUENCE: 278
ggtgaacaag acactactag agatatgtat agtc                              34

<210> SEQ ID NO 279
<211> LENGTH: 24
<212> TYPE: DNA
<213> ORGANISM: Zea mays

<400> SEQUENCE: 279
aaagactaaa cattgcagga ggct                                         24

<210> SEQ ID NO 280
<211> LENGTH: 27
<212> TYPE: DNA
<213> ORGANISM: Zea mays

<400> SEQUENCE: 280
tgagaaagta aggatcaagc aaaagct                                      27

<210> SEQ ID NO 281
<211> LENGTH: 32
<212> TYPE: DNA
<213> ORGANISM: Zea mays

<400> SEQUENCE: 281
tgtatcttga actaattaca gtatgaaatg ga                                32

<210> SEQ ID NO 282
<211> LENGTH: 25
<212> TYPE: DNA
<213> ORGANISM: Zea mays

<400> SEQUENCE: 282
acctgagaaa gaagaatgtc cttga                                        25
```

```
<210> SEQ ID NO 283
<211> LENGTH: 18
<212> TYPE: DNA
<213> ORGANISM: Zea mays

<400> SEQUENCE: 283
gcgcagcatt ccccagta                                              18

<210> SEQ ID NO 284
<211> LENGTH: 25
<212> TYPE: DNA
<213> ORGANISM: Zea mays

<400> SEQUENCE: 284
tgaaacaagg tcggatgtta gtgta                                      25

<210> SEQ ID NO 285
<211> LENGTH: 21
<212> TYPE: DNA
<213> ORGANISM: Zea mays

<400> SEQUENCE: 285
atcgagaagg agaccgtgga c                                          21

<210> SEQ ID NO 286
<211> LENGTH: 21
<212> TYPE: DNA
<213> ORGANISM: Zea mays

<400> SEQUENCE: 286
accatccgcc atttccatct c                                          21

<210> SEQ ID NO 287
<211> LENGTH: 24
<212> TYPE: DNA
<213> ORGANISM: Zea mays

<400> SEQUENCE: 287
acacattctc ggatgcattt tgga                                       24

<210> SEQ ID NO 288
<211> LENGTH: 21
<212> TYPE: DNA
<213> ORGANISM: Zea mays

<400> SEQUENCE: 288
tgcttctgct tgcatcgact t                                          21

<210> SEQ ID NO 289
<211> LENGTH: 20
<212> TYPE: DNA
<213> ORGANISM: Zea mays

<400> SEQUENCE: 289
aacaacgacc gccattctct                                            20

<210> SEQ ID NO 290
<211> LENGTH: 19
<212> TYPE: DNA
<213> ORGANISM: Zea mays

<400> SEQUENCE: 290
caccacgttg ccgaagaag                                             19
```

<210> SEQ ID NO 291
<211> LENGTH: 18
<212> TYPE: DNA
<213> ORGANISM: Zea mays

<400> SEQUENCE: 291
cagctgtgcg aggtctga                                                        18

<210> SEQ ID NO 292
<211> LENGTH: 24
<212> TYPE: DNA
<213> ORGANISM: Zea mays

<400> SEQUENCE: 292
cgacgcaaac tggttaatct atca                                                 24

<210> SEQ ID NO 293
<211> LENGTH: 34
<212> TYPE: DNA
<213> ORGANISM: Zea mays

<400> SEQUENCE: 293
cagctagtaa gaatgtataa aaagttattg ttca                                      34

<210> SEQ ID NO 294
<211> LENGTH: 21
<212> TYPE: DNA
<213> ORGANISM: Zea mays

<400> SEQUENCE: 294
tgacgtgccg gaacattcta g                                                    21

<210> SEQ ID NO 295
<211> LENGTH: 23
<212> TYPE: DNA
<213> ORGANISM: Zea mays

<400> SEQUENCE: 295
cattggtgtc gttacatcag gaa                                                  23

<210> SEQ ID NO 296
<211> LENGTH: 29
<212> TYPE: DNA
<213> ORGANISM: Zea mays

<400> SEQUENCE: 296
ctccattgtt ctctatctat taggacaga                                            29

<210> SEQ ID NO 297
<211> LENGTH: 22
<212> TYPE: DNA
<213> ORGANISM: Zea mays

<400> SEQUENCE: 297
ggtagtccag gagcctgtgg ta                                                   22

<210> SEQ ID NO 298
<211> LENGTH: 22
<212> TYPE: DNA
<213> ORGANISM: Zea mays

```
<400> SEQUENCE: 298
aagggtaaat accgtgccaa aa                                      22

<210> SEQ ID NO 299
<211> LENGTH: 26
<212> TYPE: DNA
<213> ORGANISM: Zea mays

<400> SEQUENCE: 299
tggtcatgac acaaacaaca aaatgg                                  26

<210> SEQ ID NO 300
<211> LENGTH: 17
<212> TYPE: DNA
<213> ORGANISM: Zea mays

<400> SEQUENCE: 300
gtccgcagcc gagaaga                                            17

<210> SEQ ID NO 301
<211> LENGTH: 18
<212> TYPE: DNA
<213> ORGANISM: Zea mays

<400> SEQUENCE: 301
gcccacagtg cctaagca                                           18

<210> SEQ ID NO 302
<211> LENGTH: 21
<212> TYPE: DNA
<213> ORGANISM: Zea mays

<400> SEQUENCE: 302
cccgaaactt tgtaccgctg t                                       21

<210> SEQ ID NO 303
<211> LENGTH: 22
<212> TYPE: DNA
<213> ORGANISM: Zea mays

<400> SEQUENCE: 303
gctgtggttt caaggagaag ct                                      22

<210> SEQ ID NO 304
<211> LENGTH: 16
<212> TYPE: DNA
<213> ORGANISM: Zea mays

<400> SEQUENCE: 304
accctggaag tcaccg                                             16

<210> SEQ ID NO 305
<211> LENGTH: 16
<212> TYPE: DNA
<213> ORGANISM: Zea mays

<400> SEQUENCE: 305
atcatctcgc tttcag                                             16

<210> SEQ ID NO 306
<211> LENGTH: 17
<212> TYPE: DNA
```

```
<213> ORGANISM: Zea mays

<400> SEQUENCE: 306
actctacccc ggaacgt                                                  17

<210> SEQ ID NO 307
<211> LENGTH: 17
<212> TYPE: DNA
<213> ORGANISM: Zea mays

<400> SEQUENCE: 307
tgctgaacta tacgtcc                                                  17

<210> SEQ ID NO 308
<211> LENGTH: 15
<212> TYPE: DNA
<213> ORGANISM: Zea mays

<400> SEQUENCE: 308
atgctacaaa acttg                                                    15

<210> SEQ ID NO 309
<211> LENGTH: 18
<212> TYPE: DNA
<213> ORGANISM: Zea mays

<400> SEQUENCE: 309
aatgactaaa agatttca                                                 18

<210> SEQ ID NO 310
<211> LENGTH: 16
<212> TYPE: DNA
<213> ORGANISM: Zea mays

<400> SEQUENCE: 310
acagtgagaa ataaat                                                   16

<210> SEQ ID NO 311
<211> LENGTH: 15
<212> TYPE: DNA
<213> ORGANISM: Zea mays

<400> SEQUENCE: 311
aatcttcgaa attgc                                                    15

<210> SEQ ID NO 312
<211> LENGTH: 13
<212> TYPE: DNA
<213> ORGANISM: Zea mays

<400> SEQUENCE: 312
acgttcagaa tcc                                                      13

<210> SEQ ID NO 313
<211> LENGTH: 19
<212> TYPE: DNA
<213> ORGANISM: Zea mays

<400> SEQUENCE: 313
tccaacagat ctatgccac                                                19

<210> SEQ ID NO 314
<211> LENGTH: 15
```

```
<212> TYPE: DNA
<213> ORGANISM: Zea mays

<400> SEQUENCE: 314
ctgcactcgg ttgat                                              15

<210> SEQ ID NO 315
<211> LENGTH: 14
<212> TYPE: DNA
<213> ORGANISM: Zea mays

<400> SEQUENCE: 315
cccgcaaagg ccgt                                               14

<210> SEQ ID NO 316
<211> LENGTH: 17
<212> TYPE: DNA
<213> ORGANISM: Zea mays

<400> SEQUENCE: 316
actttaccgg gctactg                                            17

<210> SEQ ID NO 317
<211> LENGTH: 15
<212> TYPE: DNA
<213> ORGANISM: Zea mays

<400> SEQUENCE: 317
ctctccttga agcat                                              15

<210> SEQ ID NO 318
<211> LENGTH: 21
<212> TYPE: DNA
<213> ORGANISM: Zea mays

<400> SEQUENCE: 318
acttgtcatg attatcgtac g                                       21

<210> SEQ ID NO 319
<211> LENGTH: 16
<212> TYPE: DNA
<213> ORGANISM: Zea mays

<400> SEQUENCE: 319
aacgacaccg ccccga                                             16

<210> SEQ ID NO 320
<211> LENGTH: 15
<212> TYPE: DNA
<213> ORGANISM: Zea mays

<400> SEQUENCE: 320
cttcttgaat cttcg                                              15

<210> SEQ ID NO 321
<211> LENGTH: 15
<212> TYPE: DNA
<213> ORGANISM: Zea mays

<400> SEQUENCE: 321
aaggctcgta atggt                                              15

<210> SEQ ID NO 322
```

```
<211> LENGTH: 16
<212> TYPE: DNA
<213> ORGANISM: Zea mays

<400> SEQUENCE: 322
atgtaggata gaaatc                                                       16

<210> SEQ ID NO 323
<211> LENGTH: 18
<212> TYPE: DNA
<213> ORGANISM: Zea mays

<400> SEQUENCE: 323
atgttcatgt agatcctt                                                     18

<210> SEQ ID NO 324
<211> LENGTH: 14
<212> TYPE: DNA
<213> ORGANISM: Zea mays

<400> SEQUENCE: 324
cctcgttggg aacg                                                         14

<210> SEQ ID NO 325
<211> LENGTH: 16
<212> TYPE: DNA
<213> ORGANISM: Zea mays

<400> SEQUENCE: 325
actttgggat aacgca                                                       16

<210> SEQ ID NO 326
<211> LENGTH: 20
<212> TYPE: DNA
<213> ORGANISM: Zea mays

<400> SEQUENCE: 326
tcatctcctc ttctatgttg                                                   20

<210> SEQ ID NO 327
<211> LENGTH: 17
<212> TYPE: DNA
<213> ORGANISM: Zea mays

<400> SEQUENCE: 327
atcaggagaa ccaaatc                                                      17

<210> SEQ ID NO 328
<211> LENGTH: 15
<212> TYPE: DNA
<213> ORGANISM: Zea mays

<400> SEQUENCE: 328
ctctcgtcat aactg                                                        15

<210> SEQ ID NO 329
<211> LENGTH: 16
<212> TYPE: DNA
<213> ORGANISM: Zea mays

<400> SEQUENCE: 329
tgatgcatca tactgg                                                       16
```

```
<210> SEQ ID NO 330
<211> LENGTH: 18
<212> TYPE: DNA
<213> ORGANISM: Zea mays

<400> SEQUENCE: 330
atgtgtgaat gatatttt                                                 18

<210> SEQ ID NO 331
<211> LENGTH: 19
<212> TYPE: DNA
<213> ORGANISM: Zea mays

<400> SEQUENCE: 331
tgtttcttaa gaaaaatac                                                19

<210> SEQ ID NO 332
<211> LENGTH: 15
<212> TYPE: DNA
<213> ORGANISM: Zea mays

<400> SEQUENCE: 332
atgcaagaaa gaagc                                                    15

<210> SEQ ID NO 333
<211> LENGTH: 13
<212> TYPE: DNA
<213> ORGANISM: Zea mays

<400> SEQUENCE: 333
cgccatagct ttt                                                      13

<210> SEQ ID NO 334
<211> LENGTH: 20
<212> TYPE: DNA
<213> ORGANISM: Zea mays

<400> SEQUENCE: 334
caagtaagat acaaacatat                                               20

<210> SEQ ID NO 335
<211> LENGTH: 15
<212> TYPE: DNA
<213> ORGANISM: Zea mays

<400> SEQUENCE: 335
catggccatg tgaag                                                    15

<210> SEQ ID NO 336
<211> LENGTH: 17
<212> TYPE: DNA
<213> ORGANISM: Zea mays

<400> SEQUENCE: 336
ccagcttgtt atgttgc                                                  17

<210> SEQ ID NO 337
<211> LENGTH: 15
<212> TYPE: DNA
<213> ORGANISM: Zea mays

<400> SEQUENCE: 337
tgctaccacc ctttt                                                    15
```

```
<210> SEQ ID NO 338
<211> LENGTH: 14
<212> TYPE: DNA
<213> ORGANISM: Zea mays

<400> SEQUENCE: 338
cttgtggcat ttgt                                                      14

<210> SEQ ID NO 339
<211> LENGTH: 14
<212> TYPE: DNA
<213> ORGANISM: Zea mays

<400> SEQUENCE: 339
agggacccag gttg                                                      14

<210> SEQ ID NO 340
<211> LENGTH: 16
<212> TYPE: DNA
<213> ORGANISM: Zea mays

<400> SEQUENCE: 340
tgtgaactga aagaaa                                                    16

<210> SEQ ID NO 341
<211> LENGTH: 14
<212> TYPE: DNA
<213> ORGANISM: Zea mays

<400> SEQUENCE: 341
catgaactcc tccc                                                      14

<210> SEQ ID NO 342
<211> LENGTH: 18
<212> TYPE: DNA
<213> ORGANISM: Zea mays

<400> SEQUENCE: 342
tctagctttg cgtcacca                                                  18

<210> SEQ ID NO 343
<211> LENGTH: 18
<212> TYPE: DNA
<213> ORGANISM: Zea mays

<400> SEQUENCE: 343
ttggaaagac gccagctt                                                  18

<210> SEQ ID NO 344
<211> LENGTH: 17
<212> TYPE: DNA
<213> ORGANISM: Zea mays

<400> SEQUENCE: 344
actctagacg gaccgag                                                   17

<210> SEQ ID NO 345
<211> LENGTH: 18
<212> TYPE: DNA
<213> ORGANISM: Zea mays

<400> SEQUENCE: 345
ctctctctct taatttct                                                  18
```

```
<210> SEQ ID NO 346
<211> LENGTH: 14
<212> TYPE: DNA
<213> ORGANISM: Zea mays

<400> SEQUENCE: 346
atggccacga cggt                                                         14

<210> SEQ ID NO 347
<211> LENGTH: 17
<212> TYPE: DNA
<213> ORGANISM: Zea mays

<400> SEQUENCE: 347
caatctccgt cttcatc                                                      17

<210> SEQ ID NO 348
<211> LENGTH: 17
<212> TYPE: DNA
<213> ORGANISM: Zea mays

<400> SEQUENCE: 348
acagttctac attcaag                                                      17

<210> SEQ ID NO 349
<211> LENGTH: 14
<212> TYPE: DNA
<213> ORGANISM: Zea mays

<400> SEQUENCE: 349
actcgtggaa tatt                                                         14

<210> SEQ ID NO 350
<211> LENGTH: 15
<212> TYPE: DNA
<213> ORGANISM: Zea mays

<400> SEQUENCE: 350
acccctcccg gccac                                                        15

<210> SEQ ID NO 351
<211> LENGTH: 18
<212> TYPE: DNA
<213> ORGANISM: Zea mays

<400> SEQUENCE: 351
aacacatcat caaggtat                                                     18

<210> SEQ ID NO 352
<211> LENGTH: 17
<212> TYPE: DNA
<213> ORGANISM: Zea mays

<400> SEQUENCE: 352
ctacttgaca ttttacc                                                      17

<210> SEQ ID NO 353
<211> LENGTH: 16
<212> TYPE: DNA
<213> ORGANISM: Zea mays
```

```
<400> SEQUENCE: 353
aagacgcata ggtacc                                                     16

<210> SEQ ID NO 354
<211> LENGTH: 16
<212> TYPE: DNA
<213> ORGANISM: Zea mays

<400> SEQUENCE: 354
cttcatgtga accaat                                                     16

<210> SEQ ID NO 355
<211> LENGTH: 15
<212> TYPE: DNA
<213> ORGANISM: Zea mays

<400> SEQUENCE: 355
ctggcacaga tagag                                                      15

<210> SEQ ID NO 356
<211> LENGTH: 14
<212> TYPE: DNA
<213> ORGANISM: Zea mays

<400> SEQUENCE: 356
ccagctgcga acat                                                       14

<210> SEQ ID NO 357
<211> LENGTH: 16
<212> TYPE: DNA
<213> ORGANISM: Zea mays

<400> SEQUENCE: 357
tcgacatcag gctcag                                                     16

<210> SEQ ID NO 358
<211> LENGTH: 16
<212> TYPE: DNA
<213> ORGANISM: Zea mays

<400> SEQUENCE: 358
cggaacccat atctat                                                     16

<210> SEQ ID NO 359
<211> LENGTH: 15
<212> TYPE: DNA
<213> ORGANISM: Zea mays

<400> SEQUENCE: 359
agagctgcac tatgg                                                      15

<210> SEQ ID NO 360
<211> LENGTH: 15
<212> TYPE: DNA
<213> ORGANISM: Zea mays

<400> SEQUENCE: 360
ccctggaaat caccg                                                      15

<210> SEQ ID NO 361
<211> LENGTH: 15
<212> TYPE: DNA
```

```
<213> ORGANISM: Zea mays

<400> SEQUENCE: 361
ctcgctgtca gttta                                                    15

<210> SEQ ID NO 362
<211> LENGTH: 18
<212> TYPE: DNA
<213> ORGANISM: Zea mays

<400> SEQUENCE: 362
aactctacct cggaacgt                                                 18

<210> SEQ ID NO 363
<211> LENGTH: 16
<212> TYPE: DNA
<213> ORGANISM: Zea mays

<400> SEQUENCE: 363
tgctgagcta tacgtc                                                   16

<210> SEQ ID NO 364
<211> LENGTH: 14
<212> TYPE: DNA
<213> ORGANISM: Zea mays

<400> SEQUENCE: 364
atgctacgaa actt                                                     14

<210> SEQ ID NO 365
<211> LENGTH: 16
<212> TYPE: DNA
<213> ORGANISM: Zea mays

<400> SEQUENCE: 365
tgactaacag atttca                                                   16

<210> SEQ ID NO 366
<211> LENGTH: 15
<212> TYPE: DNA
<213> ORGANISM: Zea mays

<400> SEQUENCE: 366
cagtgaggaa taaat                                                    15

<210> SEQ ID NO 367
<211> LENGTH: 14
<212> TYPE: DNA
<213> ORGANISM: Zea mays

<400> SEQUENCE: 367
atcttcggaa ttgc                                                     14

<210> SEQ ID NO 368
<211> LENGTH: 16
<212> TYPE: DNA
<213> ORGANISM: Zea mays

<400> SEQUENCE: 368
aaggacgttt agaatc                                                   16

<210> SEQ ID NO 369
<211> LENGTH: 18
```

```
<212> TYPE: DNA
<213> ORGANISM: Zea mays

<400> SEQUENCE: 369
ccaacagatc tgtgccac                                              18

<210> SEQ ID NO 370
<211> LENGTH: 15
<212> TYPE: DNA
<213> ORGANISM: Zea mays

<400> SEQUENCE: 370
ctgcactccg ttgat                                                 15

<210> SEQ ID NO 371
<211> LENGTH: 14
<212> TYPE: DNA
<213> ORGANISM: Zea mays

<400> SEQUENCE: 371
cccgcatagg ccgt                                                  14

<210> SEQ ID NO 372
<211> LENGTH: 17
<212> TYPE: DNA
<213> ORGANISM: Zea mays

<400> SEQUENCE: 372
actttaccga gctactg                                               17

<210> SEQ ID NO 373
<211> LENGTH: 15
<212> TYPE: DNA
<213> ORGANISM: Zea mays

<400> SEQUENCE: 373
ctctcgttga agcat                                                 15

<210> SEQ ID NO 374
<211> LENGTH: 20
<212> TYPE: DNA
<213> ORGANISM: Zea mays

<400> SEQUENCE: 374
cttgtcatga ttctcgtacg                                            20

<210> SEQ ID NO 375
<211> LENGTH: 16
<212> TYPE: DNA
<213> ORGANISM: Zea mays

<400> SEQUENCE: 375
aacgacactg ccccga                                                16

<210> SEQ ID NO 376
<211> LENGTH: 15
<212> TYPE: DNA
<213> ORGANISM: Zea mays

<400> SEQUENCE: 376
cttcttgaac cttcg                                                 15

<210> SEQ ID NO 377
```

-continued

```
<211> LENGTH: 16
<212> TYPE: DNA
<213> ORGANISM: Zea mays

<400> SEQUENCE: 377
aaaggctcat aatggt                                                    16

<210> SEQ ID NO 378
<211> LENGTH: 17
<212> TYPE: DNA
<213> ORGANISM: Zea mays

<400> SEQUENCE: 378
catgtaggat ataaatc                                                   17

<210> SEQ ID NO 379
<211> LENGTH: 18
<212> TYPE: DNA
<213> ORGANISM: Zea mays

<400> SEQUENCE: 379
atgttcatgt agttcctt                                                  18

<210> SEQ ID NO 380
<211> LENGTH: 13
<212> TYPE: DNA
<213> ORGANISM: Zea mays

<400> SEQUENCE: 380
ctcgtcggga acg                                                       13

<210> SEQ ID NO 381
<211> LENGTH: 16
<212> TYPE: DNA
<213> ORGANISM: Zea mays

<400> SEQUENCE: 381
tcactttgag ataacg                                                    16

<210> SEQ ID NO 382
<211> LENGTH: 16
<212> TYPE: DNA
<213> ORGANISM: Zea mays

<400> SEQUENCE: 382
ctcctcttca atgttg                                                    16

<210> SEQ ID NO 383
<211> LENGTH: 14
<212> TYPE: DNA
<213> ORGANISM: Zea mays

<400> SEQUENCE: 383
aggaggacca aatc                                                      14

<210> SEQ ID NO 384
<211> LENGTH: 15
<212> TYPE: DNA
<213> ORGANISM: Zea mays

<400> SEQUENCE: 384
ctctcgacat aactg                                                     15
```

```
<210> SEQ ID NO 385
<211> LENGTH: 15
<212> TYPE: DNA
<213> ORGANISM: Zea mays

<400> SEQUENCE: 385
cctgatgcgt catac                                              15

<210> SEQ ID NO 386
<211> LENGTH: 19
<212> TYPE: DNA
<213> ORGANISM: Zea mays

<400> SEQUENCE: 386
aatgtgtgaa taatatttt                                          19

<210> SEQ ID NO 387
<211> LENGTH: 17
<212> TYPE: DNA
<213> ORGANISM: Zea mays

<400> SEQUENCE: 387
tttcttaagc aaaatac                                            17

<210> SEQ ID NO 388
<211> LENGTH: 14
<212> TYPE: DNA
<213> ORGANISM: Zea mays

<400> SEQUENCE: 388
tgcaagaaac aagc                                               14

<210> SEQ ID NO 389
<211> LENGTH: 14
<212> TYPE: DNA
<213> ORGANISM: Zea mays

<400> SEQUENCE: 389
cgccataact tttt                                               14

<210> SEQ ID NO 390
<211> LENGTH: 19
<212> TYPE: DNA
<213> ORGANISM: Zea mays

<400> SEQUENCE: 390
caagtaagat accaacata                                          19

<210> SEQ ID NO 391
<211> LENGTH: 15
<212> TYPE: DNA
<213> ORGANISM: Zea mays

<400> SEQUENCE: 391
catgggcatg tgaag                                              15

<210> SEQ ID NO 392
<211> LENGTH: 16
<212> TYPE: DNA
<213> ORGANISM: Zea mays

<400> SEQUENCE: 392
cagcttgttg tgttgc                                             16
```

```
<210> SEQ ID NO 393
<211> LENGTH: 16
<212> TYPE: DNA
<213> ORGANISM: Zea mays

<400> SEQUENCE: 393
tgctactacc cttttt                                                     16

<210> SEQ ID NO 394
<211> LENGTH: 16
<212> TYPE: DNA
<213> ORGANISM: Zea mays

<400> SEQUENCE: 394
acttgtgaca tttgtg                                                     16

<210> SEQ ID NO 395
<211> LENGTH: 15
<212> TYPE: DNA
<213> ORGANISM: Zea mays

<400> SEQUENCE: 395
tcagggaccc aagtt                                                      15

<210> SEQ ID NO 396
<211> LENGTH: 15
<212> TYPE: DNA
<213> ORGANISM: Zea mays

<400> SEQUENCE: 396
tgaaccgaaa gaaat                                                      15

<210> SEQ ID NO 397
<211> LENGTH: 15
<212> TYPE: DNA
<213> ORGANISM: Zea mays

<400> SEQUENCE: 397
catgaattcc tcccc                                                      15

<210> SEQ ID NO 398
<211> LENGTH: 17
<212> TYPE: DNA
<213> ORGANISM: Zea mays

<400> SEQUENCE: 398
ctagctttgc atcacca                                                    17

<210> SEQ ID NO 399
<211> LENGTH: 19
<212> TYPE: DNA
<213> ORGANISM: Zea mays

<400> SEQUENCE: 399
tttggaaaga caccagctt                                                  19

<210> SEQ ID NO 400
<211> LENGTH: 18
<212> TYPE: DNA
<213> ORGANISM: Zea mays

<400> SEQUENCE: 400
actctagact gaccgagg                                                   18
```

```
<210> SEQ ID NO 401
<211> LENGTH: 18
<212> TYPE: DNA
<213> ORGANISM: Zea mays

<400> SEQUENCE: 401
ctctctctct tcatttct                                               18

<210> SEQ ID NO 402
<211> LENGTH: 14
<212> TYPE: DNA
<213> ORGANISM: Zea mays

<400> SEQUENCE: 402
tggccaccac ggtg                                                   14

<210> SEQ ID NO 403
<211> LENGTH: 17
<212> TYPE: DNA
<213> ORGANISM: Zea mays

<400> SEQUENCE: 403
caatctccct cttcatc                                                17

<210> SEQ ID NO 404
<211> LENGTH: 17
<212> TYPE: DNA
<213> ORGANISM: Zea mays

<400> SEQUENCE: 404
tctacactca agatcaa                                                17

<210> SEQ ID NO 405
<211> LENGTH: 14
<212> TYPE: DNA
<213> ORGANISM: Zea mays

<400> SEQUENCE: 405
ctcgtgaaat attg                                                   14

<210> SEQ ID NO 406
<211> LENGTH: 16
<212> TYPE: DNA
<213> ORGANISM: Zea mays

<400> SEQUENCE: 406
aacccctcct ggccac                                                 16

<210> SEQ ID NO 407
<211> LENGTH: 15
<212> TYPE: DNA
<213> ORGANISM: Zea mays

<400> SEQUENCE: 407
aacacaccat caagg                                                  15

<210> SEQ ID NO 408
<211> LENGTH: 19
<212> TYPE: DNA
<213> ORGANISM: Zea mays
```

<400> SEQUENCE: 408
ctctacttaa cattttacc                                        19

<210> SEQ ID NO 409
<211> LENGTH: 15
<212> TYPE: DNA
<213> ORGANISM: Zea mays

<400> SEQUENCE: 409
agacgcatag atacc                                            15

<210> SEQ ID NO 410
<211> LENGTH: 17
<212> TYPE: DNA
<213> ORGANISM: Zea mays

<400> SEQUENCE: 410
tcatgtaaac caatctg                                          17

<210> SEQ ID NO 411
<211> LENGTH: 14
<212> TYPE: DNA
<213> ORGANISM: Zea mays

<400> SEQUENCE: 411
tggcacaaat agag                                             14

<210> SEQ ID NO 412
<211> LENGTH: 15
<212> TYPE: DNA
<213> ORGANISM: Zea mays

<400> SEQUENCE: 412
cccagatgcg aacat                                            15

<210> SEQ ID NO 413
<211> LENGTH: 16
<212> TYPE: DNA
<213> ORGANISM: Zea mays

<400> SEQUENCE: 413
tcgacatcag actcag                                           16

<210> SEQ ID NO 414
<211> LENGTH: 16
<212> TYPE: DNA
<213> ORGANISM: Zea mays

<400> SEQUENCE: 414
cggaacccat gtctat                                           16

<210> SEQ ID NO 415
<211> LENGTH: 14
<212> TYPE: DNA
<213> ORGANISM: Zea mays

<400> SEQUENCE: 415
agctgcatta tggc                                             14

MAIZE PLANTS WITH IMPROVED DISEASE RESISTANCE

CROSS-REFERENCE TO RELATED APPLICATIONS

This application claims the benefit of priority of U.S. Provisional Appl. Ser. No. 62/726,705, filed Sep. 4, 2018, the disclosure of which is hereby incorporated by reference in its entirety.

INCORPORATION OF SEQUENCE LISTING

A sequence listing containing the file named "MONS445US_ST25.txt" which is 176 kilobytes (measured in MS-Windows®) and created on Aug. 21, 2019, and comprises 415 sequences, and is incorporated herein by reference in its entirety.

FIELD OF THE INVENTION

The present invention relates to the field of plant breeding and more specifically to methods and compositions for producing corn plants exhibiting improved disease resistance.

BACKGROUND

Southern rust (SR) is a disease caused by the fungus *Puccinia polysora*. Southern rust infection is characterized by lesions that develop primarily on the upper surface of leaves. These lesions erupt and expose small spores that are dispersed by wind, which causes the disease to develop and spread rapidly. Since the most effective approach is to select varieties that are intrinsically resistant, what is needed are methods of identifying genetic sources of southern rust resistance and more effective methods of introgressing those genetic elements into commercial lines to provide new hybrids with improved genetic resistance to southern rust infection.

SUMMARY OF THE INVENTION

In one aspect, the invention provides methods of producing a corn plant with enhanced southern rust resistance, comprising introgressing into said plant a southern rust resistance allele, wherein said resistance allele is defined as located in a genomic region of said corn plant flanked by: marker loci SEQ ID NO: 48 and SEQ ID NO: 86 on chromosome 1; marker loci SEQ ID NO: 1 and SEQ ID NO: 5 on chromosome 1; marker loci SEQ ID NO: 14 and SEQ ID NO: 21 on chromosome 3; marker loci SEQ ID NO: 87 and SEQ ID NO: 25 on chromosome 5; marker loci SEQ ID NO: 26 and SEQ ID NO: 29 on chromosome 5; marker loci SEQ ID NO: 110 and SEQ ID NO: 168 on chromosome 6; or marker loci SEQ ID NO: 184 and SEQ ID NO: 46 on chromosome 10. In some embodiments, the segment is flanked by marker loci SEQ ID NO: 48 and SEQ ID NO: 86 on chromosome 1 but also comprises one or more of marker loci SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, and SEQ ID NO: 85. In other embodiments, the segment is flanked by marker loci SEQ ID NO: 1 and SEQ ID NO: 5 on chromosome 1 but also comprises one or more of marker loci SEQ ID NO: 2, SEQ ID NO: 3, and SEQ ID NO: 4. In some embodiments, the segment is flanked by marker loci SEQ ID NO: 14 and SEQ ID NO: 21 on chromosome 3 but also comprises one or more of marker loci SEQ ID NO: 15, SEQ ID NO: 16, SEQ ID NO: 17, or SEQ ID NO: 18, SEQ ID NO: 19, and SEQ ID NO: 20. In other embodiments, the segment is flanked by marker loci SEQ ID NO: 87 and SEQ ID NO: 25 on chromosome 5 but also comprises one or more of marker loci SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 23, and SEQ ID NO: 24. In some embodiments, the segment is flanked by marker loci SEQ ID NO: 26 and SEQ ID NO: 29 on chromosome 5 but also comprises one or more of marker loci SEQ ID NO: 27 and SEQ ID NO: 28. In other embodiments, the segment is flanked by marker loci SEQ ID NO: 110 and SEQ ID NO: 168 on chromosome 6 but also comprises one or more of marker loci SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 32, SEQ ID NO: 33, SEQ ID NO: 34, SEQ ID NO: 35, SEQ ID NO: 36, SEQ ID NO: 37, SEQ ID NO: 38, and SEQ ID NO: 39. In some embodiments, the segment is flanked by marker loci SEQ ID NO: 184 and SEQ ID NO: 46 on chromosome 10 but also comprises one or more of marker loci SEQ ID NO: 45, SEQ ID NO: 185, SEQ ID NO: 186, SEQ ID NO: 187, SEQ ID NO: 188, SEQ ID NO: 189, SEQ ID NO: 190, and SEQ ID NO: 191. In further embodiments, the polymorphic locus comprises a nucleic acid sequence selected from the group consisting of SEQ ID NOs: 1-191.

In some embodiments of the invention, introgressing comprises backcrossing. Other embodiments comprise introgressing at least two southern rust resistance alleles into the plant. In yet further embodiments, introgressing comprises marker-assisted selection. In still further embodiments, introgressing comprises assaying for said southern rust resistance. In certain embodiments, the plant is an $F_2$-$F_8$ progeny plant.

In another aspect, the invention provides methods of producing a corn plant with enhanced southern rust resistance comprising: a) providing a population of corn plants; b) detecting in said population the presence of a southern rust resistance allele at a polymorphic locus genetically linked to a chromosomal segment flanked by: marker loci SEQ ID NO: 48 and SEQ ID NO: 86 on chromosome 1; marker loci SEQ ID NO: 1 and SEQ ID NO: 5 on chromosome 1; marker loci SEQ ID NO: 14 and SEQ ID NO: 21 on chromosome 3; marker loci SEQ ID NO: 87 and SEQ ID NO: 25 on chromosome 5; marker loci SEQ ID NO: 26 and SEQ ID NO: 29 on chromosome 5; marker loci SEQ ID NO: 110 and SEQ ID NO: 168 on chromosome 6; or marker loci SEQ ID NO: 184 and SEQ ID NO: 46 on chromosome 10; and c) selecting from said population at least a first plant comprising said allele, wherein the allele confers enhanced resistance to southern rust compared to a plant lacking said allele. In some embodiments, the segment is flanked by marker loci SEQ ID NO: 48 and SEQ ID NO: 86 on chromosome 1, by marker loci SEQ ID NO: 1 and SEQ ID NO: 5 on chromosome 1, by marker loci SEQ ID NO: 14 and SEQ ID NO: 21 on chromosome 3, by marker loci SEQ ID NO: 87 and SEQ ID NO: 25 on chromosome 5, by marker loci SEQ ID NO: 26 and SEQ ID NO: 29 on chromosome 5, by marker loci SEQ ID NO: 110 and SEQ ID NO: 168 on chromosome 6, or by marker loci SEQ ID NO: 184 and SEQ ID NO: 46 on chromosome 10. In further embodiments, said chromosomal segment comprises a nucleic acid sequence selected from the group consisting of SEQ ID NOs: 1-191.

In yet further embodiments of the invention, providing said population of corn plants comprises crossing a corn plant comprising at least a first southern rust resistance allele with a second corn plant of a different genotype lacking said allele to produce progeny plants. The population of corn plants may comprise $F_2$-$F_6$ progeny plants. In other embodiments, providing said population comprises backcrossing. In certain embodiments, the backcrossing comprises marker-assisted selection in at least two generations. In further embodiments, the backcrossing comprises marker-assisted selection in all generations. In other embodiments, methods provided by the invention comprise assaying the first plant comprising said allele or a progeny thereof comprising the allele for said southern rust resistance.

DETAILED DESCRIPTION OF THE INVENTION

I. Chromosome Intervals

The term "chromosome interval" designates a contiguous linear span of genomic DNA that resides in planta on a single chromosome. The term also designates any and all genomic intervals defined by any of the markers set forth in this invention. The genetic elements located on a single chromosome interval are physically linked and the size of a chromosome interval is not particularly limited. In some aspects, the genetic elements located within a single chromosome interval are genetically linked, typically with a genetic recombination distance of, for example, less than or equal to 20 cM, or alternatively, less than or equal to 10 cM. That is, two genetic elements within a single chromosome interval undergo meiotic recombination at a frequency of less than or equal to 20% or 10%, respectively.

The boundaries of a chromosome interval can be defined by genetic recombination distance or by markers. In one embodiment, the boundaries of a chromosome interval comprise markers. In another embodiment, the boundaries of a chromosome interval comprise markers that will be linked to the gene controlling the trait of interest, i.e., any marker that lies within a given interval, including the terminal markers that defining the boundaries of the interval, and that can be used as a marker for the presents or absence of disease resistance. In one embodiment, the intervals described herein encompass marker clusters that co-segregate with disease resistance. The clustering of markers occurs in relatively small domains on the chromosomes, indicating the presence of a genetic locus controlling the trait of interest in those chromosome regions. The interval encompasses markers that map within the interval as well as the markers that define the terminal.

An interval described by the terminal markers that define the endpoints of the interval will include the terminal markers and any marker localizing within that chromosome domain, whether those markers are currently known or unknown. Although it is anticipated that one skilled in the art may describe additional polymorphic sites at marker loci in and around the markers identified herein, any marker within the chromosome intervals described herein that are associated with disease resistance fall within the scope of this claimed invention.

"Quantitative trait loci" or a "quantitative trait locus" (QTL) is a genetic domain that effects a phenotype that can be described in quantitative terms and can be assigned a "phenotypic value" which corresponds to a quantitative value for the phenotypic trait. A QTL can act through a single gene mechanism or by a polygenic mechanism. In some aspects, the invention provides QTL chromosome intervals, where a QTL (or multiple QTLs) that segregates with disease resistance is contained in those intervals. In one embodiment of this invention, the boundaries of chromosome intervals are drawn to encompass markers that will be linked to one or more QTL. In other words, the chromosome interval is drawn such that any marker that lies within that interval (including the terminal markers that define the boundaries of the interval) is genetically linked to the QTL. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

SR_1.01; SR_1.02; SR_3.01; SR_5.01; SR_5.02; SR_6.01; and SR_10.01 Chromosome Intervals In one embodiment, the present invention provides a plant comprising a nucleic acid molecule selected from the group consisting of SEQ ID NOs: 1-191, fragments thereof, and complements of both. In another embodiment, the present invention also provides a plant comprising the alleles of the SR_1.01; SR_1.02; SR_3.01; SR_5.01; SR_5.02; SR_6.01; or SR_10.01 chromosome intervals, or fragments and complements thereof, as well as any plant comprising any combination of one or more disease resistance loci linked to at least one marker selected from the group consisting of SEQ ID NOs: 1-191. Such alleles may be homozygous or heterozygous.

The locations in the maize genome of SR_1.01; SR_1.02; SR_3.01; SR_5.01; SR_5.02; SR_6.01; or SR_10.01 and the chromosome intervals comprising markers closely linked to it are disclosed in Table 5. Genetic map loci are represented in cM, with position zero being the first (most distal) marker known at the beginning of the chromosome on both a proprietary consensus genetic map and the Neighbors 2008 maize genomic map, which is freely available to the public from the Maize GDB website and commonly used by those skilled in the art.

For example, the SR_1.01 chromosome interval comprises SEQ ID NOs: 48-86, and is flanked by the markers SEQ ID NO: 48 and SEQ ID NO: 86. In certain embodiments, the invention provides chromosome intervals associated with SR resistance between 201.5 IcM-255.9 IcM on chromosome 1, for example intervals flanked by marker loci SEQ ID NO: 48 and SEQ ID NO: 86. These chromosome intervals encompasses a marker cluster that co-segregates with SR resistance in the populations studied.

Similarly, the SR_1.02 chromosome interval contains SEQ ID NOs: 1-5, and is flanked by the markers SEQ ID NO: 1 and SEQ ID NO: 5. In certain embodiments, the invention provides chromosome intervals associated with SR resistance between 306.1 IcM-404.1 IcM on chromosome 1, for example intervals flanked by marker loci SEQ ID NO: 1 and SEQ ID NO: 5. These chromosome intervals encompasses a marker cluster that co-segregates with SR resistance in the populations studied.

The SR_3.01 chromosome interval contains SEQ ID NOs: 14-21, and is flanked by the markers SEQ ID NO: 14 and SEQ ID NO: 21. In certain embodiments, the invention provides chromosome intervals associated with SR resistance between 181.9 IcM-230 IcM on chromosome 3, for example intervals flanked by marker loci SEQ ID NO: 14 and SEQ ID NO: 21. These chromosome intervals encompasses a marker cluster that co-segregates with SR resistance in the populations studied.

The SR_5.01 chromosome interval contains SEQ ID NOs: 23-25 and SEQ ID NOs: 87-109, and is flanked by the markers SEQ ID NO: 87 and SEQ ID NO: 25. In certain embodiments, the invention provides chromosome intervals associated with SR resistance at 372.9 IcM-457.7 IcM on chromosome 5, for example intervals flanked by marker loci SEQ ID NO: 87 and SEQ ID NO: 25. These chromosome intervals encompasses a marker cluster that co-segregates with SR resistance in the populations studied.

The SR_5.02 chromosome interval contains SEQ ID NOs: 26-29, and is flanked by the markers SEQ ID NO: 26 and SEQ ID NO: 29. In certain embodiments, the invention provides chromosome intervals associated with SR resistance between 524.5 IcM-558.5 IcM on chromosome 5, for example intervals flanked by marker loci SEQ ID NO: 26 and SEQ ID NO: 29. These chromosome intervals encompasses a marker cluster that co-segregates with SR resistance in the populations studied.

The SR_6.01 chromosome interval contains SEQ ID NOs: 32-39 and SEQ ID NOs: 110-168, and is flanked by the markers SEQ ID NO: 110 and SEQ ID NO: 168. In certain embodiments, the invention provides chromosome intervals associated with SR resistance between 36.9 IcM-112 IcM on chromosome 6, for example intervals flanked by marker loci SEQ ID NO: 110 and SEQ ID NO: 168. These chromosome intervals encompasses a marker cluster that co-segregates with SR resistance in the populations studied.

The SR_10.01 chromosome interval contains SEQ ID NOs: 45-46 and SEQ ID NOs: 184-191, and is flanked by the markers SEQ ID NO: 184 and SEQ ID NO: 46. In certain embodiments, the invention provides chromosome intervals associated with SR resistance between 34.8 IcM-57.5 IcM on chromosome 10, for example intervals flanked by marker loci SEQ ID NO: 184 and SEQ ID NO: 46. These chromosome intervals encompasses a marker cluster that co-segregates with SR resistance in the populations studied.

Thus, one skilled in the art can use this invention to improve the efficiency of breeding for improved disease resistance in maize by associating disease resistance phenotypes with genotypes at previously unknown disease resistance loci in the maize genome. Disclosed herein are chromosome intervals that comprise alleles responsible for phenotypic differences between disease resistant and disease susceptible corn lines. Each chromosome interval is characterized by the genomic regions flanked by and including the markers SEQ ID NO: 48 and SEQ ID NO: 86 on chromosome 1; or SEQ ID NO: 1 and SEQ ID NO: 5 on chromosome 1; or SEQ ID NO: 14 and SEQ ID NO: 21 on chromosome 3; or SEQ ID NO: 87 and SEQ ID NO: 25 on chromosome 5; or SEQ ID NO: 26 and SEQ ID NO: 29 on chromosome 5; SEQ ID NO: 110 and SEQ ID NO: 168 on chromosome 6; or SEQ ID NO: 184 and SEQ ID NO: 46 on chromosome 10, and comprise markers within or closely linked to (within 20 cM of) SR_1.01; SR_1.02; SR_3.01; SR_5.01; SR_5.02; SR_6.01; or SR_10.01, respectively. The invention also comprises other intervals genetically linked with those intervals.

Examples of markers useful for this purpose comprise the SNP markers listed in Tables 3 and 4, or any marker that maps within the chromosome intervals described herein (including the termini of the intervals), or any marker linked to those markers. Such markers can be assayed simultaneously or sequentially in a single sample or population of samples.

Accordingly, the markers and methods of the present invention can be utilized to guide MAS or breeding maize varieties with the desired complement (set) of allelic forms of chromosome intervals associated with superior agronomic performance (resistance, along with any other available markers for yield, disease resistance, etc.). Any of the disclosed marker alleles can be introduced into a corn line via introgression, by traditional breeding (or introduced via transformation, or both) to yield a corn plant with superior agronomic performance. The number of alleles associated with resistance that can be introduced or be present in a corn plant of the present invention ranges from one to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein could be useful and within the scope of this invention.

Similarly, by identifying plants lacking the desired marker locus, susceptible or less resistant plants can be identified, and, e.g., eliminated from subsequent crosses. Similarly, these marker loci can be introgressed into any desired genomic background, germplasm, plant, line, variety, etc., as part of an overall MAS breeding program designed to enhance yield. The invention also provides chromosome QTL intervals that find equal use in MAS to select plants that demonstrate disease resistance or improved tolerance. Similarly, the QTL intervals can also be used to counter-select plants that are susceptible or have reduced resistance to disease.

The present invention also comprises methods of making a progeny corn plant and the progeny corn plants produced by these methods. The methods comprise crossing a first parent corn plant with a second corn plant and growing the female corn plant under plant growth conditions to yield corn plant progeny. Methods of crossing and growing corn plants are well within the ability of those of ordinary skill in the art. Such corn plant progeny can be assayed for alleles associated with resistance and, thereby, the desired progeny selected. Such progeny plants or seed can be sold commercially for corn production, used for food, processed to obtain a desired constituent of the corn, or further utilized in subsequent rounds of breeding. At least one of the first or second corn plants is a corn plant of the present invention in that it comprises at least one of the allelic forms of the markers of the present invention, such that the progeny are capable of inheriting the allele.

Often, a method of the present invention is applied to at least one related corn plant such as from progenitor or descendant lines in the subject corn plants' pedigree such that inheritance of the desired resistance allele can be traced. The number of generations separating the corn plants being subject to the methods of the present invention will generally be from 1 to 20, commonly 1 to 5, and typically 1, 2, or 3 generations of separation, and quite often a direct descendant or parent of the corn plant will be subject to the method (i.e., one generation of separation).

Thus, with this invention, one skilled in the art can detect the presence or absence of disease resistance genotypes in the genomes of corn plants as part of a marker assisted selection program. In one embodiment, a breeder ascertains the genotype at one or more markers for a disease resistant parent, which contains a disease resistance allele, and the genotype at one or more markers for a susceptible parent, which lacks the resistance allele. For example, the markers of the present invention can be used in MAS in crosses involving elite x exotic corn lines by subjecting the segregating progeny to MAS to maintain disease resistance alleles, or alleles associated with yield under disease conditions. A breeder can then reliably track the inheritance of the resistance alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the disease resistant parent can be reliably predicted to express the resistant phenotype; progeny that share genotypes with the disease susceptible parent can be reliably predicted to express the susceptible phenotype. Thus, the laborious and inefficient process of manually phenotyping the progeny for disease resistance is avoided.

By providing the positions in the maize genome of the intervals and the disease resistance associated markers within, this invention also allows one skilled in the art to identify other markers within the intervals disclosed herein or linked to the chromosome intervals disclosed herein.

Closely linked markers flanking the locus of interest that have alleles in linkage disequilibrium with a resistance allele at that locus may be effectively used to select for progeny plants with enhanced resistance to disease conditions. Thus, the markers described herein, such as those listed in Tables 3 and 4, as well as other markers genetically or physically mapped to the same chromosome interval, may be used to select for maize plants with enhanced resistance to disease conditions. Typically, a set of these markers will be used, (e.g., 2 or more, 3 or more, 4 or more, 5 or more) in the flanking region above the gene and a similar set in the flanking region below the gene. Optionally, as described above, a marker within the actual gene and/or locus may also be used. The parents and their progeny are screened for these sets of markers, and the markers that are polymorphic between the two parents are used for selection. In an introgression program, this allows for selection of the gene or locus genotype at the more proximal polymorphic markers and selection for the recurrent parent genotype at the more distal polymorphic markers.

The choice of markers actually used to practice this invention is not particularly limited and can be any marker that maps within the SR_1.01; SR_1.02; SR_3.01; SR_5.01; SR_5.02; SR_6.01; or SR_10.01 chromosome intervals described herein, any marker closely linked (within 10 cM) to a marker in the SR_1.01; SR_1.02; SR_3.01; SR_5.01; SR_5.02; SR_6.01; or SR_10.01 chromosome intervals, or any marker selected from SEQ ID NOs: 1-191, or the markers listed in Tables 3 and 4. Furthermore, since there are many different types of marker detection assays known in the art, it is not intended that the type of marker detection assay (e.g. RAPDs, RFLPs, SNPs, AFLPs, etc.) used to practice this invention be limited in any way.

II. Molecular Genetic Markers

"Marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

"Marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A favorable allele of a marker is the allele of the marker that co-segregates with a desired phenotype (e.g., disease resistance). As used herein, a QTL marker has a minimum of one favorable allele, although it is possible that the marker might have two or more favorable alleles found in the population. Any favorable allele of that marker can be used advantageously for the identification and construction of disease resistant plant lines. Optionally, one, two, three or more favorable allele(s) of different markers are identified in, or introgressed into a plant, and can be selected for or against during MAS. Desirably, plants or germplasm are identified that have at least one such favorable allele that positively correlates with disease resistance or improved disease resistance. Alternatively, a marker allele that co-segregates with disease susceptibility also finds use with the invention, since that allele can be used to identify and counter select disease susceptible plants. Such an allele can be used for exclusionary purposes during breeding to identify alleles that negatively correlate with resistance, to eliminate susceptible plants or germplasm from subsequent rounds of breeding.

The more tightly linked a marker is with a DNA locus influencing a phenotype, the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype.

Genetic markers are distinguishable from each other (as well as from the plurality of alleles of anyone particular marker) on the basis of polynucleotide length and/or sequence. A large number of corn molecular markers are known in the art, and are published or available from various sources, such as the MaizeGDB Internet resource. In general, any differentially inherited polymorphic trait (including a nucleic acid polymorphism) that segregates among progeny is a potential genetic marker.

In some embodiments of the invention, one or more marker alleles are selected for in a single plant or a population of plants. In these methods, plants are selected that contain favorable alleles from more than one resistance marker, or alternatively, favorable alleles from more than one resistance marker are introgressed into a desired germplasm. One of skill recognizes that the identification of favorable marker alleles is germplasm-specific. The determination of which marker alleles correlate with resistance (or susceptibility) is determined for the particular germplasm under study. One of skill recognizes that methods for identifying the favorable alleles are known in the art. Identification and use of such favorable alleles is within the scope of this invention. Furthermore still, identification of favorable marker alleles in plant populations other than the populations used or described herein is within the scope of this invention.

Marker Detection

In some aspects, methods of the invention utilize an amplification step to detect/genotype a marker locus, but amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

"Amplifying," in the context of nucleic acid amplification, is any process whereby additional copies of a selected nucleic acid (or a transcribed form thereof) are produced. In some embodiments, an amplification based marker technology is used wherein a primer or amplification primer pair is admixed with genomic nucleic acid isolated from the first plant or germplasm, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. In other embodiments, plant RNA is the template for the amplification reaction. In some embodiments, the QTL marker is a SNP type marker, and the detected allele is a SNP allele, and the method of detection is allele specific hybridization (ASH).

In general, the majority of genetic markers rely on one or more property of nucleic acids for their detection. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like). A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In one embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

While the exemplary markers provided in the figures and tables herein are either SNP markers, any of the aforementioned marker types can be employed in the context of the invention to identify chromosome intervals encompassing genetic element that contribute to superior agronomic performance (e.g., disease resistance or improved disease tolerance).

Probes and Primers

In general, synthetic methods for making oligonucleotides, including probes, primers, molecular beacons, PNAs, LNAs (locked nucleic acids), etc., are known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon. It is not intended that the nucleic acid probes of the invention be limited to any particular size.

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers." It will be appreciated that, although many specific examples of primers are provided herein, suitable primers to be used with the invention can be designed using any suitable method. It is not intended that the invention be limited to any particular primer or primer pair. In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited herein also find use with the present invention.

III. Linkage Analysis and QTL

Linkage Analysis

"Linkage", or "genetic linkage," is used to describe the degree with which one marker locus is "associated with" another marker locus or some other locus (for example, a resistance locus). For example, if locus A has genes "A" or "a" and locus B has genes "B" or "b" and a cross between parent 1 with AABB and parent 2 with aabb will produce four possible gametes where the genes are segregated into AB, Ab, aB and ab. The null expectation is that there will be independent equal segregation into each of the four possible genotypes, i.e. with no linkage 1/4 of the gametes will of each genotype. Segregation of gametes into a genotypes differing from ¼ is attributed to linkage. As used herein, linkage can be between two markers, or alternatively between a marker and a phenotype. A marker locus can be associated with (linked to) a trait, e.g., a marker locus can be associated with resistance or improved tolerance to a plant pathogen when the marker locus is in linkage disequilibrium (LD) with the resistance trait. The degree of linkage of a molecular marker to a phenotypic trait (e.g., a QTL) is measured, e.g., as a statistical probability of co-segregation of that molecular marker with the phenotype.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1. The phrase "closely linked," in the present application, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 20, 19, 18, 17, 16, 15, 14, 13, 12, 11, 10, 9, 8, 7, 6, 5, 4, 3, 2, 1, 0.75, 0.5 or 0.25 cM or less from each other.

Classical linkage analysis can be thought of as a statistical description of the relative frequencies of co segregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in the marker and the DNA sequence responsible for the trait the marker is designed to track segregating separately into progeny. A common measure of linkage is the frequency with which traits cosegregate. This can be expressed as a percentage of cosegregation (recombination frequency) or, also commonly, in centiMorgans (cM).

Linkage analysis is used to determine which polymorphic marker allele demonstrates a statistical likelihood of cosegregation with the resistance phenotype (thus, a "resistance marker allele"). Following identification of a marker allele for co-segregation with the resistance phenotype, it is possible to use this marker for rapid, accurate screening of plant lines for the resistance allele without the need to grow the plants through their life cycle and await phenotypic evaluations, and furthermore, permits genetic selection for the particular resistance allele even when the molecular identity of the actual resistance QTL is unknown. Tissue samples can be taken, for example, from the endosperm, embryo, or mature/developing plant and screened with the appropriate molecular marker to rapidly determine determined which progeny contain the desired genetics. Linked markers also remove the impact of environmental factors that can often influence phenotypic expression.

Because chromosomal distance is approximately proportional to the frequency of crossing over events between traits, there is an approximate physical distance that correlates with recombination frequency. Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

Quantitative Trait Loci

An allele of a QTL can comprise multiple genes or other genetic factors even within a contiguous genomic region or linkage group, such as a haplotype. As used herein, an allele of a disease resistance locus can encompass more than one gene or nucleotide sequence where each individual gene or nucleotide sequence is also capable of exhibiting allelic variation and where each gene or nucleotide sequence is also capable of eliciting a phenotypic effect on the quantitative trait in question. In an aspect of the present invention the allele of a QTL comprises one or more genes or nucleic acid sequences that are also capable of exhibiting allelic variation. The use of the term "an allele of a QTL" is thus not intended to exclude a QTL that comprises more than one gene or other genetic factor. Specifically, an "allele of a QTL" in the present in the invention can denote a haplotype within a haplotype window wherein a phenotype can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular disease locus or for a particular polymorphic marker.

The principles of QTL analysis and statistical methods for calculating linkage between markers and useful QTL, or between any loci in a genome are well known in the art. Exemplary methods include penalized regression analysis, ridge regression, single point marker analysis, complex pedigree analysis, Bayesian MCMC, identity-by-descent analysis, interval mapping, composite interval mapping, and Haseman-Elston regression. QTL analyses are often performed with the help of a computer and specialized software available from a variety of public and commercial sources known to those of skill in the art.

IV. Genetic Mapping

A "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM). In some cases, two different markers can have the same genetic map coordinates. In that case, the two markers are in such close proximity to each other that recombination occurs between them with such low frequency that it is undetected.

Genetic maps are graphical representations of genomes (or a portion of a genome such as a single chromosome) where the distances between markers are measured by the recombination frequencies between them. Plant breeders use genetic maps of molecular markers to increase breeding efficiency through Marker assisted selection (MAS), a process where selection for a trait of interest is not based on the trait itself but rather on the genotype of a marker linked to the trait. A molecular marker that demonstrates reliable linkage with a phenotypic trait provides a useful tool for indirectly selecting the trait in a plant population, especially when accurate phenotyping is difficult, slow, or expensive.

In general, the closer two markers or genomic loci are on the genetic map, the closer they lie to one another on the physical map. A lack of precise proportionality between cM distances and physical distances can exist due to the fact that the likelihood of genetic recombination is not uniform throughout the genome; some chromosome regions are cross-over "hot spots," while other regions demonstrate only rare recombination events, if any.

Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in guiding MAS.

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the invention be limited to any particular mapping populations, use of any particular software, or any particular set of software parameters to determine linkage of a particular marker or chromosome interval with the disease resistance phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure.

Association Mapping

Association or LD mapping techniques aim to identify genotype-phenotype associations that are significant. It is effective for fine mapping in outcrossing species where frequent recombination among heterozygotes can result in rapid LD decay. LD is non-random association of alleles in a collection of individuals, reflecting the recombinational history of that region. Thus, LD decay averages can help determine the number of markers necessary for a genome-wide association study to generate a genetic map with a desired level of resolution.

Large populations are better for detecting recombination, while older populations are generally associated with higher levels of polymorphism, both of which contribute to accelerated LD decay. However, smaller effective population sizes tend to show slower LD decay, which can result in more extensive haplotype conservation. Understanding of the relationships between polymorphism and recombination is useful in developing strategies for efficiently extracting information from these resources. Association analyses compare the plants' phenotypic score with the genotypes at the various loci. Subsequently, any suitable maize genetic map (for example, a composite map) can be used to help observe distribution of the identified QTL markers and/or QTL marker clustering using previously determined map locations of the markers.

V. Marker Assisted Selection, Plant Breeding, and Genomic Introgression

Marker Assisted Selection

"Introgression" refers to the transmission of a desired allele of a genetic locus from one genetic background to another by plant breeding methods and/or by molecular genetic methods. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. Additionally, molecular genetic method for transmission of the desired allele include, but are not limited to, various plant transformation techniques and/or methods that provide for homologous recombination, non-homologous recombination, site-specific recombination, and/or genomic modifications that provide for locus substitution or locus conversion.

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that are resistant, exhibit improved resistance or are susceptible to SR infection by identifying plants having a specified allele that is linked to SR_1.01; SR_1.02; SR_3.01; SR_5.01; SR_5.02; SR_6.01; or SR_10.01.

In general, MAS uses polymorphic markers that have been identified as having a significant likelihood of co-segregation with a resistance trait. Such markers are presumed to map near a gene or genes that give the plant its resistance phenotype, and are considered indicators for the desired trait, and are termed QTL markers. Plants are tested for the presence or absence of a desired allele in the QTL marker.

Identification of plants or germplasm that include a marker locus or marker loci linked to a resistance trait or traits provides a basis for performing marker assisted selection. Plants that comprise favorable markers or favorable alleles are selected for, while plants that comprise markers or alleles that are negatively correlated with resistance can be selected against. Desired markers and/or alleles can be introgressed into plants having a desired (e.g., elite or exotic) genetic background to produce an introgressed resistant plant or germplasm. In some aspects, it is contemplated that a plurality of resistance markers are sequentially or simultaneous selected and/or introgressed. The combinations of resistance markers that are selected for in a single plant is not limited, and can include any combination of markers disclosed herein or any marker linked to the markers disclosed herein, or any markers located within the QTL intervals defined herein.

In some embodiments, the allele that is detected is a favorable allele that positively correlates with disease resistance or improved disease tolerance. In the case where more than one marker is selected, an allele is selected for each of the markers; thus, two or more alleles are selected. In some embodiments, it can be the case that a marker locus will have more than one advantageous allele, and in that case, either allele can be selected. It will be appreciated that the ability to identify QTL marker loci alleles that correlate with resistance, improved tolerance, or susceptibility of a corn plant to disease conditions provides a method for selecting plants that have favorable marker loci as well. That is, any plant that is identified as comprising a desired marker locus (e.g., a marker allele that positively correlates with resistance) can be selected for, while plants that lack the locus, or that have a locus that negatively correlates with resistance, can be selected against.

In some embodiments, a disease resistant first corn plant or germplasm (the donor) can be crossed with a second corn plant or germplasm (the recipient, e.g., an elite or exotic corn, depending on characteristics that are desired in the progeny) to create an introgressed corn plant or germplasm as part of a breeding program designed to improve disease resistance of the recipient corn plant or germplasm. In some aspects, the recipient plant can also contain one or more disease resistant loci, which can be qualitative or quantitative trait loci. In another aspect, the recipient plant can contain a transgene.

In some embodiments, the recipient corn plant or germplasm will typically display reduced resistance to disease conditions as compared to the first corn plant or germplasm, while the introgressed corn plant or germplasm will display an increased resistance to disease conditions as compared to the second plant or germplasm. An introgressed corn plant or germplasm produced by these methods are also a feature of this invention.

MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When a population is segregating for multiple loci affecting one or multiple traits, e.g., multiple loci involved in resistance, or multiple loci each involved in resistance or tolerance to different diseases, the efficiency of MAS compared to phenotypic screening becomes even greater, because all of the loci can be evaluated in the lab together from a single sample of DNA.

Marker Assisted Backcrossing

One application of MAS is to use the resistance or improved tolerance markers to increase the efficiency of an introgression effort aimed at introducing a resistance QTL into a desired (typically high yielding) background. If the nucleic acids from a plant are positive for a desired genetic marker allele, the plant can be self-fertilized to create a true breeding line with the same genotype, or it can be crossed with a plant with the same marker or with other characteristics to create a sexually crossed hybrid generation.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable resistance marker loci) into an otherwise desirable genetic background from the recurrent parent (e.g., an otherwise high yielding line). The more cycles of back crossing that are done, the greater the genetic contribution of the recurrent parent to the resulting introgressed variety. This is often necessary, because resistant plants may be otherwise undesirable, e.g., due to low yield, low fecundity, or the like. In contrast, strains which are the result of intensive breeding programs may have excellent yield, fecundity or the like, merely being deficient in one desired trait such as resistance to SR infection.

Moreover, in another aspect, while maintaining the introduced markers associated with resistance, the genetic contribution of the plant providing disease resistance can be reduced by back-crossing or other suitable approaches. In one aspect, the nuclear genetic material derived from the donor material in the plant can be less than or about 50%, less than or about 25%, less than or about 13%, less than or about 5%, 3%, 2% or 1%, but that the recipient remains resistant to disease.

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

Genomic Selection

Genomic selection (GS), also known as genome wide selection (GWS), is a form of MAS that estimates all locus, haplotype, and/or marker effects across the entire genome to calculate genomic estimated breeding values (GEBVs). See Nakaya and Isobe, *Annals of Botany* 110: 1303-1316 (2012); Van Vleck, et al., *Journal of Animal Science* 70: 363-371 (1992); and Heffner, et al., *Crop Science* 49: 1-12 (2009). GS utilizes a training phase and a breeding phase. In the training phase, genotypes and phenotypes are analyzed in a subset of a population to generate a GS prediction model that incorporates significant relationships between phenotypes and genotypes. A GS training population must be representative of selection candidates in the breeding program to which GS will be applied. In the breeding phase, genotype data are obtained in a breeding population, then favorable individuals are selected based on GEBVs obtained using the GS prediction model generated during the training phase without the need for phenotypic data.

Larger training populations typically increase the accuracy of GEBV predictions. Increasing the training population to breeding population ratio is helpful for obtaining accurate GEBVs when working with populations having high genetic diversity, small breeding populations, low heritability of traits, or large numbers of QTLs. The number of markers required for GS modeling is determined based on the rate of LD decay across the genome, which must be calculated for each specific population to which GS will be applied. In general, more markers will be necessary with faster raters of LD decay. Ideally, GS comprises at least one marker in LD with each QTL, but in practical terms one of ordinary skill in the art would recognize that this is not necessary.

With genotyping data, favorable individuals from a population can be selected based only on GEBVs. GEBVs are the sum of the estimate of genetic deviation and the weighted sum of estimates of breed effects, which are predicted using phenotypic data. Without being limiting, commonly used statistical models for prediction of GEBVs include best linear unbiased prediction (Henderson, *Biometrics* 31: 423 (1975)) and a Bayesian framework (Gianola and Fernando, *Journal of Animal Science* 63: 217-244 (1986)).

The compositions and methods of the present disclosure can be utilized for GS or breeding corn varieties with a desired complement (set) of allelic forms of chromosome intervals associated with superior agronomic performance (e.g., SR resistance). In an aspect, a corn plant or seed provided herein can be selected using genomic selection. In another aspect, SEQ ID NOs: 1-191 can be used in a method comprising genomic selection. In another aspect, a genomic selection method provided herein comprises phenotyping a population of corn plants for SR resistance using the SR infection rating scale provided in Example 1. In another aspect, a genomic selection method provided herein comprises genotyping a population of corn plants or seeds with at least one of marker loci SEQ ID NOs: 1-191.

VI. Transgenic Plants

Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the present disclosure, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant.

Regulatory elements such as promoters, leaders, enhancers, introns, and transcription termination regions (or 3' UTRs) can play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, and introns that function in plants are therefore useful for modifying plant phenotypes through genetic engineering.

As used herein, the term "intron" refers to a DNA molecule that may be isolated or identified from the genomic copy of a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron. In plants, the inclusion of some introns in constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, that splicing per se is not required, as IME in dicotyledonous plants has been shown by point mutations within the splice sites of the pat1 gene from *A. thaliana*. Multiple uses of the same intron in one plant have been shown to exhibit disadvantages. In those cases, it is necessary to have a collection of basic control elements for the construction of appropriate recombinant DNA elements.

As used herein, the term "enhancer" or "enhancer element" refers to a cis-acting regulatory element, a.k.a. cis-element, which confers an aspect of the overall expression pattern, but is usually insufficient alone to drive transcription, of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Regulatory elements may be characterized by their gene expression pattern, e.g., positive and/or negative effects, such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric. As used herein, the term "chimeric" refers to a single DNA molecule produced by fusing a first DNA molecule to a second DNA molecule, where neither the first nor the second DNA molecule would normally be contained in that configuration, i.e., fused to the other. The chimeric DNA molecule is thus a new DNA molecule not otherwise normally contained in nature. As used herein, the term "chimeric promoter" refers to a promoter produced through such manipulation of DNA molecules. A chimeric promoter may combine two or more DNA fragments, for example, the fusion of a promoter to an enhancer element. Thus, the design, construction, and use of chimeric promoters according to the methods disclosed herein for modulating the expression of operably linked transcribable DNA molecules are encompassed by the disclosure.

In specific embodiments, chimeric DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

Exemplary promoters for expression of a nucleic acid sequence include plant promoters such as the CaMV 35S promoter, or others such as CaMV 19S, nos, Adh, sucrose synthase, α-tubulin, actin, cab, PEPCase or those promoters associated with the R gene complex. Tissue-specific promoters such as leaf specific promoters, or tissue selective promoters (e.g., promoters that direct greater expression in leaf primordia than in other tissues), and tissue-specific enhancers are also contemplated to be useful, as are inducible promoters such as ABA- and turgor-inducible promoters. Any suitable promoters known in the art may be used to express defensin or defensin-like coding sequences in a plant. In an embodiment, the CaMV35S promoter may be used to express defensin or defensin-like coding sequences in a plant. In yet another embodiment, a disease or pathogen inducible promoter can be used to express defensin or defensin like proteins. Examples of disease or pathogen inducible promoters can be found in Kooshki et al. Plant Science 165 (2003) 213-219, Koschmann et al. Plant Physiology 160 (2012) 178-191, Rushton et al. The Plant Cell, 14 (2002) 749-762, and Kirsch et al. The Plant Journal (2001) 26 217-227.

The DNA sequence between the transcription initiation site and the start of the coding sequence, i.e., the untranslated leader sequence, can also influence gene expression. As used herein, the term "leader" refers to a DNA molecule from the untranslated 5' region (5' UTR) of a gene and defined generally as a DNA segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. One may thus wish to employ a particular leader sequence with a transformation construct of the present disclosure. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. In some embodiments, sequences that are derived from genes that are highly expressed in plants may be used for expression of defensin or defensin-like coding sequences.

Transformation constructs prepared in accordance with the present disclosure may further include a 3' end DNA sequence that acts as a signal to terminate transcription and allow for the polyadenylation of the mRNA produced by coding sequences operably linked to a promoter. As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR. In one embodiment, the native terminator of a defensin or defensin-like coding sequence may be used. Alternatively, a heterologous 3' end may enhance the expression of sense or antisense defensin or defensin-like coding sequences.

Sequences that are joined to the coding sequence of an expressed gene, which are removed post-translationally from the initial translation product and which facilitate the transport of the protein into or through intracellular or extracellular membranes, are termed transit or targeting peptide (usually into vacuoles, vesicles, plastids and other intracellular organelles) and signal peptide or sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein.

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the present disclosure.

Selectable marker transgenes may also be used with the present disclosure. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the present disclosure are known in the art and include, but are not limited to, transcribable DNA molecules encoding β-glucuronidase (GUS), green fluorescent protein (GFP), proteins that confer antibiotic resistance, and proteins that confer herbicide tolerance.

VII. Plant Cell Transformation Methods

Numerous methods for transforming chromosomes in a plant cell with recombinant DNA are known in the art and are used in methods of producing a transgenic plant cell and plant. Two effective methods for such transformation are Agrobacterium-mediated transformation and microprojectile bombardment-mediated transformation. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). Agrobacterium-mediated transformation methods are described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), and US Patent Application Publication Nos. US 2004/0087030 A1 (cotton), and US 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having another recombinant DNA that confers another trait, for example herbicide resistance or pest resistance or enhanced water use efficiency, to produce progeny plants having recombinant DNA that confers both traits. Typically, in such breeding for combining traits the transgenic plant donating the additional trait is the male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant DNA, by application using a selective agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glypho sate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

VIII. Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits, such as resistance to southern rust in maize Seed Treatment In an aspect, a method, a corn plant, or a corn seed provided herein is used in combination with one or more pesticides including, but not limited to, herbicides, fungicides (e.g., picoxystrobin, cyproconazole, tetraconazole, pyraclostrobin, metconazole, azoxystrobin, propiconazole, prothioconazole, trifloxystrobin), insecticides, microbiocides, nematicides, insect repellents, bactericides, and other substances used to control pests. In another aspect, a method, a corn plant, or a corn seed provided herein is used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which can be applied as a seed treatment, a foliar treatment, a drench treatment, or a drip treatment.

In an aspect, corn seeds provided herein are untreated. In another aspect, corn seeds provided herein can be subjected to various and multiple treatments. For example, without being limiting, the seeds can be treated to improve germination by priming the seeds, by disinfection to protect against seed borne pathogens, or both priming and disinfection. In another example, seeds can be coated with any available coating to improve, for example, plantability, seed emergence, and protection against seed borne pathogens. Seed coating can be any form of seed coating including, but not limited to, pelleting, film coating, and encrustments.

IX. General Terms and Definitions

Systems, including automated systems for selecting plants that comprise a marker of interest and/or for correlating presence of the marker with resistance are also a feature of the invention. These systems can include probes relevant to marker locus detection, detectors for detecting labels on the probes, appropriate fluid handling elements and temperature controllers that mix probes and templates and/or amplify templates and systems instructions that correlate label detection to the presence of a particular marker locus or allele.

In an aspect, this invention could be used on any plant. In another aspect, the plant is selected from the genus *Zea*. In another aspect, the plant is selected from the species *Zea mays*. In a further aspect, the plant is selected from the subspecies *Zea mays* L. ssp. *mays*. In an additional aspect, the plant is selected from the group *Zea mays* L. subsp. *mays* Indentata, otherwise known as dent corn. In another aspect, the plant is selected from the group *Zea mays* L. subsp. *mays* Indurata, otherwise known as flint corn. In an aspect, the plant is selected from the group *Zea mays* L. subsp. *mays* Saccharata, otherwise known as sweet corn. In another aspect, the plant is selected from the group *Zea mays* L. subsp. *mays* Amylacea, otherwise known as flour corn. In a further aspect, the plant is selected from the group *Zea mays* L. subsp. *mays* Everta, otherwise known as pop corn. *Zea* plants include hybrids, inbreds, partial inbreds, or members of defined or undefined populations.

In a preferred aspect, the present invention provides a plant to be assayed for resistance or susceptibility to disease by any method to determine whether a plant is resistant, susceptible, or whether it exhibits some degree of resistance or susceptibility. Populations of plants can be similarly characterized in this manner, or further characterized as segregating for the trait of disease resistance.

It is further understood that a plant of the present invention may exhibit the characteristics of any relative maturity group. In an aspect, the maturity group is selected from the group consisting of early maturing varieties, mid-season maturing varieties, and full season varieties.

The present invention also provides for parts of the plants of the present invention. Plant parts, without limitation, include seed, endosperm, ovule and pollen. In a particularly preferred aspect of the present invention, the plant part is a seed.

In another aspect, the corn seed can be subjected to various treatments. For example, the seeds can be treated to improve germination by priming the seeds or by disinfection to protect against seed-borne pathogens. In another aspect, seeds can be coated with any available coating to improve, for example, plantability, seed emergence, and protection against seed-borne pathogens. Seed coating can be any form of seed coating including, but not limited to, pelleting, film coating, and encrustments.

In another aspect, the corn plant can show a comparative resistance compared to a non-resistant control corn plant. In this aspect, a control corn plant will preferably be genetically similar except for the disease resistance allele or alleles in question. Such plants can be grown under similar conditions with equivalent or near equivalent exposure to the pathogen.

Various patent and non-patent publications are cited herein, the disclosures of each of which are incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

Descriptions of commonly used breeding terms and methods for crossing and producing hybrids that are used to describe present invention can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), *Center for Agricultural Publishing and Documentation,* 1979; Fehr, In: Soybeans: Improvement, Production and Uses, 2nd Edition, Monograph., 16:249, 1987; Fehr, "Principles of variety development," *Theory and Technique,* (Vol. 1) and *Crop Species Soybean* (Vol. 2), Iowa State Univ., Macmillan Pub. Co., NY, 360-376, 1987).

The definitions and methods provided define the present invention and guide those of ordinary skill in the art in the practice of the present invention. Unless otherwise noted, terms are to be understood according to conventional usage by those of ordinary skill in the relevant art. Examples of resources describing many of the terms related to molecular biology used herein can be found in in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes Icorn, Oxford University Press: New York, 2007. The nomenclature for DNA bases as set forth at 37 CFR § 1.822 is used.

Definitions

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"Adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

"Allele" generally refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease prone plants. A favorable allelic form of a chromosome interval is a chromosome interval that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indicator that the desired trait or trait form will occur in a plant comprising the allele. An allele negatively correlates with a trait when it is linked to it and when presence of the allele is an indicator that a desired trait or trait form will not occur in a plant comprising the allele.

"Crossed" or "cross" means to produce progeny via fertilization (e.g. cells, seeds or plants) and includes crosses between plants (sexual) and self-fertilization (selfing).

"Elite line" means any line that has resulted from breeding and selection for superior agronomic performance. Numerous elite lines are available and known to those of skill in the art of corn breeding. An "elite population" is an assortment of elite individuals or lines that can be used to represent the state of the art in terms of agronomically superior genotypes of a given crop species, such as corn. Similarly, an "elite germplasm" or elite strain of germplasm is an agronomically superior germplasm, typically derived from and/or capable of giving rise to a plant with superior agronomic performance, such as an existing or newly developed elite line of corn. In contrast, an "exotic line" or "exotic germplasm" is a line or germplasm derived from a plant not belonging to an available elite line or strain of germplasm. In the context of a cross between two plants or lines of germplasm, an exotic germplasm is not closely related by descent to the elite germplasm with which it is crossed. Most commonly, the exotic germplasm is not derived from any known elite line of a crop, but rather is selected to introduce genetic elements (typically desired alleles) into a breeding program.

"Exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

"Genetic element" or "gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

"Genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome interval. The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease resistance, etc. In some cases, a phenotype is directly controlled by a single gene or genetic locus, i.e., a "single gene trait." In other cases, a phenotype is the result of several genes.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

"Linkage disequilibrium" or "LD" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

"Locus" a chromosome region where a polymorphic nucleic acid, trait determinant, gene or marker is located. The loci of this invention comprise one or more polymorphisms in a population; i.e., alternative alleles are present in some individuals. A "gene locus" is a specific chromosome location in the genome of a species where a specific gene can be found.

"Marker Assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc. "Marker Assisted Selection" (MAS) is a process by which phenotypes are selected based on marker genotypes.

"Molecular phenotype" is a phenotype detectable at the level of a population of one or more molecules. Such molecules can be nucleic acids, proteins, or metabolites. A molecular phenotype could be an expression profile for one or more gene products, e.g., at a specific stage of plant development, in response to an environmental condition or stress, etc.

"Operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression.

"Percent identity" or "% identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence.

"Phenotype" means the detectable characteristics of a cell or organism which can be influenced by genotype.

"Plant" refers to a whole plant any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a resistance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

"Resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different corn line) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant lines, or plant families under disease conditions, and furthermore, will also recognize the phenotypic gradations of "resistant."

"Resistance locus" means a locus that contributes resistance, tolerance, or susceptibility to southern rust.

"Resistance allele" means the nucleic acid sequence associated with resistance or tolerance to disease.

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Tolerance" or "improved tolerance" in a plant to disease conditions is an indication that the plant is less affected by disease conditions with respect to yield, survivability and/or other relevant agronomic measures, compared to a less resistant, more "susceptible" plant. Tolerance is a relative term, indicating that a "tolerant" plant survives and/or produces better yields in disease conditions compared to a different (less tolerant) plant (e.g., a different corn line strain) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance or susceptibility of different plants, plant lines or plant families under disease conditions, and furthermore, will also recognize the phenotypic gradations of "tolerant."

"Transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Vector" is a polynucleotide or other molecule that transfers nucleic acids between cells. Vectors are often derived from plasmids, bacteriophages, or viruses and optionally comprise parts which mediate vector maintenance and enable its intended use. A "cloning vector" or "shuttle vector" or "sub cloning vector" contains operably linked parts that facilitate subcloning steps (e.g., a multiple cloning site containing multiple restriction endonuclease sites). The term "expression vector" as used herein refers to a vector comprising operably linked polynucleotide sequences that facilitate expression of a coding sequence in a particular host organism (e.g., a bacterial expression vector or a plant expression vector).

"Yield" is the culmination of all agronomic traits as determined by the productivity per unit area of a particular plant product of commercial value. "Agronomic traits," include the underlying genetic elements of a given plant variety that contribute to yield over the course of growing season.

EXAMPLES

Example 1. Phenotyping Southern Rust Disease Symptoms

Corn plants were artificially inoculated with active southern rust (SR) spores at the V8 stage. Plants were screened about 3-6 weeks after tasseling or when the average field rating was between 4-6 on the 1-9 rating scale. SR disease resistance was measured using a 1 to 9 scale, where 1 indicates no disease, 9 indicates complete plant death, and 5 indicates 50% tissue damage due to the disease.

Example 2. Identification of QTLs Associated with Southern Rust Resistance Using Bi-Parental Mapping Bi-parental mapping populations were constructed to investigate the genetic basis of SR disease resistance in corn. Resistant and susceptible parental lines were selected from proprietary inbred lines as shown in Table 1.

TABLE 1

Bi-parental mapping populations

| Mapping population | Origin | Resistant Parent | Susceptible Parent | Population Type | Number of plants | Heritability |
|---|---|---|---|---|---|---|
| A | I686684/CV799972 | CV799972 | I686684 | F2:4 | 158 | 0.77 |
| B | CV649352/CV649354 | CV649354 | CV649352 | F2:4 | 143 | 0.66 |
| C | CV786079/I283669 | I283669 | CV786079 | DH2 | 200 | 0.48 |
| D | CV875318/CV870383 | CV875318 | CV870383 | F3 | 168 | 0.42 |
| E | CV258468/CV649307 | CV258468 | CV649307 | F3 | 206 | 0.35 |
| F | CV644930/CV152769 | CV644930 | CV152769 | F3 | 205 | 0.42 |
| G | CV134767/CV292419 | CV292419 | CV134767 | F2:3 | 349 | 0.33 |
| H | CV802511/CV331660 | CV802511 | CV331660 | F2:3 | 207 | 0.43 |
| I | CV287140/CV792120 | CV287140 | CV792120 | F2:3 | 280 | 0.44 |

Plants from all mapping populations were then genotyped using SNP markers that collectively spanned each chromosome in the maize genome.

A composite interval mapping (CIM) approach was taken to identify SR resistance QTL intervals based genotyping data and on the phenotyping collected in Example 1. For each marker, the thresholds of likelihood ratio between full and null models for CIM are based on 1000 random permutation tests (Churchill and Doerg, Genetics, 138(3):963-71 (1994)). The composite interval mapping (CIM) analysis reveale several strong QTLs associated with SR resistance. The QTLs are confirmed in multiple genetic backgrounds and summarized in Table 2. Each row of Table 2 provides mapping population ID, number of SNP markers genotyped, resistant parent, chromosome position, the peak of the likelihood ratio corresponding to SR resistance, left and right flanking positions on IBM2 2008 Neighbors Genetic Map, p-value, additive effect, and the phenotypic variance ($R^2$) of individual QTL or Total QTLs.

TABLE 2

CIM results from all mapping populations.

| Mapping population | Number of Markers Genotyped | Resistant Parent | Chr | QTL Positions (IBM2008 IcM) | | | p-value* | Additive Effect | Individual QTL $R^2$ | Total QTL $R^2$ |
| | | | | Peak | Left Flank | Right Flank | | | | |
|---|---|---|---|---|---|---|---|---|---|---|
| A | 114 | CV799972 | 6 | 123.9 | 57.1 | 164.8 | 0.01 | 0.21 | 0.24 | 0.55 |
| A | 114 | CV799972 | 7 | 97.6 | 86.2 | 119.7 | 0.01 | 0.15 | 0.13 | 0.54 |
| A | 114 | CV799972 | 10 | 125.9 | 97.9 | 146.4 | 0.05 | 0.16 | 0.13 | 0.54 |
| A | 122 | CV799972 | 6 | 79.6 | 6.9 | 130.9 | 0.01 | 0.92 | 0.29 | 0.64 |
| A | 122 | CV799972 | 10 | 55.5 | 16.6 | 102.7 | 0.01 | 1.04 | 0.38 | 0.63 |

TABLE 2-continued

CIM results from all mapping populations.

| Mapping population | Number of Markers Genotyped | Resistant Parent | Chr | QTL Positions (IBM2008 IcM) Peak | Left Flank | Right Flank | p-value* | Additive Effect | Individual QTL R² | Total QTL R² |
|---|---|---|---|---|---|---|---|---|---|---|
| A | 122 | CV799972 | 6 | 79.6 | 31.3 | 106.2 | 0.01 | 1.59 | 0.34 | 0.46 |
| B | 112 | CV649354 | 6 | 18.3 | 14.3 | 118.1 | 0.01 | 0.6 | 0.65 | 0.69 |
| B | 112 | CV649354 | 6 | 35.9 | 14.3 | 118.4 | 0.01 | 0.41 | 0.49 | 0.66 |
| C | 140 | I283669 | 1 | 402.3 | 332.4 | 458.2 | 0.01 | 0.78 | 0.23 | 0.35 |
| D | 131 | CV875318 | 5 | 412.8 | 337.7 | 457.4 | 0.01 | 0.52 | 0.11 | 0.48 |
| E | 139 | CV258468 | 3 | 189.9 | 135 | 189.9 | 0.001 | 0.47 | 0.12 | 0.43 |
| E | 139 | CV258468 | 6 | 106.2 | 63.7 | 106.2 | 0.0001 | 0.59 | 0.21 | 0.39 |
| F | 145 | CV644930 | 5 | 533.7 | 533.7 | 533.7 | 0.001 | 0.53 | 0.19 | 0.45 |
| F | 145 | CV644930 | 6 | 15.2 | 15.2 | 15.2 | 0.01 | 0.36 | 0.09 | 0.41 |
| G | 158 | CV292419 | 3 | 188.5 | 173.3 | 289.4 | 0.01 | 0.42 | 0.09 | 0.46 |
| H | 152 | CV802511 | 10 | 57.5 | 57.1 | 65.8 | 0.01 | 1.5 | 0.6 | 0.6 |
| I | 149 | CV287140 | 1 | 542.9 | 520.4 | 549.4 | 0.01 | 1.2 | 0.27 | 0.27 |

*p-value is based on 1,000 permutation tests.

Single-marker analysis (SMA) was performed to identify markers associated with SR resistance using the genotypic data from Example 2. For each marker, the thresholds (p-value) for SMA are based on 10,000 random permutation tests (Churchill and Doerg, Genetics, 138(3):963-71 (1994)).

As shown in Table 3, 47 SNP markers were identified to be linked to SR disease resistance. Table 3 also provides the effect estimates on SR rating score for each marker linked to SR disease resistance. Further provided are the SEQ ID NO of the marker, chromosome position, marker position on the Neighbors 2008 maize genetic map (publicly available at the MaizeGDB website, maizegdb.org/data_center/map), genetic source of favorable allele, resistant allele SNP, susceptible allele SNP, the estimated effect that the marker polymorphism has on the SR rating score, p-value based on 10,000 random permutation tests and mapping population. For example, SEQ ID NO: 1 is associated with a 0.48 reduction in SR rating score by one copy of the resistant allele. However, one of skill in the art recognizes that a "resistant" allele at one locus can be a "susceptible" allele in a different genetic background. Thus, this disclosure is not limited to the "resistant" and "susceptible" alleles exemplified herein.

TABLE 3

Estimate effects of markers linked to SR disease resistance from bi-parental mapping populations by SMA.

| Marker (SEQ ID NO) | Chromosome | IBM2008 Map (IcM) | Genetic Source of Resistant Allele | Exemplary Resistant Allele | Exemplary Susceptible Allele | Single Allele Effect | Permutation Testing Probability | Mapping Population |
|---|---|---|---|---|---|---|---|---|
| 1 | 1 | 306.1 | CV292419 | A | G | 0.48 | 0.001 | G |
| 2 | 1 | 359.1 | I283669 | C | A | 0.37 | 0.001 | C |
| 3 | 1 | 390.6 | CV292419 | A | G | 0.47 | 0.001 | G |
| 4 | 1 | 392.6 | I283669 | A | G | 0.36 | 0.001 | C |
| 5 | 1 | 404.1 | CV292419 | A | G | 0.46 | 0.001 | G |
| 6 | 1 | 409 | I283669 | A | C | 0.34 | 0.001 | C |
| 7 | 1 | 439.5 | CV292419 | G | A | 0.39 | 0.001 | G |
| 8 | 1 | 531.7 | I283669 | A | G | 0.28 | 0.008 | C |
| 9 | 1 | 542.9 | CV287140 | C | T | 1.20 | 0.001 | I |
| 10 | 3 | 134.2 | CV258468 | A | G | 0.74 | 0.001 | E |
| 11 | 3 | 135 | CV258468 | G | C | 0.76 | 0.001 | E |
| 12 | 3 | 156.5 | CV292419 | C | T | 0.36 | 0.011 | G |
| 13 | 3 | 157.9 | CV258468 | T | A | 0.88 | 0.001 | E |
| 14 | 3 | 181.9 | CV292419 | G | A | 0.393 | 0.001 | G |
| 14 | 3 | 181.9 | CV258468 | G | A | 0.92 | 0.001 | E |
| 15 | 3 | 189.9 | CV258468 | C | G | 0.93 | 0.001 | E |
| 16 | 3 | 194.3 | CV258468 | A | C | 0.91 | 0.001 | E |
| 17 | 3 | 200.9 | CV258468 | T | C | 0.83 | 0.001 | E |
| 18 | 3 | 208.6 | CV258468 | A | G | 0.82 | 0.001 | E |
| 19 | 3 | 208.6 | CV258468 | C | T | 0.81 | 0.001 | E |
| 20 | 3 | 213.8 | CV292419 | G | T | 0.377 | 0.001 | G |
| 21 | 3 | 230 | CV292419 | A | C | 0.38 | 0.006 | G |
| 22 | 5 | 337.7 | CV875318 | T | A | 0.34 | 0.001 | D |
| 23 | 5 | 386.6 | CV875318 | A | G | 0.36 | 0.001 | D |
| 24 | 5 | 432.3 | CV875318 | C | T | 0.28 | 0.008 | D |
| 25 | 5 | 457.7 | CV875318 | A | T | 0.33 | 0.001 | D |
| 26 | 5 | 524.5 | CV644930 | G | A | 0.62 | 0.001 | F |
| 27 | 5 | 526.8 | CV644930 | A | T | 0.77 | 0.001 | F |
| 28 | 5 | 533.7 | CV644930 | A | G | 0.83 | 0.001 | F |
| 29 | 5 | 558.5 | CV644930 | T | C | 0.70 | 0.001 | F |
| 30 | 6 | 15.2 | CV799972 | A | C | 1.06 | 0.001 | A |
| 31 | 6 | 15.2 | CV799972 | C | G | 1.06 | 0.001 | A |
| 32 | 6 | 47.1 | CV799972 | T | C | 1.12 | 0.001 | A |

TABLE 3-continued

Estimate effects of markers linked to SR disease resistance from bi-parental mapping populations by SMA.

| Marker (SEQ ID NO) | Chromosome | IBM2008 Map (lcM) | Genetic Source of Resistant Allele | Exemplary Resistant Allele | Exemplary Susceptible Allele | Single Allele Effect | Permutation Testing Probability | Mapping Population |
|---|---|---|---|---|---|---|---|---|
| 33 | 6 | 73.7 | CV649354 | A | C | 0.34 | 0.001 | B |
| 34 | 6 | 78.3 | CV799972 CV649354 | G | C | 0.91 | 0.001 | A_B |
| 35 | 6 | 83.2 | CV799972 CV649354 | A | G | 0.91 | 0.001 | A_B |
| 36 | 6 | 101.9 | CV799972 CV649354 | C | T | 0.76 | 0.001 | A_B |
| 31 | 6 | 101.9 | CV799972 CV649354 | T | C | 0.76 | 0.001 | A_B |
| 38 | 6 | 106.2 | CV799972 CV649354 | T | C | 0.79 | 0.001 | A_B |
| 39 | 6 | 110.6 | CV799972 CV649354 | A | G | 0.76 | 0.001 | A_B |
| 40 | 6 | 114.2 | CV799972 CV649354 | C | T | 0.76 | 0.001 | A_B |
| 41 | 6 | 123.6 | CV799972 CV649354 | C | T | 0.78 | 0.001 | A_B |
| 42 | 6 | 128.6 | CV799972 CV649354 | C | T | 0.78 | 0.001 | A_B |
| 43 | 10 | −6.5 | CV799972 | T | C | 0.60 | 0.001 | A |
| 44 | 10 | 16.9 | CV799972 | G | A | 0.64 | 0.001 | A |
| 45 | 10 | 57.5 | CV799972 | G | T | 0.85 | 0.001 | A |
| 46 | 10 | 57.5 | CV802511 | T | G | 1.50 | 0.001 | H |
| 47 | 10 | 148.1 | CV799972 | G | C | 0.40 | 0.004 | A | lcM = map units of the IBM2 2008 Neighbors Genetic Map.

Example 3. Identification of QTLs Associated with Southern Rust Resistance by Genome-Wide Association Study (GWAS)

192 male lines and 189 female lines were phenotyped using the screening method described in Example 1. General Linear Mixed Models (GLMM) were used for GWAS, where population structure (Q matrix) and markers were fit as a fixed effect, whereas kinship (K matrix) was incorporated as the variance-covariance structure of the random effect for the individuals. Bootstrapping statistics was used to determine the threshold of significance at level of 0.01. Table 4 lists the significant markers that are associated with SR resistance via GWAS.

TABLE 4

Significant markers that are associated with SR resistance via GWAS.

| Marker (SEQ ID NO) | Chromosome | IBM2008 (lcM) | Probability | Single Marker Effects | Gender Pool |
|---|---|---|---|---|---|
| 48 | 1 | 201.5 | 0.001 | 0.73 | M |
| 49 | 1 | 202.1 | 0.001 | 0.74 | M |
| 50 | 1 | 202.4 | 0.001 | 0.77 | M |
| 51 | 1 | 203.3 | 0.001 | 0.73 | M |
| 52 | 1 | 203.3 | 0.001 | 0.72 | M |
| 53 | 1 | 203.3 | 0.001 | 0.72 | M |
| 54 | 1 | 203.3 | 0.001 | 0.73 | M |
| 55 | 1 | 210.6 | 0.001 | 0.75 | M |
| 56 | 1 | 210.6 | 0.001 | 0.72 | M |
| 57 | 1 | 211.3 | 0.001 | 0.75 | M |
| 58 | 1 | 211.5 | 0.001 | 0.75 | M |
| 59 | 1 | 215.5 | 0.001 | 0.75 | M |
| 60 | 1 | 216 | 0.001 | 0.74 | M |
| 61 | 1 | 216.5 | 0.001 | 0.74 | M |
| 62 | 1 | 216.5 | 0.001 | 0.73 | M |
| 63 | 1 | 218.5 | 0.001 | 0.72 | M |
| 64 | 1 | 223.2 | 0.001 | 0.76 | M |
| 65 | 1 | 225.4 | 0.001 | 0.76 | M |
| 66 | 1 | 225.4 | 0.001 | 0.76 | M |
| 67 | 1 | 225.4 | 0.001 | 0.73 | M |
| 68 | 1 | 225.4 | 0.001 | 0.74 | M |
| 69 | 1 | 225.4 | 0.001 | 0.74 | M |
| 70 | 1 | 225.7 | 0.001 | 0.72 | M |
| 71 | 1 | 229.5 | 0.001 | 0.73 | M |
| 72 | 1 | 229.5 | 0.001 | 0.72 | M |
| 73 | 1 | 229.5 | 0.001 | 0.74 | M |
| 74 | 1 | 229.5 | 0.001 | 0.72 | M |
| 75 | 1 | 230.2 | 0.001 | 0.75 | M |
| 76 | 1 | 231.4 | 0.001 | 0.75 | M |
| 77 | 1 | 232.2 | 0.001 | 0.76 | M |
| 78 | 1 | 232.2 | 0.001 | 0.80 | M |
| 79 | 1 | 234.4 | 0.001 | 0.78 | M |
| 80 | 1 | 236.7 | 0.001 | 0.74 | M |
| 81 | 1 | 237.9 | 0.001 | 0.76 | M |
| 82 | 1 | 251.6 | 0.001 | 0.72 | M |
| 83 | 1 | 255.2 | 0.001 | 0.74 | M |
| 84 | 1 | 255.2 | 0.001 | 0.75 | M |
| 85 | 1 | 255.2 | 0.001 | 0.72 | M |
| 86 | 1 | 255.9 | 0.001 | 0.72 | M |
| 87 | 5 | 372.9 | 0.006 | 0.68 | M |
| 88 | 5 | 378.2 | 0.009 | 0.67 | M |
| 89 | 5 | 378.2 | 0.009 | 0.67 | M |
| 90 | 5 | 380.5 | 0.001 | 0.76 | M |
| 91 | 5 | 380.5 | 0.003 | 0.68 | M |
| 92 | 5 | 384.9 | 0.003 | 0.70 | M |
| 93 | 5 | 386.3 | 0.005 | 0.70 | M |
| 94 | 5 | 386.3 | 0.004 | 0.71 | M |
| 95 | 5 | 386.3 | 0.008 | 0.69 | M |
| 96 | 5 | 386.6 | 0.004 | 0.70 | M |
| 97 | 5 | 387 | 0.001 | 0.71 | M |
| 98 | 5 | 387 | 0.001 | 0.75 | M |
| 99 | 5 | 387.4 | 0.002 | 0.71 | M |
| 100 | 5 | 387.8 | 0.001 | 0.76 | M |
| 101 | 5 | 388.2 | 0.001 | 0.78 | M |

TABLE 4-continued

Significant markers that are associated with SR resistance via GWAS.

| Marker (SEQ ID NO) | Chromosome | IBM2008 (IcM) | Probability | Single Marker Effects | Gender Pool |
|---|---|---|---|---|---|
| 102 | 5 | 393.5 | 0.002 | 0.71 | M |
| 103 | 5 | 393.8 | 0.009 | 0.67 | M |
| 104 | 5 | 394.7 | 0.001 | 0.73 | M |
| 105 | 5 | 398.3 | 0.007 | 0.68 | M |
| 106 | 5 | 400.4 | 0.001 | 0.73 | M |
| 107 | 5 | 400.4 | 0.001 | 0.75 | M |
| 108 | 5 | 400.4 | 0.001 | 0.74 | M |
| 109 | 5 | 400.4 | 0.001 | 0.75 | M |
| 110 | 6 | 36.9 | 0.001 | 0.71 | M |
| 111 | 6 | 37.8 | 0.001 | 0.72 | M |
| 112 | 6 | 55.4 | 0.004 | 0.70 | M |
| 113 | 6 | 55.4 | 0.001 | 0.76 | M |
| 114 | 6 | 60 | 0.003 | 0.71 | M |
| 115 | 6 | 61.8 | 0.002 | 0.74 | M |
| 116 | 6 | 66.4 | 0.001 | 0.96 | F |
| 117 | 6 | 73.7 | 0.007 | 0.70 | M |
| 118 | 6 | 73.7 | 0.001 | 0.87 | F |
| 119 | 6 | 73.7 | 0.001 | 0.85 | F |
| 120 | 6 | 73.7 | 0.001 | 0.87 | F |
| 121 | 6 | 73.7 | 0.001 | 0.84 | F |
| 122 | 6 | 73.7 | 0.001 | 0.87 | F |
| 123 | 6 | 74.1 | 0.007 | 0.67 | M |
| 124 | 6 | 75.8 | 0.005 | 0.71 | M |
| 125 | 6 | 76.4 | 0.001 | 0.85 | F |
| 126 | 6 | 77.5 | 0.008 | 0.70 | M |
| 127 | 6 | 78.3 | 0.001 | 0.79 | M |
| 128 | 6 | 78.8 | 0.002 | 0.77 | F |
| 129 | 6 | 80.2 | 0.001 | 0.79 | M |
| 130 | 6 | 80.2 | 0.003 | 0.72 | M |
| 131 | 6 | 80.2 | 0.005 | 0.72 | M |
| 132 | 6 | 80.2 | 0.003 | 0.72 | M |
| 133 | 6 | 80.2 | 0.005 | 0.72 | M |
| 134 | 6 | 80.7 | 0.004 | 0.77 | F |
| 135 | 6 | 81.3 | 0.003 | 0.76 | F |
| 136 | 6 | 81.3 | 0.003 | 0.76 | F |
| 137 | 6 | 82.1 | 0.009 | 0.70 | M |
| 138 | 6 | 84.4 | 0.003 | 0.75 | M |
| 138 | 6 | 84.4 | 0.001 | 0.80 | F |
| 139 | 6 | 84.4 | 0.007 | 0.71 | M |
| 139 | 6 | 84.4 | 0.001 | 0.80 | F |
| 140 | 6 | 84.4 | 0.003 | 0.75 | F |
| 141 | 6 | 84.4 | 0.002 | 0.75 | M |
| 141 | 6 | 84.4 | 0.001 | 0.80 | F |
| 142 | 6 | 84.7 | 0.003 | 0.75 | F |
| 143 | 6 | 84.7 | 0.001 | 0.80 | F |
| 144 | 6 | 84.7 | 0.001 | 0.77 | M |
| 144 | 6 | 84.7 | 0.003 | 0.77 | F |
| 145 | 6 | 84.7 | 0.002 | 0.75 | M |
| 145 | 6 | 84.7 | 0.001 | 0.80 | F |
| 146 | 6 | 84.7 | 0.001 | 0.80 | F |
| 147 | 6 | 84.7 | 0.003 | 0.76 | F |
| 148 | 6 | 84.9 | 0.001 | 0.80 | F |
| 149 | 6 | 84.9 | 0.001 | 0.79 | F |
| 150 | 6 | 84.9 | 0.002 | 0.80 | F |
| 151 | 6 | 84.9 | 0.004 | 0.76 | F |
| 152 | 6 | 84.9 | 0.001 | 0.80 | F |
| 153 | 6 | 84.9 | 0.003 | 0.76 | F |
| 154 | 6 | 84.9 | 0.003 | 0.76 | F |
| 155 | 6 | 84.9 | 0.004 | 0.75 | F |
| 156 | 6 | 84.9 | 0.001 | 0.78 | F |
| 157 | 6 | 85.2 | 0.001 | 0.79 | F |
| 158 | 6 | 85.2 | 0.001 | 0.79 | F |
| 159 | 6 | 85.2 | 0.001 | 0.79 | F |
| 160 | 6 | 123.7 | 0.004 | 0.76 | F |
| 161 | 6 | 123.7 | 0.004 | 0.76 | F |
| 162 | 6 | 102.6 | 0.002 | 0.78 | F |
| 163 | 6 | 102.6 | 0.004 | 0.76 | F |
| 164 | 6 | 103.3 | 0.007 | 0.72 | M |
| 165 | 6 | 104.8 | 0.002 | 0.78 | F |
| 166 | 6 | 110.6 | 0.007 | 0.73 | M |
| 167 | 6 | 110.6 | 0.007 | 0.72 | M |
| 168 | 6 | 112 | 0.002 | 0.75 | M |
| 169 | 10 | 7.3 | 0.001 | 0.85 | F |
| 170 | 10 | 7.3 | 0.001 | 0.85 | F |
| 171 | 10 | 8 | 0.002 | 0.78 | F |
| 172 | 10 | 13.4 | 0.002 | 0.80 | F |
| 173 | 10 | 13.4 | 0.001 | 0.82 | F |
| 174 | 10 | 16.6 | 0.001 | 0.93 | F |
| 175 | 10 | 17.4 | 0.001 | 0.88 | F |
| 176 | 10 | 19.4 | 0.001 | 0.88 | F |
| 177 | 10 | 19.7 | 0.001 | 0.78 | F |
| 178 | 10 | 30.9 | 0.001 | 0.93 | F |
| 179 | 10 | 31.2 | 0.001 | 0.80 | F |
| 180 | 10 | 31.5 | 0.001 | 0.86 | F |
| 181 | 10 | 31.8 | 0.001 | 1.19 | F |
| 182 | 10 | 34.2 | 0.001 | 0.85 | F |
| 183 | 10 | 34.5 | 0.001 | 0.93 | F |
| 184 | 10 | 34.8 | 0.001 | 0.93 | F |
| 185 | 10 | 38.4 | 0.001 | 0.97 | F |
| 186 | 10 | 40 | 0.001 | 0.90 | F |
| 187 | 10 | 35.8 | 0.001 | 0.81 | F |
| 188 | 10 | 35.8 | 0.001 | 0.93 | F |
| 189 | 10 | 36.5 | 0.001 | 0.87 | F |
| 190 | 10 | 37.2 | 0.001 | 0.89 | F |
| 191 | 10 | 37.2 | 0.001 | 0.85 | F |

IcM = map units of the IBM2 2008 Neighbors Genetic Map.

Example 4. Summary of Southern Rust QTLs

The QTLs identified from the mapping studies described above were designated SR_1.01; SR_1.02; SR_3.01; SR_5.01; SR_5.02; SR_6.01; and SR_10.01 (Table 5).

TABLE 5

Summary of SR QTLs.

| Chromosome | QTL Designation | Left Flanking Marker | IBM2008 Map Position (IcM) | Right Flanking Marker | IBM2008 Map Position (IcM) |
|---|---|---|---|---|---|
| 1 | SR_1.01 | SEQ ID NO: 48 | 201.5 | SEQ ID NO: 86 | 255.9 |
| 1 | SR_1.02 | SEQ ID NO: 1 | 306.1 | SEQ ID NO: 5 | 404.1 |
| 3 | SR_3.01 | SEQ ID NO: 14 | 181.9 | SEQ ID NO: 21 | 230 |
| 5 | SR_5.01 | SEQ ID NO: 87 | 372.9 | SEQ ID NO: 25 | 457.7 |
| 5 | SR_5.02 | SEQ ID NO: 26 | 524.5 | SEQ ID NO: 29 | 558.5 |
| 6 | SR_6.01 | SEQ ID NO: 110 | 36.9 | SEQ ID NO: 168 | 112 |
| 10 | SR_10.01 | SEQ ID NO: 184 | 34.8 | SEQ ID NO: 46 | 57.5 |

IcM = map units of the IBM2 2008 Neighbors Genetic Map

The primer sequences for amplifying exemplary SNP marker loci linked to SR disease resistance and the probes used to genotype the corresponding SNP sequences are provided in Table 6. In an illustrative example, SNP marker SEQ ID NO: 1 can be amplified using the primers described in Table 6 as SEQ ID NO: 192 (forward primer) and SEQ ID NO: 248 (reverse primer), and detected with probes indicated as SEQ ID NO: 304 (Probe 1) and SEQ ID NO: 360 (Probe 2) using a TaqMan assay. In another illustrative example, the SNP at nucleotide position 101 of SNP marker SEQ ID NO: 12 can be detected with the Infinium array method using Illumina® HD BeadChips.

One of skill in the art will recognize that sequences to either side of the given primers can be used in place of the given primers, so long as the primers can amplify a region that includes the allele to be detected. The precise probe used for detection can vary, e.g., any probe that can identify the region of a marker amplicon to be detected can be substituted for those probes exemplified herein. Configuration of the amplification primers and detection probes can also be varied. Thus, the invention is not limited to the primers, probes, or marker sequences specifically recited herein.

TABLE 6

Exemplary primers and probes used for genotyping representative SNP markers associated with SR disease resistance.

| Marker (SEQ ID NO) | SNP Position | SEQ ID NO. | | | | Marker Type |
|---|---|---|---|---|---|---|
| | | Forward Primer | Reverse Primer | Probe 1 | Probe 2 | |
| 1 | 101 | 192 | 248 | 304 | 360 | TaqMan |
| 2 | 472 | 193 | 249 | 305 | 361 | TaqMan |
| 3 | 101 | 194 | 250 | 306 | 362 | TaqMan |
| 4 | 404 | 195 | 251 | 307 | 363 | TaqMan |
| 5 | 105 | 196 | 252 | 308 | 364 | TaqMan |
| 6 | 81 | 197 | 253 | 309 | 365 | TaqMan |
| 7 | 237 | 198 | 254 | 310 | 366 | TaqMan |
| 8 | 141 | 199 | 255 | 311 | 367 | TaqMan |
| 9 | 165 | 200 | 256 | 312 | 368 | TaqMan |
| 10 | 237 | 201 | 257 | 313 | 369 | TaqMan |
| 11 | 110 | 202 | 258 | 314 | 370 | TaqMan |
| 12 | 101 | na | na | na | na | Infinium |
| 13 | 101 | 203 | 259 | 315 | 371 | TaqMan |
| 14 | 101 | 204 | 260 | 316 | 372 | TaqMan |
| 15 | 239 | 205 | 261 | 317 | 373 | TaqMan |
| 16 | 101 | 206 | 262 | 318 | 374 | TaqMan |
| 17 | 63 | 207 | 263 | 319 | 375 | TaqMan |
| 18 | 49 | 208 | 264 | 320 | 376 | TaqMan |
| 19 | 214 | 209 | 265 | 321 | 377 | TaqMan |
| 20 | 182 | 210 | 266 | 322 | 378 | TaqMan |
| 21 | 101 | na | na | na | na | Infinium |
| 22 | 288 | 211 | 267 | 323 | 379 | TaqMan |
| 23 | 244 | 212 | 268 | 324 | 380 | TaqMan |
| 24 | 280 | 213 | 269 | 325 | 381 | TaqMan |
| 25 | 150 | 214 | 270 | 326 | 382 | TaqMan |
| 26 | 106 | 215 | 271 | 327 | 383 | TaqMan |
| 27 | 52 | 216 | 272 | 328 | 384 | TaqMan |
| 28 | 322 | 217 | 273 | 329 | 385 | TaqMan |
| 29 | 101 | 218 | 274 | 330 | 386 | TaqMan |
| 30 | 378 | 219 | 275 | 331 | 387 | TaqMan |
| 31 | 68 | 220 | 276 | 332 | 388 | TaqMan |
| 32 | 84 | 221 | 277 | 333 | 389 | TaqMan |
| 33 | 130 | 222 | 278 | 334 | 390 | TaqMan |
| 34 | 437 | 223 | 279 | 335 | 391 | TaqMan |
| 35 | 235 | 224 | 280 | 336 | 392 | TaqMan |
| 36 | 299 | 225 | 281 | 337 | 393 | TaqMan |
| 37 | 248 | 226 | 282 | 338 | 394 | TaqMan |
| 38 | 333 | 227 | 283 | 339 | 395 | TaqMan |
| 39 | 914 | 228 | 284 | 340 | 396 | TaqMan |
| 40 | 233 | 229 | 285 | 341 | 397 | TaqMan |
| 41 | 101 | na | na | na | na | Infinium |
| 42 | 101 | na | na | na | na | Infinium |
| 43 | 133 | 230 | 286 | 342 | 398 | TaqMan |
| 44 | 199 | 231 | 287 | 343 | 399 | TaqMan |
| 45 | 110 | 232 | 288 | 344 | 400 | TaqMan |
| 46 | 61 | 233 | 289 | 345 | 401 | TaqMan |
| 47 | 290 | 234 | 290 | 346 | 402 | TaqMan |
| 48 | 61 | na | na | na | na | Infinium |
| 49 | 282 | na | na | na | na | Infinium |
| 50 | 61 | na | na | na | na | Infinium |
| 51 | 101 | na | na | na | na | Infinium |
| 52 | 101 | na | na | na | na | Infinium |
| 53 | 101 | na | na | na | na | Infinium |
| 54 | 101 | na | na | na | na | Infinium |
| 55 | 61 | na | na | na | na | Infinium |
| 56 | 61 | na | na | na | na | Infinium |
| 57 | 61 | na | na | na | na | Infinium |
| 58 | 61 | na | na | na | na | Infinium |
| 59 | 61 | na | na | na | na | Infinium |
| 60 | 61 | na | na | na | na | Infinium |
| 61 | 101 | na | na | na | na | Infinium |
| 62 | 101 | na | na | na | na | Infinium |
| 63 | 61 | na | na | na | na | Infinium |
| 64 | 354 | 235 | 291 | 347 | 403 | TaqMan |
| 65 | 61 | na | na | na | na | Infinium |
| 66 | 61 | na | na | na | na | Infinium |
| 67 | 101 | na | na | na | na | Infinium |
| 68 | 101 | na | na | na | na | Infinium |
| 69 | 101 | na | na | na | na | Infinium |
| 70 | 282 | 236 | 292 | 348 | 404 | TaqMan |
| 71 | 323 | 237 | 293 | 349 | 405 | TaqMan |
| 72 | 101 | na | na | na | na | Infinium |
| 73 | 101 | na | na | na | na | Infinium |
| 74 | 101 | na | na | na | na | Infinium |
| 75 | 61 | na | na | na | na | Infinium |
| 76 | 61 | na | na | na | na | Infinium |
| 77 | 61 | na | na | na | na | Infinium |
| 78 | 101 | na | na | na | na | Infinium |
| 79 | 61 | na | na | na | na | Infinium |
| 80 | 61 | na | na | na | na | Infinium |
| 81 | 101 | na | na | na | na | Infinium |
| 82 | 101 | na | na | na | na | Infinium |
| 83 | 101 | na | na | na | na | Infinium |
| 84 | 101 | 238 | 294 | 350 | 406 | TaqMan |
| 85 | 101 | na | na | na | na | Infinium |
| 86 | 486 | 239 | 295 | 351 | 407 | TaqMan |
| 87 | 61 | na | na | na | na | Infinium |
| 88 | 61 | na | na | na | na | Infinium |
| 89 | 61 | na | na | na | na | Infinium |
| 90 | 86 | 240 | 296 | 352 | 408 | TaqMan |
| 91 | 131 | 241 | 297 | 353 | 409 | TaqMan |
| 92 | 61 | na | na | na | na | Infinium |
| 93 | 101 | na | na | na | na | Infinium |
| 94 | 101 | na | na | na | na | Infinium |
| 95 | 101 | na | na | na | na | Infinium |
| 96 | 101 | na | na | na | na | Infinium |
| 97 | 61 | na | na | na | na | Infinium |
| 98 | 101 | na | na | na | na | Infinium |
| 99 | 61 | na | na | na | na | Infinium |
| 100 | 101 | na | na | na | na | Infinium |
| 101 | 101 | na | na | na | na | Infinium |
| 102 | 436 | 242 | 298 | 354 | 410 | TaqMan |
| 103 | 61 | na | na | na | na | Infinium |
| 104 | 101 | na | na | na | na | Infinium |
| 105 | 321 | 243 | 299 | 355 | 411 | TaqMan |
| 106 | 160 | 244 | 300 | 356 | 412 | TaqMan |
| 107 | 101 | na | na | na | na | Infinium |
| 108 | 101 | na | na | na | na | Infinium |
| 109 | 101 | 245 | 301 | 357 | 413 | TaqMan |
| 110 | 61 | na | na | na | na | Infinium |
| 111 | 61 | na | na | na | na | Infinium |
| 112 | 61 | na | na | na | na | Infinium |
| 113 | 61 | na | na | na | na | Infinium |
| 114 | 61 | na | na | na | na | Infinium |
| 115 | 61 | na | na | na | na | Infinium |

TABLE 6-continued

Exemplary primers and probes used for genotyping representative SNP markers associated with SR disease resistance.

| Marker (SEQ ID NO) | SNP Position | Forward Primer | Reverse Primer | Probe 1 | Probe 2 | Marker Type |
|---|---|---|---|---|---|---|
| 116 | 101 | na | na | na | na | Infinium |
| 117 | 101 | na | na | na | na | Infinium |
| 118 | 101 | na | na | na | na | Infinium |
| 119 | 101 | na | na | na | na | Infinium |
| 120 | 101 | na | na | na | na | Infinium |
| 121 | 101 | na | na | na | na | Infinium |
| 122 | 61 | na | na | na | na | Infinium |
| 123 | 101 | na | na | na | na | Infinium |
| 124 | 393 | na | na | na | na | Infinium |
| 125 | 61 | na | na | na | na | Infinium |
| 126 | 101 | na | na | na | na | Infinium |
| 127 | 101 | na | na | na | na | Infinium |
| 128 | 101 | na | na | na | na | Infinium |
| 129 | 101 | na | na | na | na | Infinium |
| 130 | 101 | 246 | 302 | 358 | 414 | TaqMan |
| 131 | 101 | na | na | na | na | Infinium |
| 132 | 101 | na | na | na | na | Infinium |
| 133 | 101 | na | na | na | na | Infinium |
| 134 | 61 | na | na | na | na | Infinium |
| 135 | 101 | na | na | na | na | Infinium |
| 136 | 101 | na | na | na | na | Infinium |
| 137 | 61 | na | na | na | na | Infinium |
| 138 | 101 | na | na | na | na | Infinium |
| 139 | 101 | na | na | na | na | Infinium |
| 140 | 101 | na | na | na | na | Infinium |
| 141 | 101 | na | na | na | na | Infinium |
| 142 | 101 | na | na | na | na | Infinium |
| 143 | 101 | na | na | na | na | Infinium |
| 144 | 101 | na | na | na | na | Infinium |
| 145 | 101 | na | na | na | na | Infinium |
| 146 | 101 | na | na | na | na | Infinium |
| 147 | 61 | na | na | na | na | Infinium |
| 148 | 139 | 247 | 303 | 359 | 415 | TaqMan |
| 149 | 101 | na | na | na | na | Infinium |
| 150 | 101 | na | na | na | na | Infinium |
| 151 | 101 | na | na | na | na | Infinium |
| 152 | 101 | na | na | na | na | Infinium |
| 153 | 101 | na | na | na | na | Infinium |
| 154 | 101 | na | na | na | na | Infinium |
| 155 | 101 | na | na | na | na | Infinium |
| 156 | 101 | na | na | na | na | Infinium |
| 157 | 101 | na | na | na | na | Infinium |
| 158 | 101 | na | na | na | na | Infinium |
| 159 | 101 | na | na | na | na | Infinium |
| 160 | 61 | na | na | na | na | Infinium |
| 161 | 101 | na | na | na | na | Infinium |
| 162 | 101 | na | na | na | na | Infinium |
| 163 | 101 | na | na | na | na | Infinium |
| 164 | 101 | na | na | na | na | Infinium |
| 165 | 101 | na | na | na | na | Infinium |
| 166 | 196 | na | na | na | na | Infinium |
| 167 | 101 | na | na | na | na | Infinium |
| 168 | 101 | na | na | na | na | Infinium |
| 169 | 61 | na | na | na | na | Infinium |
| 170 | 61 | na | na | na | na | Infinium |
| 171 | 61 | na | na | na | na | Infinium |
| 172 | 61 | na | na | na | na | Infinium |
| 173 | 61 | na | na | na | na | Infinium |
| 174 | 61 | na | na | na | na | Infinium |
| 175 | 61 | na | na | na | na | Infinium |
| 176 | 61 | na | na | na | na | Infinium |
| 177 | 61 | na | na | na | na | Infinium |
| 178 | 61 | na | na | na | na | Infinium |
| 179 | 61 | na | na | na | na | Infinium |
| 180 | 61 | na | na | na | na | Infinium |
| 181 | 61 | na | na | na | na | Infinium |
| 182 | 61 | na | na | na | na | Infinium |
| 183 | 61 | na | na | na | na | Infinium |
| 184 | 61 | na | na | na | na | Infinium |
| 185 | 61 | na | na | na | na | Infinium |
| 186 | 61 | na | na | na | na | Infinium |
| 187 | 101 | na | na | na | na | Infinium |
| 188 | 61 | na | na | na | na | Infinium |
| 189 | 61 | na | na | na | na | Infinium |
| 190 | 61 | na | na | na | na | Infinium |
| 191 | 61 | na | na | na | na | Infinium |

Example 5. Validation of SR QTLs

Efficacy of individual and multiple SR resistance QTLs were tested using $BC_3F_3$ inbred plants derived from the crosses listed in Table 7. Inbred plants carrying resistant alleles of SR_3.01 from CV258468 background show a reduction of 0.86 in SR rating score when compared to plants carrying susceptible alleles. Inbred plants carrying resistant alleles of SR_6.01 from CV258468 background show a reduction of 1.6 in SR rating score when compared to plants carrying susceptible alleles. Inbred plants carrying resistant alleles of SR_3.01 and SR_6.01 from CV258468 background show a reduction of 2.84 in SR rating score when compared to plants carrying susceptible alleles. Inbred plants carrying resistant alleles of SR_5.01 from CV644930 background show a reduction of 0.85 in SR rating score when compared to plants carrying susceptible alleles. Inbred plants carrying resistant alleles of SR_6.01 from CV644930 background show a reduction of 1.81 in SR rating score when compared to plants carrying susceptible alleles. Inbred plants carrying resistant alleles of SR_5.01 and SR_6.01 from CV644930 background show a reduction of 1.58 in SR rating score when compared to plants carrying susceptible alleles.

TABLE 7

Inbred efficacy test of individual and multiple QTLs.

| Donor Parent | Recurrent Parent | QTL interval | Resistance QTL Profile | SR Infection Score (mean) | Std Error | p-value |
|---|---|---|---|---|---|---|
| CV258468 | CV649307 | SR_3.01 | Absent | 5.38 | 0.38 | 2.69E−07 |
| | | | Present | 4.52 | 0.38 | |
| | | SR_6.01 | Absent | 5.94 | 0.25 | <0.001 |
| | | | Present | 4.34 | 0.25 | |
| | | SR_3.01 & SR_6.01 | Absent | 6.3 | 0.41 | 2.09E−26 |
| | | | Present | 3.46 | 0.4 | |

TABLE 7-continued

Inbred efficacy test of individual and multiple QTLs.

| Donor Parent | Recurrent Parent | QTL interval | Resistance QTL Profile | SR Infection Score (mean) | Std Error | p-value |
|---|---|---|---|---|---|---|
| CV644930 | CV152769 | SR_5.01 | Absent | 5.3 | 0.32 | <0.001 |
| | | | Present | 4.45 | 0.32 | |
| | | SR_6.01 | Absent | 6.01 | 0.25 | <0.001 |
| | | | Present | 4.2 | 0.25 | |
| | | SR_5.01 & SR_6.01 | Absent | 6.22 | 0.21 | 6.60E−26 |
| | | | Present | 4.64 | 0.21 | |

Efficacy of individual and multiple SR resistance QTLs were also tested by crossing $BC_3F_3$ inbred plants with two highly susceptible testers to generate hybrid plants, as shown in Table 8. Hybrid plants carrying resistant alleles of SR_3.01 from CV258468 background show a reduction of 1.75 in SR rating score when compared to plants carrying susceptible alleles. Hybrid plants carrying resistant alleles of SR_6.01 from CV258468 background show a reduction of 1.97 in SR rating score when compared to plants carrying susceptible alleles. Hybrid plants carrying resistant alleles of SR_3.01 and SR_6.01 from CV258468 background show a reduction of 2.72 in SR rating score when compared to plants carrying susceptible alleles. Hybrid plants carrying resistant alleles of SR_5.01 from CV644930 background show a reduction of 0.46 in SR rating score when compared to plants carrying susceptible alleles. Hybrid plants carrying resistant alleles of SR_6.01 from CV644930 background show a reduction of 2.56 in SR rating score when compared to plants carrying susceptible alleles. Hybrid plants carrying resistant alleles of SR_5.01 and SR_6.01 from CV644930 background show a reduction of 2.37 in SR rating score when compared to plants carrying susceptible alleles.

TABLE 8

Hybrid efficacy test of individual and multiple QTLs.

| Donor Parent | Recurrent Parent | QTL interval | Resistance QTL Profile | SR Infection Score (mean) | Std Error | p-value |
|---|---|---|---|---|---|---|
| CV258468 | CV649307 | SR_3.01 | Absent | 5.46 | 0.2 | 7.60E−12 |
| | | | Present | 3.71 | 0.19 | |
| | | SR_6.01 | Absent | 5.93 | 0.13 | <0.001 |
| | | | Present | 3.96 | 0.13 | |
| | | SR_3.01 & SR_6.01 | Absent | 5.9 | 0.23 | 2.90E−19 |
| | | | Present | 3.18 | 0.2 | |
| CV644930 | CV152769 | SR_5.01 | Absent | 5.31 | 0.19 | 0.029734 |
| | | | Present | 4.85 | 0.22 | |
| | | SR_6.01 | Absent | 6.21 | 0.13 | <0.001 |
| | | | Present | 3.65 | 0.13 | |
| | | SR_5.01 & SR_6.01 | Absent | 5.82 | 0.21 | 2.46E−11 |
| | | | Present | 3.45 | 0.35 | |

What is claimed is:

1. A method of producing a corn plant with enhanced southern rust resistance, comprising:
   a) providing a population of corn plants;
   b) obtaining a DNA sample from at least one corn plant within said population;
   c) detecting in said DNA sample the presence of an allele associated with southern rust resistance, wherein said allele is within 5 cM of a "T" corresponding to position 84 of SEQ ID NO:32, and wherein the "T" at said position is associated with enhanced southern rust resistance;
   d) selecting at least a first corn plant from said population of corn plants based on the presence of the allele; and
   e) crossing the plant selected in step d) comprising said allele with a second, different corn plant to produce progeny plants wherein at least one progeny plant comprises the allele associated with southern rust resistance and exhibits enhanced southern rust resistance compared to a plant lacking said allele.

2. The method of claim 1, wherein providing said population comprises backcrossing.

3. The method of claim 2, wherein said backcrossing comprises marker-assisted selection.

4. The method of claim 1, wherein said method further comprises assaying for said at least first corn plant for southern rust resistance.

5. The method of claim 1, wherein said population of corn plants comprises $F_2$-$F_8$ progeny plants.

6. A method of producing a corn plant with enhanced southern rust resistance comprising:
   a) providing a population of corn plants;
   b) detecting in said population the presence of a southern rust resistance allele within 5 cM of a "T" corresponding to position 84 of SEQ ID NO:32, and wherein the "T" at said position is associated with enhanced southern rust resistance genetically linked to a chromosomal segment flanked by marker loci SEQ ID NO: 110 and SEQ ID NO: 168 on chromosome 6; and
   c) selecting from said population at least a first plant comprising said allele, wherein the allele confers enhanced resistance to southern rust compared to a plant lacking said allele.

7. The method of claim 6, wherein said chromosomal segment comprises a nucleic acid sequence selected from the group consisting of SEQ ID NOs: 111-167.

8. The method of claim 6, wherein providing said population of corn plants comprises crossing a corn plant comprising at least a first southern rust resistance allele with a second corn plant of a different genotype lacking said allele to produce progeny plants.

9. The method of claim 6, wherein the population of corn plants comprises $F_2$-$F_6$ progeny plants.

10. The method of claim 6, wherein providing said population comprises backcrossing.

11. The method of claim 10, wherein backcrossing comprises marker-assisted selection in at least two generations.

12. The method of claim 10, wherein backcrossing comprises marker-assisted selection in all generations.

13. The method of claim 6, further comprising assaying the first plant comprising said allele or a progeny thereof comprising the allele for said southern rust resistance.

* * * * *